US009809594B2

(12) United States Patent
Jenekhe et al.

(10) Patent No.: US 9,809,594 B2
(45) Date of Patent: Nov. 7, 2017

(54) NON-FULLERENE ELECTRON ACCEPTORS FOR ORGANIC PHOTOVOLTAIC DEVICES

(71) Applicant: University of Washington Through its Center for Commercialization, Seattle, WA (US)

(72) Inventors: Samson A. Jenekhe, Seattle, WA (US); Haiyan Li, Seattle, WA (US); Taeshik Earmme, Seattle, WA (US); Guoqiang Ren, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

(21) Appl. No.: 14/917,553

(22) PCT Filed: Sep. 10, 2014

(86) PCT No.: PCT/US2014/055030
§ 371 (c)(1),
(2) Date: Mar. 8, 2016

(87) PCT Pub. No.: WO2015/038671
PCT Pub. Date: Mar. 19, 2015

(65) Prior Publication Data
US 2017/0057962 A1 Mar. 2, 2017

Related U.S. Application Data

(60) Provisional application No. 61/876,055, filed on Sep. 10, 2013.

(51) Int. Cl.
*C07D 471/22* (2006.01)
*H01L 51/00* (2006.01)
*C09B 5/62* (2006.01)
*C09B 57/00* (2006.01)
*H01L 51/05* (2006.01)
*H01L 51/42* (2006.01)

(52) U.S. Cl.
CPC ............ *C07D 471/22* (2013.01); *C09B 5/62* (2013.01); *C09B 57/00* (2013.01); *H01L 51/0053* (2013.01); *H01L 51/0072* (2013.01); *H01L 51/0541* (2013.01); *H01L 51/4253* (2013.01); *Y02E 10/549* (2013.01)

(58) Field of Classification Search
CPC .................................................. C07D 211/80
See application file for complete search history.

(56) References Cited

U.S. PATENT DOCUMENTS

| 6,046,342 A | 4/2000 | Jung et al. |
| 2007/0160905 A1 | 7/2007 | Morishita et al. |
| 2011/0101276 A1 | 5/2011 | Rybtchinski et al. |
| 2011/0136333 A1 | 6/2011 | Facchetti et al. |
| 2012/0152357 A1 | 6/2012 | Brown et al. |
| 2012/0255615 A1 | 10/2012 | Sellinger et al. |
| 2012/0273732 A1 | 11/2012 | Jenekhe et al. |

FOREIGN PATENT DOCUMENTS

| CN | 102782011 A | 11/2012 |
| EP | 2 493 960 | 9/2012 |
| WO | 2009/126203 A1 | 10/2009 |
| WO | 2010/011658 A2 | 1/2010 |
| WO | 2011/051292 A1 | 5/2011 |
| WO | 2013/096924 A1 | 6/2013 |
| WO | 2013102038 A1 | 7/2013 |
| WO | 2014/031750 A1 | 2/2014 |
| WO | 2015/038671 A2 | 3/2015 |

OTHER PUBLICATIONS

Li, et al., Synthesis and Properties of Ethylene-Annulated Di(perylene diimides), Organic Letters, 14(20), 5278-5281 (2012).*
International Search Report and Written Opinion dated Mar. 4, 2015, issued in corresponding International Application No. PCT/US2014/055030, filed Sep. 10, 2014, 9 pages.
Ma, W., et al., "Thermally Stable, Efficient Polymer Solar Cells With Nanoscale Control of the Interpenetrating Network Morphology," Advanced Functional Materials 15(10):1617-1622, Oct. 2002.
Miyaura, N., and A. Suzuki, "Palladium-Catalyzed Cross-Coupling Reactions of Organoboron Compounds," chemical Reviews 95(7):2457-2483, Nov. 1995.
Mori, D., et al., "Polymer/Polymer Blend Solar Cells Improved by Using High-Molecular-Weight Fluorene-Based Copolymer as Electron Acceptor," ACS Applied Materials & Interfaces 4(7):3325-3329, Jul. 2012.
Nielsen, C.B., et al., "Efficient Truxenone-Based Acceptors for Organic Photovoltaics," Journal of Materials Chemistry A 1(1):73-76, Jan. 2013.
Nietfeld, J.P., et al., "Structural Effects on the Electronic Properties of Extended Fused-Ring Thieno[3,4-b]pyrazine Analogues," Journal of Organic Chemistry 76(15):6383-6388, Aug. 2011.
Palmaerts, A., et al., "Development of Novel Processable Electron Accepting Conjugated Polymers Containing Fluoranthene Units in the Main Chain," Polymer 50(21):5007-5015, Oct. 2009.
Park, S.H., et al., "Bulk Heterojunction Solar Cells With Internal Quantum Efficiency Approaching 100%," Nature Photonics 3(3):297-302, May 2009.
Pho, T.V., et al., "Self-Assembling Decacyclene Triimides Prepared through a Regioselective Hextuple Friedel-Crafts Carbamylation," Angewandte Chemie 52(5):1446-1451, Jan. 2013.

(Continued)

*Primary Examiner* — Erich A Leeser
(74) *Attorney, Agent, or Firm* — Christensen O'Connor Johnson Kindness PLLC

(57) ABSTRACT

Non-fullerene electron acceptors for highly efficient organic photovoltaic devices are described. The non-fullerene electron acceptors have an extended, rigid, π-conjugated electron-deficient framework that can facilitate exciton and charge derealization. The non-fullerene electron acceptors can physically mix with a donor polymer and facilitate improved electron transport. The non-fullerene electron acceptors can be incorporated into organic electronic devices, such as photovoltaic cells.

19 Claims, 8 Drawing Sheets

(56) References Cited

OTHER PUBLICATIONS

Ponce Ortiz, R., et al., "Molecular and Electronic-Structure Basis of the Ambipolar Behavior of Naphthalimide-Terthiophene Derivatives: Implementation in Organic Field-Effect Transistors," Chemistry 19(37):12458-12467, Sep. 2013.
Ponce Ortiz, R., et al., "Organic n-Channel Field-Effect Transistors Based on Arylenediimide-Thiophene Derivatives," Journal of the American Chemical Society 132(24):8440-8452, Jun. 2010.
Ren, G., et al., "Non-Fullerene Acceptor-Based Bulk Heterojunction Polymer Solar Cells: Engineering the Nanomorphology via Processing Additives," Advanced Energy Materials 1(5):946-953, Oct. 2011.
Reusch, W., "Virtual Textbook of Organic Chemistry," Jun. 2010, <http://www2.chemistry.msu.edu/faculty/reusch/VirtTxtJml/intro1.htm> [retrieved May 2, 2016], 4 pages.
Roncali, J., et al., "From One- to Three-Dimensional Organic Semiconductors: In Search of the Organic Silicon?" Advanced Materials 19(16):2045-2060, Aug. 2007.
Sariciftci, N.S., et al., "Photoinduced Electron Transfer From a Conducting Polymer to Buckminsterfullerene," Science 258(5087):1474-1476, Nov. 1992.
Schwenn, P.E., et al., "A Small Molecule Non-Fullerene Electron Acceptor for Organic Solar Cells," Advanced Energy Materials 1(1):73-81, Jan. 2011.
Shaheen, S.E., et al., "2.5% Efficient Organic Plastic Solar Cells," Applied Physics Letters 78(6):841-843, Feb. 2011.
Small, C.E., et al., "High-Efficiency Inverted Dithienogermole-Thienopyrrolodione-Based Polymer Solar Cells," Nature Photonics 6(2)115-120, Feb. 2012.
Sonar, P., et al., "Organic Non-Fullerene Acceptors for Organic Photovoltaics," Energy & Environmental Science 4(5):1558-1574, May 2011.
Stille, J.K., "The Palladium-Catalyzed Cross-Coupling Reactions of Organotin Reagents With Organic Electrophiles," Angewandte Chemie 25(6):508-524, Jun. 1986.
Stolar, M., and T. Baumgartner, "Organic n-Type Materials for Charge Transport and Charge Storage Applications," Physical Chemistry Chemical Physics 15(23):9007-9024, Jun. 2013.
Subramaniyan, S., et al., "Effects of Side Chains on Thiazolothiazole-Based Copolymer Semiconductors for High Performance Solar Cells," Advanced Energy Materials 1(5):854-860, Oct. 2011.
Subramaniyan, S., et al., "New Thiazolothiazole Copolymer Semiconductors for Highly Efficient Solar Cells," Macromolecules 44(16):6245-6248, Aug. 2011.
Sun, Y., et al., "Inverted Polymer Solar Cells Integrated With a Low-Temperature-Annealed Sol-Gel-Derived ZnO Film as an Electron Transport Layer," Advanced Materials 23(14):1679-1683, Apr. 2011.
Sun, Z., et al., "Soluble and Stable Zethrenebis(dicarboximide) and Its Quinone," Organic Letters 12(20):4690-4693, Oct. 2010.
Tan, L., et al., "New Air-Stable Solution-Processed Organic n-Type Semiconductors Based on Sulfur-Rich Core-Expanded Naphthalene Diimides," Journal of Materials Chemistry 21(44):18042-18048, Nov. 2011.
Thompson, B.C., and J.M. Fréchet, "Polymer-Fullerene Composite Solar Cells," Angewandte Chemie 47(1):58-77, Dec. 2007.
Tonzola, C.J., et al., "New n-Type Organic Semiconductors: Synthesis, Single Crystal Structures, Cyclic Voltammetry, Photophysics, Electron Transport, and Electroluminescence of a Series of Diphenylanthrazolines," Journal of the American Chemical Society 125(44):13548-13558, Nov. 2003.
Trost, B.M., "Antiaromatic Peripheral Systems. Synthesis and Chemistry of Pyracyloquinone," Journal of the American Chemical Society 91(4):918-923, Feb. 1969.
Trost, B.M., et al., "Perturbed [12]Annulenes. The Synthesis of Pyracylenes," Journal of the American Chemical Society 93(3):737-745, Feb. 1971.

Usta, H., et al., "n-Channel Semiconductor Materials Design for Organic Complementary Circuits," Accounts of Chemical Research 44(7):501-510, Jul. 2011.
Verheijen, M.A., et al., "The Structure of Different Phases of Pure C70 Crystals," Chemical Physics 166(1-2):287-297, Oct. 1992.
Wang, E., et al., "Small Band Gap Polymers Synthesized via a Modified Nitration of 4,7-Dibromo-2,1,3-benzothiadiazole," Organic Letters 12(20):4470-4473, Oct. 2010.
Wang, Z., et al., "Anthracenedicarboximides as Air-Stable N-Channel Semiconductors for Thin-Film Transistors With Remarkable Current On-Off Ratios," Journal of the American Chemical Society 129(44):13362-13363, Nov. 2007.
Wen, L., et al., "New Tunable Thieno[3,4-b]pyrazine-Based Materials," Synthetic Metals 159(21-22):2299-2301, Nov. 2009.
Woo, C.H., et al., "Phenyl vs Alkyl Polythiophene: A Solar Cell Comparison Using a Vinazene Derivative as Acceptor," Chemistry of Materials 22(5):1673-1679, Mar. 2010.
Xin, H., et al., "Enhanced Open Circuit Voltage and Efficiency of Donor-Acceptor Copolymer Solar Cells by Using Indene-C60 Bisadduct," Chemistry of Materials 24(11):1995-2001, Jun. 2012.
Yan, H., et al., "A High-Mobility Electron-Transporting Polymer for Printed Transistors," Nature 457(7230):679-686, Feb. 2007.
Yu, G., et al., "Polymer Photovoltaic Cells: Enhanced Efficiencies via a Network of Internal Donor-Acceptor Heterojunctions," Science 270(5243):1789-1791, Dec. 1995.
Zang, Y., et al., "Integrated Molecular, Interfacial, and Device Engineering Towards High-Performance Non-Fullerene Based Organic Solar Cells," Advanced Materials 26(32):5708-5714, Aug. 2014.
Zaumseil, J., and H. Sirringhaus, "Electron and Ambipolar Transport in Organic Field-Effect Transistors," Chemical Reviews 107(4):1296-1323, Apr. 2007.
Zhan, X. et al., "A High-Mobility Electron-Transport Polymer With Broad Absorption and Its Use in Field-Effect Transistors and All-Polymer Solar Cells," Journal of the American Chemical Society 129(23):7246-7247, Jun. 2007.
Zhan, X., et al., "Rylene and Related Diimides for Organic Electronics," Advanced Materials 23(2):268-284, Jan. 2011.
Zheng, Q., et al., "Pyromellitic Diimides: Minimal Cores for High Mobility n-Channel Transistor Semiconductors," Journal of the American Chemical Society 130(44):14410-14411, Nov. 2008.
Zhou, E. et al. "All-Polymer Solar Cells From Perylene Diimide Based Copolymers: Material Design and Phase Separation Control," Angewandte Chemie 50(12):2799-2803, Mar. 2011.
Zhou, T., et al., "Nitrile-Substituted QA Derivatives: New Acceptor Materials for Solution-Processable Organic Bulk Heterojunction Solar Cells," Advanced Energy Materials 1(3):431-439, May 2011.
Zhou, Y., et al., "Non-Fullerene Acceptors Containing Fluoranthene-Fused Imides for Solution-Processed Inverted Organic Solar Cells," Chemical Communications 49(51):5802-5804, Jun. 2013.
Zhou, Y., et al., "A Non-Fullerene Small Molecule as Efficient Electron Acceptor in Organic Bulk Heterojunction Solar Cells," Advanced Materials 24(7):957-961, Feb. 2012.
Zhu, Y., et al., "Poly(pyrazinoquinoxaline)s: New n-Type Conjugated Polymers That Exhibit Highly Reversible Reduction and High Electron Affinity," Macromolecular Rapid Communications 25(21):1829-1834, Nov. 2004.
Ahmed, E., et al., "Benzobisthiazole-Based Donor-Acceptor Copolymer Semiconductors for Photovoltaic Cells and Highly Stable Field-Effect Transistors," Macromolecules 44(18):7207-7219, Sep. 2011.
Ahmed, E., et al., "Design of New Electron Acceptor Materials for Organic Photovoltaics: Synthesis, Electron Transport, Photophysics, and Photovoltaic Properties of Oligothiophene-Functionalized Naphthalene Diimides," Chemistry of Materials 23(20):4563-4577, Oct. 2011.
Anthony, J.E., et al., "n-Type Organic Semiconductors in Organic Electronics," Advanced Materials 22(34):3876-3892, Aug. 2010.
Anthony, J.E., "Small-Molecule, Nonfullerene Acceptors for Polymer Bulk Heterojunction Organic Photovoltaics," Chemistry of Materials 23(3):583-590, Feb. 2011.

(56) References Cited

OTHER PUBLICATIONS

Babel, A., and S.A. Jenekhe, "High Electron Mobility in Ladder Polymer Field-Effect Transistors," Journal of the American Chemical Society 125(45):13656-13657, Nov. 2003.

Beaupré, S., et al., "Multicolored Electrochromic Cells Based on Poly(2,7-carbazole) Derivatives for Adaptive Camouflage," Chemistry of Materials 21(8):1504-1513, Apr. 2009.

Bloking, J.T., et al., "Solution-Processed Organic Solar Cells With Power Conversion Efficiencies of 2.5% Using Benzothiadiazole/Imide-Based Acceptors," Chemistry of Materials 23(24):5484-5490, Dec. 2011.

Blom, P.W.M., et al., "Device Physics of Polymer:Fullerene Bulk Heterojunction Solar Cells," Advanced Materials 19(12):1551-1566, Jun. 2007.

Brabec, C.J., et al., "Effect of LiF/Metal Electrodes on the Performance of Plastic Solar Cells," Applied Physics Letters 80(7):1288-1290, Feb. 2002.

Briseno, A.L., et al., "Perylenediimide Nanowires and Their Use in Fabricating Field-Effect Transistors and Complementary Inverters," Nano Letters 7(9):2847-2853, Sep. 2007.

Briseno, A.L., et al., "Self-Assembly, Molecular Packing, and Electron Transport in n-Type Polymer Semiconductor Nanobelts," Chemistry of Materials 20(14):4712-4719, Jul. 2008.

Chen, C.-H., et al., "Synthesis and Characterization of Bridged Bithiophene-Based Conjugated Polymers for Photovoltaic Applications: Acceptor Strength and Ternary Blends," Macromolecules 43(2):697-708, Jan. 2010.

Chen, H.-Y., et al., "Polymer Solar Cells With Enhanced Open-Circuit Voltage and Efficiency," Nature Photonics 3(11):649-653, Nov. 2009.

Chen, Z., et al., "Naphthalenedicarboximide- vs Perylenedicarboximide-Based Copolymers. Synthesis and Semiconducting Properties in Bottom-Gate N-Channel Organic Transistors," Journal of the American Chemical Society 131(1):8-9, Jan. 2009.

Chochos, C.L., et al., "Rational Design of n-Type Organic Materials for High Performance Organic Photovoltaics," RSC Advances 3(20):7160-7181, May 2013.

Clarke, T.M., and J.R., Durrant, "Charge Photogeneration in Organic Solar Cells," Chemical Reviews 110(11):6736-6767, Nov. 2010.

Duan, L., et al., "Novel Naphthalimide Derivatives With Near-Infrared Emission: Synthesis via Photochemical Cycloaromatization. Fluorescence in Solvents and Living Cell," Tetrahedron Letters 50(1):22-25, Jan. 2009.

Earmme, T., et al., "All-Polymer Bulk Heterojunction Solar Cells With 4.8% Efficiency Achieved by Solution Processing From a Co-Solvent," Advanced Materials 26(35):6080-6085, Sep. 2014.

Earmme, T., et al., "All-Polymer Solar Cells With 3.3% Efficiency Based on Naphthalene Diimide-Selenophene Copolymer Acceptor," Journal of the American Chemical Society 135(40):14960-14963, Oct. 2013.

Gao, X., et al., "Core-Expanded Naphthalene Diimides Fused With 2-(1,3-Dithiol-2-ylidene)malonitrile Groups for High-Performance, Ambient-Stable, Solution-Processed n-Channel Organic Thin Film Transistors," Journal of the American Chemical Society 132(11):3697-3699, Mar. 2010.

Geng, Y., et al., "Monodisperse Oligofluorenes Forming Glassy-Nematic Films for Polarized Blue Emission," Chemistry of Materials 15(2):542-549, Jan. 2003.

Goel, A., et al., "Size Analysis of Single Fullerene Molecules by Electron Microscopy," Carbon 42(10):1907-1915, 2004.

González, S.R., et al., "A β-Naphthaleneimide-Modified Terthiophene Exhibiting Charge Transfer and Polarization Through the Short Molecular Axis. Joint Spectroscopic and Theoretical Study," Journal of Physical Chemistry A 112(29):6732-6740, Jul. 2008.

Gregg, B.A., "Entropy of Charge Separation in Organic Photovoltaic Cells: The Benefit of Higher Dimensionality," Journal of Physical Chemistry Letters 2(24):3013-3015, Dec. 2011.

Gui, K., et al., "A Flexible n-Type Organic Semiconductor for Optoelectronics," Journal of Materials Chemistry 22(5):1800-1806, Feb. 2012.

Günes, S., et al., "Conjugated Polymer-Based Organic Solar Cells," Chemical Reviews 107(4):1324-1338, Apr. 2007.

Guo, X., and M.D. Watson, "Conjugated Polymers From Naphthalene Bisimide," Organic Letters 10(23):5333-5336, Dec. 2008.

He, Z., et al., "Enhanced Power-Conversion Efficiency in Polymer Solar Cells Using an Inverted Device Structure," Nature Photonics 6(9):591-595, Sep. 2012.

Herrera, H., et al., "Linear and Star-Shaped Naphthalimide-Fused Pyrazinacenes," Chemical Communications 49(7):713-715, Jan. 2013.

Hong, D.-J., et al., "Self-Organized Spiral Columns in Laterally Grafted Rods," Chemical Communications 46(27):4896-4898, Jul. 2010.

Huang, X., et al., "Novel Dyes Based on Naphthalimide Moiety as Electron Acceptor for Efficient Dye-Sensitized Solar Cells," Dyes and Pigments 90(3):297-303, Sep. 2011.

Hundt, N., et al., "Polymers Containing Rigid Benzodithiophene Repeating Unit With Extended Electron Delocalization," Organic Letters 11(19):4422-4425, Oct. 2009.

Hüttner, S., et al., "n-Type Organic Field Effect Transistors From Perylene Bisimide Block Copolymers and Homopolymers," Applied Physics Letters 92(9):093302, 2008, 3 pages.

International Preliminary Report on Patentability dated Feb. 24, 2015, issued in corresponding International Application No. PCT/US2013/055984, filed Aug. 21, 2013, 1 page.

International Search Report and Written Opinion dated Dec. 4, 2013, issued in corresponding International Application No. PCT/US2013/055984, filed Aug. 21, 2013, 12 pages.

Jamieson, F.C., et al., "Fullerene Crystallisation as a Key Driver of Charge Separation in Polymer/Fullerene Bulk Heterojunction Solar Cells," Chemical Science 3(2):485-492, Feb. 2012.

Johansson Seechurn, C.C.C., et al., "Palladium-Catalyzed Cross-Coupling: A Historical Contextual Perspective to the 2010 Nobel Prize," Angewandte Chemie 51(21):5062-5085, May 2012.

Kanibolotsky, A.L., et al., "Star-Shaped π-Conjugated Oligomers and Their Applications in Organic Electronics and Photonics," Chemical Society Reviews 39(7):2695-2728, Jul. 2010.

Kim, F.S., et al., "One-Dimensional Nanostructures of π-Conjugated Molecular Systems: Assembly, Properties, and Applications From Photovoltaics, Sensors, and Nanophotonics to Nanoelectronics," Chemistry of Materials 23(3):682-732, Feb. 2011.

Kim, J.Y., et al., "Efficient Tandem Polymer Solar Cells Fabricated by All-Solution Processing," Science 317(5835):222-225, Jul. 2007.

Kwon, T.W., et al., "n-Type Conjugated Dendrimers: Convergent Synthesis, Photophysics, Electroluminescence, and Use as Electron-Transport Materials for Light-Emitting Diodes," Chemistry of Materials 16(23):4657-4666, Nov. 2004.

Letizia, J.A., et al., "n-Channel Polymers by Design: Optimizing the Interplay of Solubilizing Substituents, Crystal Packing, and Field-Effect Transistor Characteristics in Polymeric Bithiophene-Imide Semiconductors," Journal of the American Chemical Society 130(30):9679-9694, Jul. 2008.

Li, G., et al., "High-Efficiency Solution Processable Polymer Photovoltaic Cells by Self-Organization of Polymer Blends," Nature Materials 4(11):864-868, Nov. 2005.

Li, G., et al., "Polymer Solar Cells," Nature Photonics 6(3):153-161, Mar. 2012.

Li, H., et al. "High-Mobility n-Type Conjugated Polymers Based on Electron-Deficient Tetraazabenzodifluoranthene Diimide for Organic Electronics," Journal of the American Chemical Society 135(40):14920-14923, Oct. 2013.

Li, H., et al. "Tetraazabenzodifluoranthene Diimides: Building Blocks for Solution-Processable n-Type Organic Semiconductors," Angewandte Chemie 52(21):5513-5517, May 2013.

Liang, Y., et al., "For the Bright Future—Bulk Heterojunction Polymer Solar Cells With Power Conversion Efficiency of 7.4%," Advanced Materials 22(20):E135-E138, May 2010.

Liu, S., et al., "Synthesis and Optical Properties of a Series of Thermally Stable Diphenylanthrazolines," Dyes and Pigments 81(3)218-223, Jun. 2009.

(56) References Cited

OTHER PUBLICATIONS

Liu, T., and A. Troisi, "What Makes Fullerene Acceptors Special as Electron Acceptors in Organic Solar Cells and How to Replace Them," Advanced Materials 25(7):1038-1041, Feb. 2013.
Lo, S.-C., and P.L. Burn, "Development of Dendrimers: Macromolecules for Use in Organic Light-Emitting Diodes and Solar Cells," Chemical Reviews 107(4):1097-1116, Apr. 2007.

* cited by examiner

BFI-P2

DBFI-T

DBFI-T

NON-FULLERENE ELECTRON ACCEPTORS FOR ORGANIC PHOTOVOLTAIC DEVICES

CROSS-REFERENCE TO RELATED APPLICATIONS

This application claims the benefit of U.S. Patent Application No. 61/876,055, filed Sep. 10, 2013, the disclosure of which is hereby incorporated by reference in its entirety.

STATEMENT OF GOVERNMENT LICENSE RIGHTS

This invention was made with Government support under N00014-11-1-0317, awarded by the Office of Naval Research; CBET-1435912, awarded by the National Science Foundation; and DE-FG02-07ER46467, awarded by the Department of Energy. The Government has certain rights in the invention.

BACKGROUND

Among the most important scientific challenges facing society today is finding a way to meet the energy needs of the world's growing population via an environmentally sustainable paradigm. The sun represents the most abundant potential source of pollution-free energy on earth. Considerable research effort on photovoltaic materials and devices has led to much progress in the last 20 years. However, energy from current photovoltaic technologies is too expensive compared with that from fossil fuels. Novel materials and devices that could potentially revolutionize solar energy conversion technologies, making them cost-competitive with fossil fuels, are needed.

A solar cell (or photovoltaic cell) is a semiconductor device that directly converts absorbed sunlight (photons) into electricity. Incident photons in a semiconductor create excitons (bound electron-hole pairs) whose subsequent dynamics, relaxation, and dissociation are crucial to the photoconversion process. Equally important to the overall efficiency of the photon-to-electricity conversion is the nature of the charge carrier transport to collecting electrodes after exciton dissociation into free charge carriers.

Light absorption in organic/polymer semiconductors creates Frenkel excitons with large binding energies (~0.4-1.0 eV) and small diffusion lengths (5-20 nm). Consequently, efficient photogeneration of free charge carriers in organic photovoltaics (OPVs) requires dissociation of excitons at a heterojunction with another material having highest occupied molecular orbital/lowest unoccupied molecular orbital (HOMO/LUMO) energy level offsets suitable for exciton dissociation. Bulk heterojunction (BHJ) organic photovoltaic (OPV) cells, consisting of a binary blend or composite of a donor polymer and an acceptor material, address the problem of small exciton diffusion lengths (Ld=5-20 nm) in current organic/polymer semiconductors.

Extensive studies of such BHJ-OPV cells have focused largely on blends or nanocomposites of donor polymer with acceptor materials based on fullerenes. BHJ-OPV cells based on [60]- and [70]-fullerene derivatives (PCBMs) and donor polymers currently have high power conversion efficiencies achieved by optimization of factors such as molecular engineering of the donor polymer, blend composition, processing conditions, various annealing protocols, and use of processing additives. However, further advances in improving the efficiencies of polymer solar conversion systems to commercially useful levels (>15-18%) require major innovations in acceptor and donor materials and optimization of device architectures at the molecular- and nanoscales. In addition, a better fundamental understanding of the photoconversion processes, charge transport, and charge collection in BHJ solar cells is critical towards achieving the theoretical device conversion efficiency.

PCBM fullerene derivatives such as [6,6]-phenyl-$C_{60}$-butyric acid methyl ester ($PC_{60}BM$), [6,6]-phenyl-$C_{70}$-butyric acid methyl ester ($PC_{70}BM$), and other fullerenes have attributes which make them successful as acceptors in OPVs. These attributes include: (i) the existence of low lying excited states in the monoanions, which leads to substantial enhancement in charge separation rates without affecting the charge recombination rates; (ii) the large $\pi$-conjugated molecular structure which supports efficient electronic delocalization and polaron formation; (iii) the rigid molecular architecture and high molecular diffusion that facilitate facile aggregation into a phase-separated nanoscale morphology for efficient charge separation and transport; and (iv) the three-dimensional (3D) spherical structure, which results in a large decrease in Coulomb barrier for charge separation due to enhanced entropic effects and enables isotropic charge transport. The attributes can help guide the design of highly efficient non-fullerene electron acceptors for OPVs.

As discussed above, fullerene-based electron acceptors have provided the foundation for advances in fundamental understanding of charge photogeneration and practical developments in organic photovoltaics (OPVs) in the last 20 years. While donor polymers in OPVs have been successfully optimized in recent years, as shown by the steady increase in power conversion efficiency (PCE) of single-junction OPV cells from under 3% to current 7-9% as the donor polymer has changed from poly(phenylene vinylene) derivatives to poly(3-hexylthiophene) to narrow band gap copolymers, non-fullerene electron acceptors reported so far have shown significantly inferior electron accepting properties, resulting in bulk heterojunction (BHJ) solar cells with low PCEs (<3%). Nevertheless, the prospects of enabling new pathways to OPVs while overcoming the small photovoltage, high cost, and other limitations of fullerene-based OPVs motivate efforts to discover alternative organic electron acceptors.

In contrast to PCBMs and other fullerene acceptors, semiconductors (e.g., oligomeric semiconductors) that incorporate multiple chromophores into one molecule combine the advantages of small molecules (e.g., ease of synthesis, purification and no batch-to-batch variation in quality) and the favorable properties of macromolecules (e.g., large molar mass, good solution processability, good mechanical and physical properties, good film-forming properties, etc.) and can be promising electron acceptor candidates. Thus, design and synthesis of electron acceptors that possess similar electronic structures and charge generation/transport behaviors as fullerenes, but that overcome the limitations of fullerenes, can be an efficient approach to high performance electron acceptors for OPVs. The present disclosure seeks to fulfill these needs and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides, inter alia, compounds that are electron acceptors, having Formula (I):

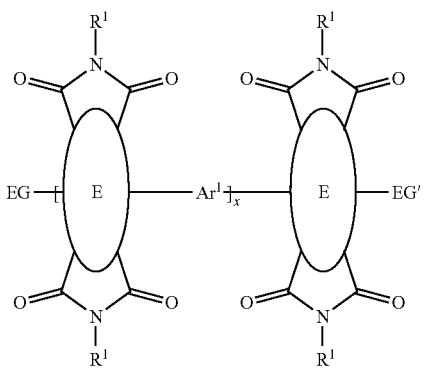

wherein:

EG and EG' are each independently $(W)_m$—W', wherein W is independently selected from arylene, heteroarylene, alkenylene, and alkynylene, each optionally substituted by 1, 2, 3, or 4 substituents independently selected from halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, CN, $NO_2$, and OH;

W' is independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, $C_{2-50}$ alkoxy, CN, $NO_2$, and OH; and m is 0, 1, or 2;

E is a monocyclic or polycyclic aromatic core;

$Ar^1$ is a π-conjugated linker;

$R^1$ is each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH; and x is 1 or 2.

In another aspect, the present disclosure provides, inter alia, compounds that are electron acceptors, having Formula (II):

EG-A$^1$-EG'  (II)

wherein:

EG and EG' are each independently $(W)_m$—W', wherein W is independently selected from arylene, heteroarylene, alkenylene, and alkynylene, each optionally substituted by 1, 2, 3, or 4 substituents independently selected from halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, CN, $NO_2$, and OH;

W' is independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, $C_{2-50}$ alkoxy, CN, $NO_2$, and OH; and m is 0, 1, or 2; and $A^1$ is selected from

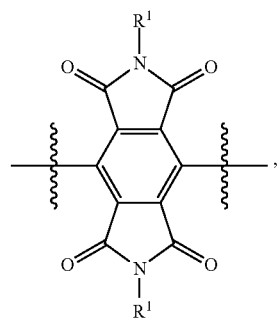

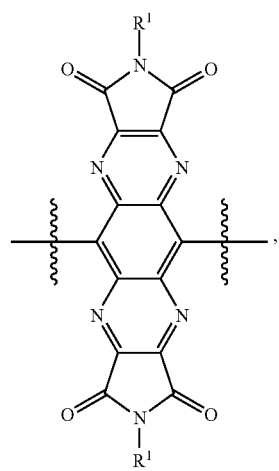

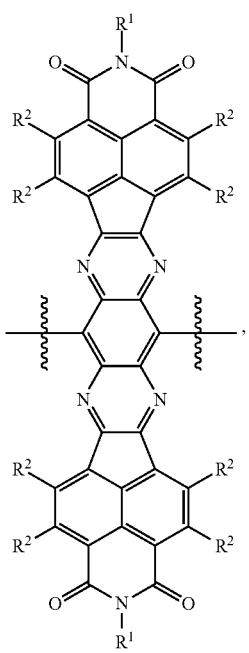

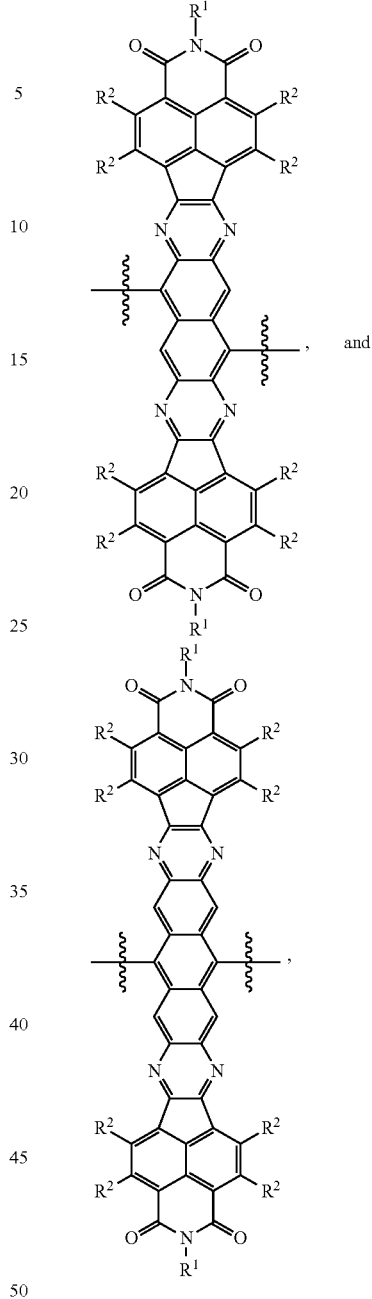

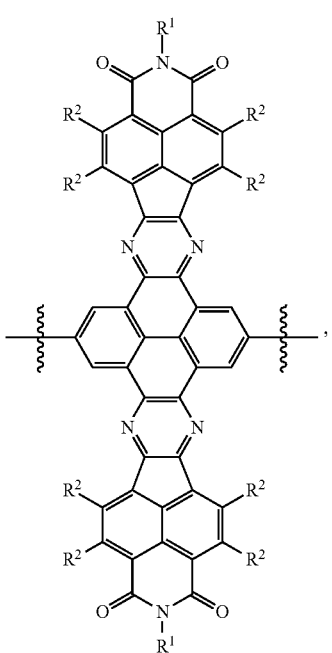

wherein $R^1$ and $R^2$ are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH;

provided that

EG and EG' are not both H, and

EG and EG' are not both halo.

In yet another aspect, the present disclosure provides, inter alia, compounds that are electron acceptors, having Formula (III):

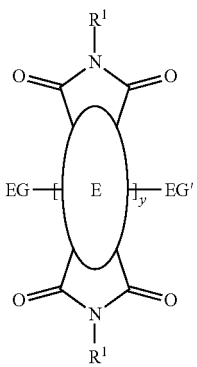

(III)

wherein:

EG and EG' are each independently $(W)_m$—W',
wherein W is independently selected from arylene, heteroarylene, alkenylene, and alkynylene, each optionally substituted by 1, 2, 3, or 4 substituents independently selected from halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, CN, $NO_2$, and OH;

W' is independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, $C_{2-50}$ alkoxy, CN, $NO_2$, and OH; and m is 0, 1, or 2;

E is a monocyclic or polycyclic aromatic core;

$R^1$ is each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH; and y is 2 or 3.

The present disclosure further provides compositions including a compound of Formula (I), (II), or (III).

The present disclosure further provides electronic devices, such as optoelectronic devices including a compound of Formula (I), (II), or (III). For example, the device can be a photovoltaic cell such as an organic photovoltaic cell. The device can be a transistor. In some embodiments, the device is a complementary electronic circuit such as an inverter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
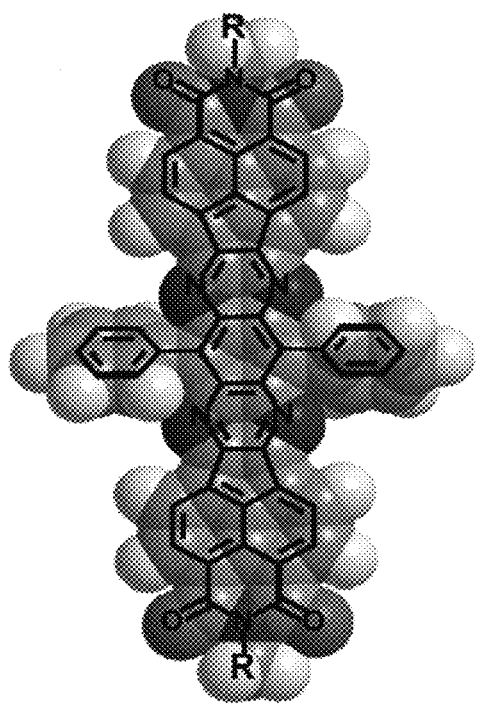
FIG. 1A is a representation of a space filling molecular model of an embodiment of a non-fullerene electron acceptor of the present disclosure.

The present disclosure provides non-fullerene electron acceptors for highly efficient OPVs. The non-fullerene electron acceptors have an extended, rigid, π-conjugated electron-deficient framework that can facilitate exciton and charge delocalization. The non-fullerene electron acceptors can physically mix with a donor polymer and facilitate improved electron transport.

Without wishing to be bound by theory, it is believed that one-dimensional (1D) π-conjugated organic semiconductors have anisotropic charge transport and optical properties, which can render optimum molecular orientation difficult to attain when the semiconductors are incorporated into devices. However, it is believed that non-fullerene electron acceptors of the present disclosure can improve upon 1D π-conjugated organic semiconductors by the adoption of a non-planar three-dimensional (3D) architecture.

The non-planar non-fullerene electron acceptors can decrease (e.g., eliminate) the formation of intermolecular exciplexes at donor/acceptor interfaces, facilitate isotropic electron transport even within a poor crystalline thin film, and enhance charge separation due to entropic effects. The non-fullerene electron acceptors can have a large density of states at the lowest unoccupied molecular orbital (LUMO). Furthermore, the monoanions of the non-fullerene electron acceptors can allow for a large charge separation rate.

In some embodiments, the non-fullerene electron acceptors have a multi-chromophoric structure, such as a dimer or a trimer (i.e., compounds of Formula (I) or (II) having 2 or 3 E-containing chromophores), which can enhance the density of states at the LUMO, achieve 3D non-planar conformation, and enlarge the π-conjugated framework. The dimer or timer can have a low weight average molecular weight, such as a weight average molecular weight of less than 5,000 (e.g., less than 4,500, less than 4,000, or less than 3,000). Compared to higher weight average molecular weight oligomers and polymers (e.g., having a weight average molecular weight of 5,000 or greater), the low weight average molecular weight dimer or trimer can be easily processed in solution. For example, the low weight average molecular weight dimer or trimer can have good solubility and can be easily dissolved in a solvent. Thus, the low weight average molecular weight dimer or timer can be easily incorporated into organic electronic devices. The low weight average molecular weight dimer or trimer can also be easily, controllably, and reproducibly synthesized.

In some embodiments, the non-fullerene electron acceptors (e.g., low weight average molecular weight dimer or trimer) have good photovoltaic properties. For example, the non-fullerene electron acceptors can have a power conversion efficiency (PCE) of greater than or equal to 1% (e.g., greater than or equal to 2%, greater than or equal to 5%, or greater than or equal to 10%). The non-fullerene electron acceptors can have good solution processability, good thermal stability, high photovoltage, high photocurrent, and/or efficient solid-state morphology. For example, the non-fullerene electron acceptors can have a solubility of greater than or equal to 5 mg/mL (e.g., greater than or equal to 10 mg/mL, greater than or equal to 20 mg/mL, or greater than or equal to 30 mg/mL). The non-fullerene electron acceptors can have a stability at a temperature of greater than or equal to 300° C. (greater than or equal to 400° C., or greater than or equal to 450° C.). The non-fullerene electron acceptors can have a photovoltage of greater than or equal to 0.6 V (greater than or equal to 1 V, greater than or equal to 1.5 V, or greater than or equal to 2 V); and/or a photocurrent of greater than or equal to 2.0 mA/cm$^2$ (e.g., greater than or equal to 3.0 mA/cm$^2$, greater than or equal to 5 mA/cm$^2$, or greater than or equal to 7 mA/cm$^2$). The non-fullerene electron acceptors can also offer synthetic versatility and tunable electronic properties, depending on structural variations.

The present disclosure provides, inter alia, compounds that are electron acceptors, having Formula (I):

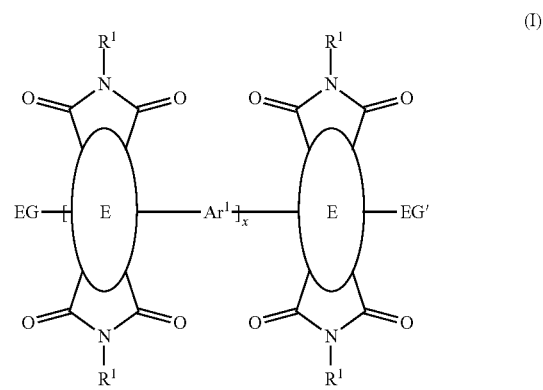

wherein:

EG and EG' are each independently $(W)_m$—W', wherein W is each independently selected from arylene, heteroarylene, alkenylene, and alkynylene, each optionally substituted by 1, 2, 3, or 4 substituents independently selected from halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, CN, NO$_2$, and OH;

W' is independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, $C_{2-50}$ alkoxy, CN, NO$_2$, and OH; and m is 0, 1, or 2;

E is a monocyclic or polycyclic aromatic core;

Ar$^1$ is a π-conjugated linker;

R$^1$ is each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH;

or $R^1$ is each independently selected from

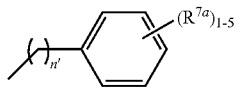 and 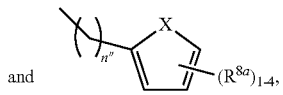

wherein $R^{7a}$ and $R^{8a}$ are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH, wherein n' and n" are each 0-50; and x is 1 or 2.

The present disclosure further provides, inter alia, compounds that are electron acceptors, having Formula (II):

$$EG-A^1-EG'  \qquad (II)$$

wherein:

EG and EG' are each independently $(W)_m-W'$, wherein W is independently selected from arylene, heteroarylene, alkenylene, and alkynylene, each optionally substituted by 1, 2, 3, or 4 substituents independently selected from halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, CN, $NO_2$, and OH;

W' is independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, $C_{2-50}$ alkoxy, CN, $NO_2$, and OH; and m is 0, 1, or 2; and $A^1$ is selected from

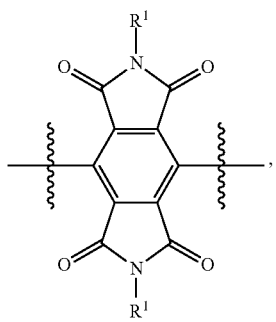

-continued

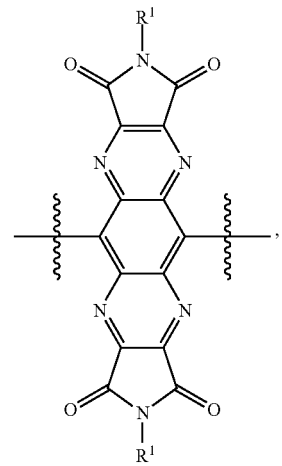

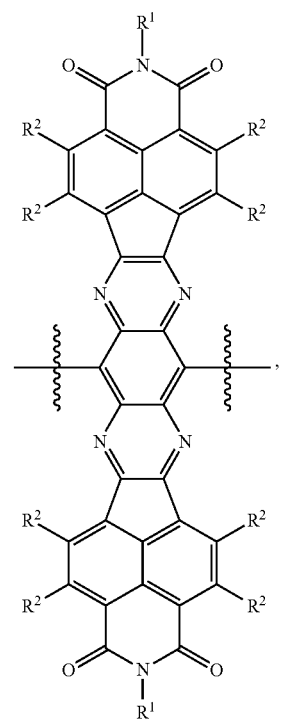

-continued

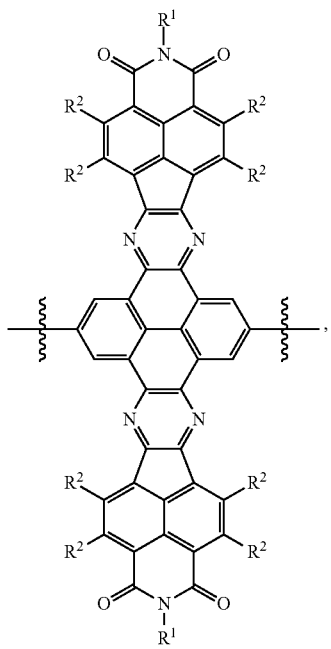

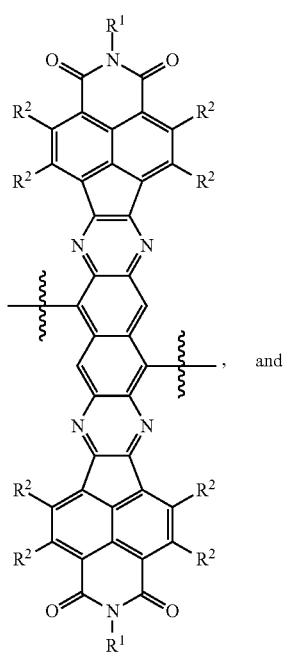 and

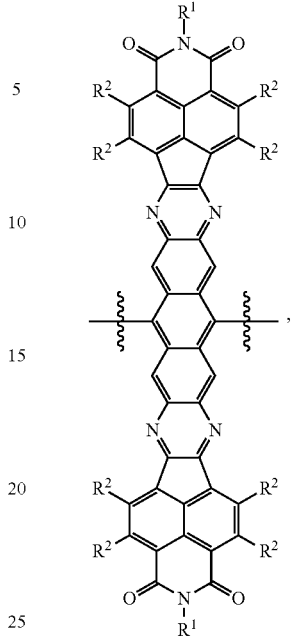

wherein $R^1$ and $R^2$ are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, NO$_2$, and OH;

or $R^1$ is each independently selected from

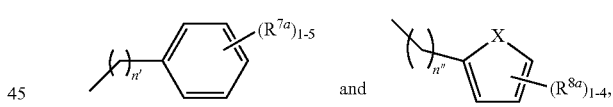

wherein $R^{7a}$ and $R^{8a}$ are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, NO$_2$, and OH, wherein n' and n" are each 0-50;

provided that

EG and EG' are not both H, and

EG and EG' are not both halo.

The present disclosure further provides, inter alia, compounds that are electron acceptors, having Formula (III):

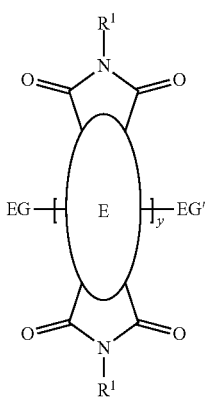

(III)

wherein:

EG and EG' are each independently $(W)_m$—W', wherein W is independently selected from arylene, heteroarylene, alkenylene, and alkynylene, each optionally substituted by 1, 2, 3, or 4 substituents independently selected from halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, CN, $NO_2$, and OH;

W' is independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, $C_{2-50}$ alkoxy, CN, $NO_2$, and OH; and m is 0, 1, or 2;

E is a monocyclic or polycyclic aromatic core;

$R^1$ is each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH;

or $R^1$ is each independently selected from

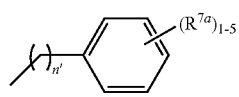 

and wherein $R^{7a}$ and $R^{8a}$ are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH, wherein n' and n" are each 0-50; and y is 2 or 3.

In some embodiments, the compound of Formula (I) have a weight average molecular weight of less than 5,000 (e.g., a weight average molecular weight of less than 4,500; a weight average molecular weight of less than 4,000, a weight average molecular weight of less than 3,500, or a weight average molecular weight of less than 3,000).

In some embodiments, the compound of Formula (II) have a molecular weight of less than 2,000 (e.g., less than 1,500).

In some embodiments, the compound of Formula (III) have a weight average molecular weight of less than 5,000 (e.g., a weight average molecular weight of less than 4,500; or a weight average molecular weight of less than 4,000).

In some embodiments, E is a polycyclic aromatic core.

In some embodiments, E is independently selected from

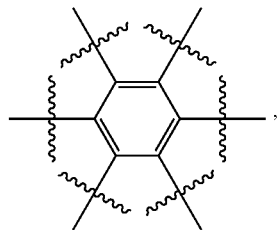

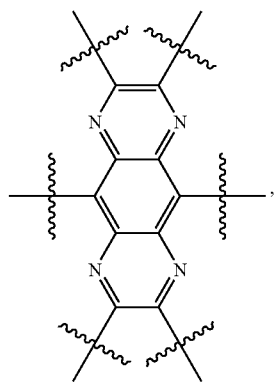

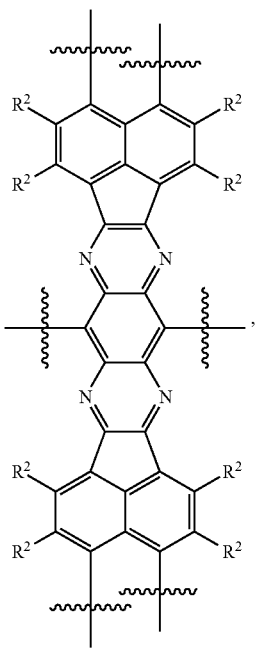

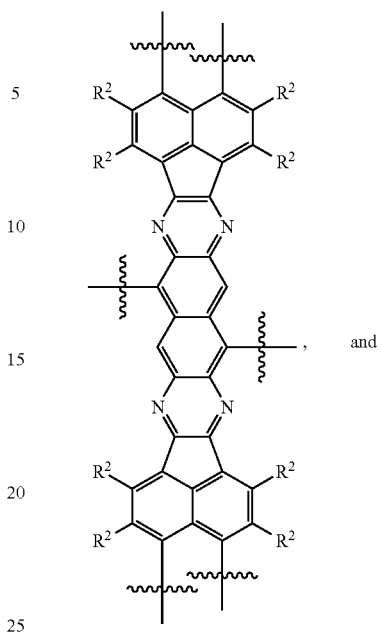

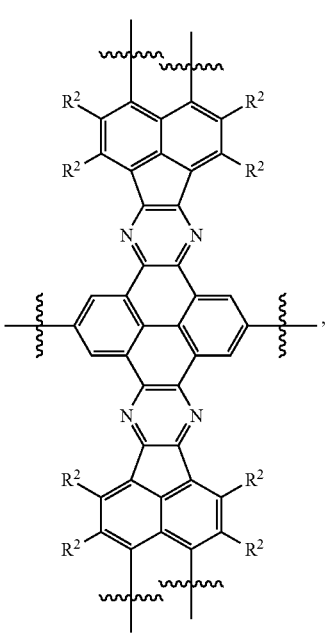

wherein $R^2$ is each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH.

In some embodiments, E is independently selected from
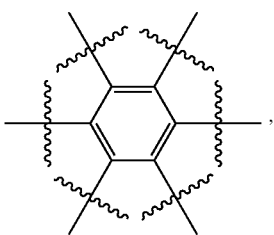
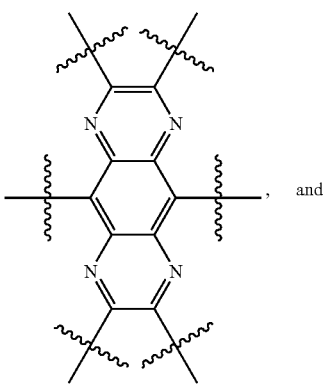, and
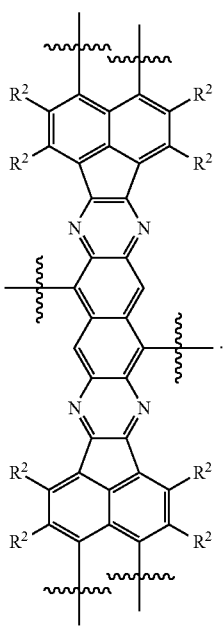.
In some embodiments, E is each independently selected from
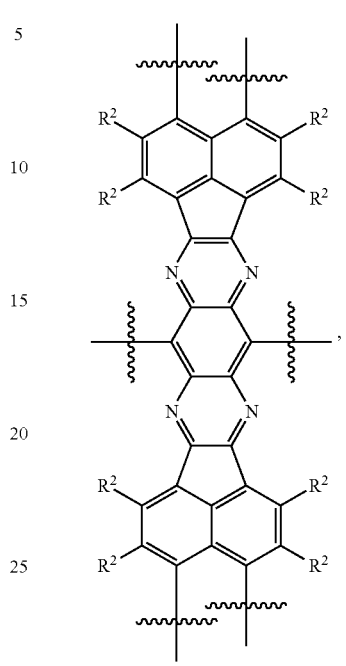,
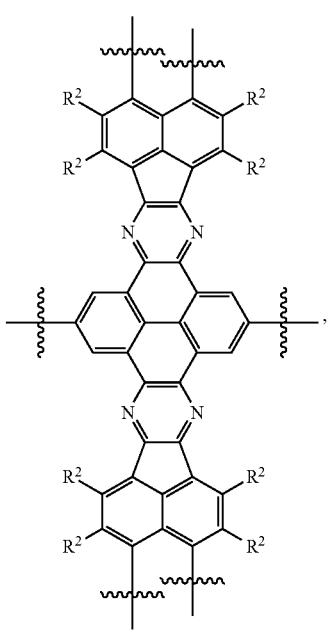, -continued

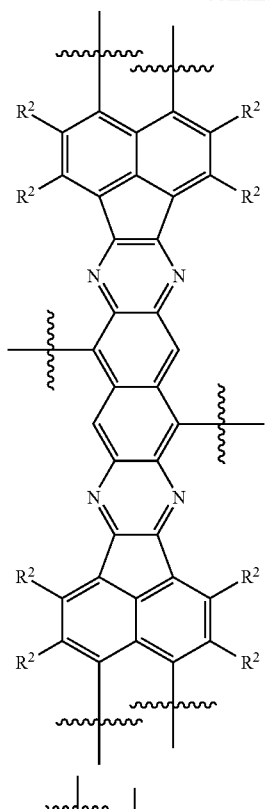

, and

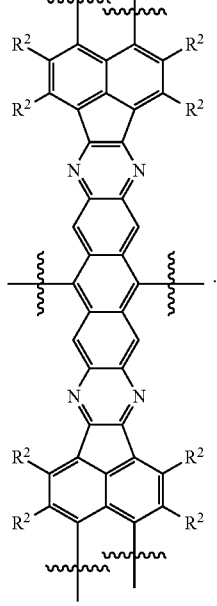

.

wherein R² is each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO₂, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, NO₂, and OH.

In some embodiments, E is

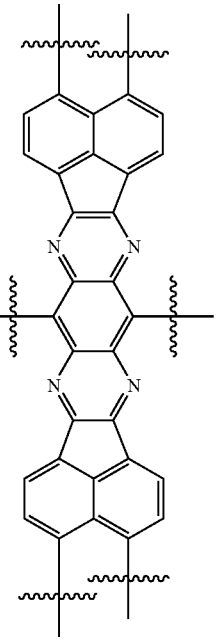

In some embodiments, A¹ is selected from

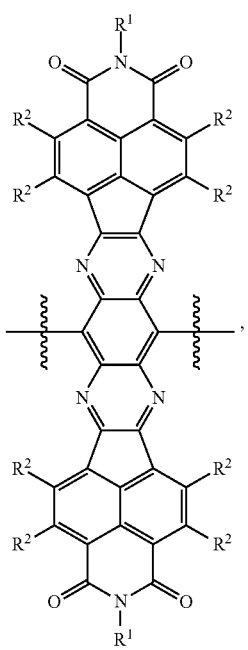

,

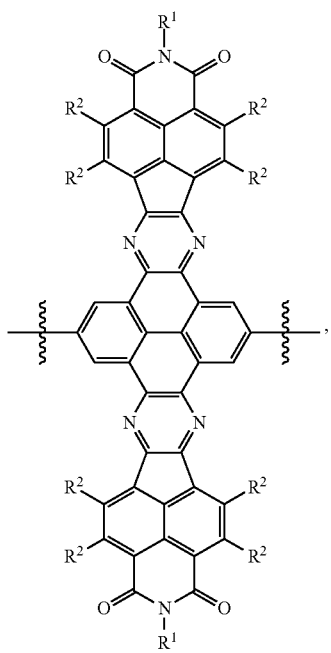
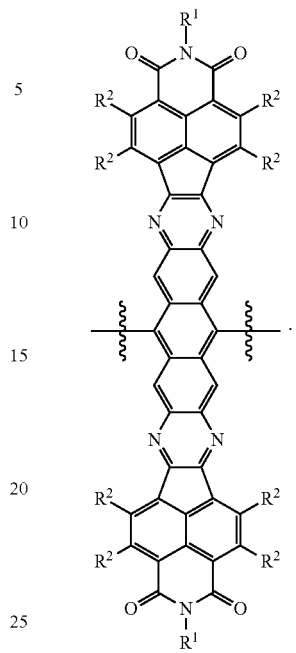
In some embodiments, $A^1$ is selected from
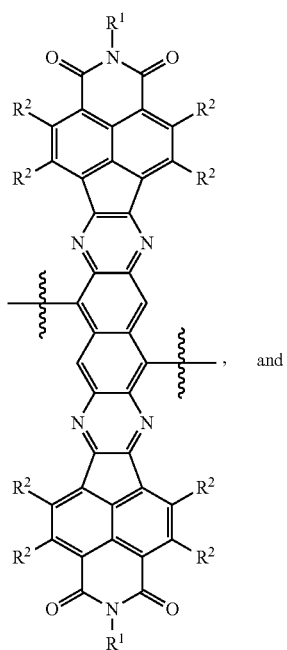, and
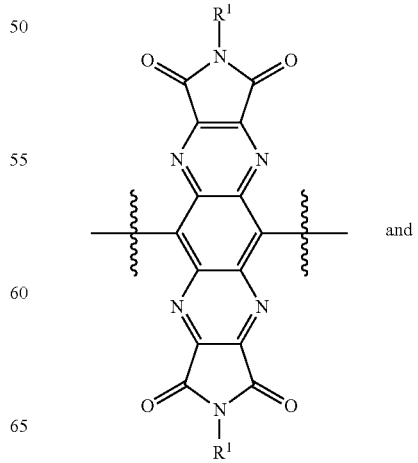 and

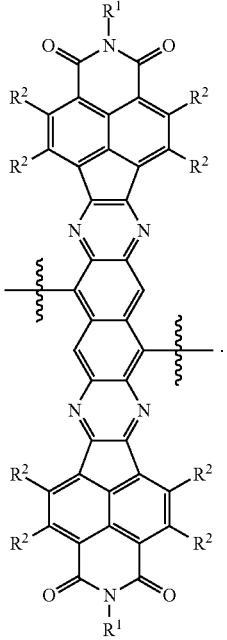

In some embodiments, $A^1$ is

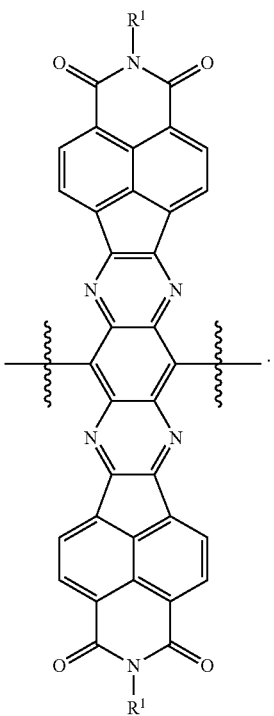

In some embodiments, $R^1$ and $R^2$ are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH.

In some embodiments, $R^1$ and $R^2$ are each independently selected from H, halo, alkyl, alkenyl, alkynyl, alkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH.

In some embodiments, $R^1$ and $R^2$ are each independently selected from H, halo, alkyl, alkenyl, alkynyl, alkoxy, aryl, heteroaryl, cycloalkyl, and heterocycloalkyl, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH.

In some embodiments, $R^1$ and $R^2$ are each independently selected from H, halo, alkyl, alkenyl, alkynyl, and alkoxy, wherein said alkyl, alkenyl, alkynyl, or alkoxy is optionally substituted with 1, 2, 3, 4, or 5 substituents independently selected from halo, $C_{1-50}$ alkyl, $C_{2-50}$ alkenyl, and $C_{2-50}$ alkynyl.

In some embodiments, $R^1$ is each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH In some embodiments, $R^1$ is each independently selected from alkyl, alkenyl, alkynyl, alkoxy, aryl, heteroaryl, cycloalkyl, and heterocycloalkyl, each optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH.

In some embodiments, $R^1$ is independently selected from alkyl, alkenyl, alkynyl, and alkoxy, each optionally substituted with 1, 2, 3, 4, or 5 substituents independently selected from halo, $C_{1-50}$ alkyl, $C_{2-50}$ alkenyl, and $C_{2-50}$ alkynyl.

In some embodiments, $R^1$ is each selected from alkyl, aryl, and heteroaryl, each optionally substituted with 1, 2, 3, 4, or 5 substituents independently selected from halo, alkyl, haloalkyl, alkenyl, haloalkenyl, alkynyl, haloalkynyl, alkoxy, haloalkoxy, aryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is further optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH.

In some embodiments, $R^1$ is each independently selected from

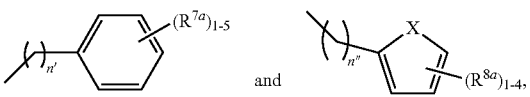

wherein $R^{7a}$ and $R^{8a}$ are each independently selected from H, halo, alkyl, haloalkyl, alkenyl, haloalkenyl, alkynyl, haloalkoxy, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, $NO_2$, and OH, wherein n' and n" are each 0-50.

In some embodiments, $R^1$ is each alkyl optionally substituted with 1, 2, 3, 4, or 5 substituents independently selected from halo, $C_{1-50}$ alkyl, $C_{2-50}$ alkenyl, and $C_{2-50}$ alkynyl.

In some embodiments, $R^1$ is each alkyl (e.g., $C_{1-50}$ alkyl).

In some embodiments, $R^1$ is each a linear alkyl.

In some embodiments, $R^1$ is each a branched alkyl.

In some embodiments, $R^1$ is each independently selected from $(CH_2)CH(C_{10}H_{21})(C_{12}H_{25})$ and $(CH_2)CH(C_4H_9)(C_6H_{13})$.

In some embodiments, $R^1$ is each independently fluoroalkyl (e.g., linear or branched fluoroalkyl).

In some embodiments, $R^1$ is each independently fluoroalkoxy (e.g., linear or branched fluoroalkoxy).

In some embodiments, $R^2$ is each independently alkyl (e.g., $C_{1-50}$ alkyl).

In some embodiments, $R^2$ is each independently a linear alkyl.

In some embodiments, $R^2$ is each independently branched alkyl.

In some embodiments, $R^2$ is each independently fluoroalkyl (e.g., linear or branched fluoroalkyl).

In some embodiments, $R^2$ is each independently fluoroalkoxy (e.g., linear or branched fluoroalkoxy).

In some embodiments, $R^2$ is each independently selected from H, halo, CN, and $NO_2$.

In some embodiments, $R^2$ is H.

In some embodiments, EG and EG' are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, CN, $NO_2$, and OH.

In some embodiments, EG and EG' are each independently selected from H, halo, alkyl, alkenyl, alkynyl, alkoxy, aryl, heteroaryl, cycloalkyl, and heterocycloalkyl, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, CN, $NO_2$, and OH.

In some embodiments, EG and EG' are each independently selected from H, alkyl, alkenyl, alkynyl, alkoxy, aryl, heteroaryl, cycloalkyl, and heterocycloalkyl, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, CN, $NO_2$, and OH.

In some embodiments, EG and EG' are each independently selected from H, halo, alkyl, alkenyl, alkynyl, and alkoxy, wherein said alkyl, alkenyl, alkynyl, or alkoxy is optionally substituted with 1, 2, 3, 4, or 5 substituents independently selected from halo, $C_{1-50}$ alkyl, $C_{2-50}$ alkenyl, and $C_{2-50}$ alkynyl.

In some embodiments, EG and EG' are each independently selected from alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, CN, $NO_2$, and OH.

In some embodiments, EG and EG' are each independently selected from alkyl, alkenyl, alkynyl, alkoxy, aryl, heteroaryl, cycloalkyl, and heterocycloalkyl, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, CN, $NO_2$, and OH.

In some embodiments, EG and EG' are each independently selected from alkyl, alkenyl, alkynyl, and alkoxy, wherein said alkyl, alkenyl, alkynyl, or alkoxy is optionally substituted with 1, 2, 3, 4, or 5 substituents independently selected from halo, $C_{1-50}$ alkyl, $C_{2-50}$ alkenyl, and $C_{2-50}$ alkynyl.

In some embodiments, EG and EG' are each independently selected from aryl and heteroaryl, each optionally substituted with 1, 2, 3, or 4 substituents independently selected from halo, $C_{2-50}$ alkynyl, CN, and $NO_2$.

In some embodiments, EG and EG' are each independently aryl optionally substituted with 1, 2, 3, or 4 substituents independently selected from halo, $C_{1-50}$ alkyl, CN, and $NO_2$.

In some embodiments, EG and EG' are each independently aryl.

In some embodiments, EG and EG' are each independently selected from

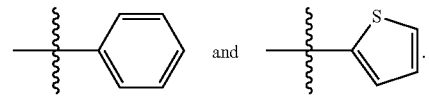

In some embodiments, at least one of EG and EG' is

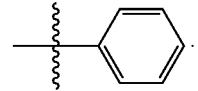

In some embodiments, EG and EG' are each independently alkyl (e.g., $C_{1-50}$ alkyl).

In some embodiments, EG and EG' are each independently a linear alkyl.

In some embodiments, EG and EG' are each independently a branched alkyl.

In some embodiments, EG and EG' are each independently fluoroalkyl (e.g., linear or branched fluoroalkyl).

In some embodiments, EG and EG' are each independently fluoroalkoxy (e.g., linear or branched fluoroalkoxy).

In some embodiments, at least one of EG or EG' is independently selected from aryl, heteroaryl, cycloalkyl, and heterocycloalkyl, each optionally substituted with 1, 2, 3, or 4 substituents independently selected from halo, $C_{1-50}$ alkyl, $C_{2-50}$ alkenyl, $C_{2-50}$ alkynyl, $C_{2-50}$ alkoxy, CN, $NO_2$, and OH.

In some embodiments, at least one of EG or EG' is independently selected from aryl and heteroaryl, each optionally substituted with 1, 2, 3, or 4 substituents independently selected from halo, $C_{1-50}$ alkyl, $C_{2-50}$ alkenyl, $C_{2-50}$ alkynyl, $C_{2-50}$ alkoxy, CN, $NO_2$, and OH.

In some embodiments, at least one of EG or EG' is independently selected from aryl optionally substituted with 1, 2, 3, or 4 substituents independently selected from halo, $C_{1-50}$ alkyl, $C_{2-50}$ alkenyl, $C_{2-50}$ alkynyl, $C_{2-50}$ alkoxy, CN, $NO_2$, and OH.

In some embodiments, at least one of EG or EG' is halo (e.g., bromo).

In some embodiments, at least one of EG or EG' is halo, and the other is aryl.

In some embodiments, EG' is halo. For example, EG' is bromo.

In some embodiments, the compounds of Formula (I), Formula (II), and/or Formula (II) have the following provisos:

EG and EG' are not both H;

EG and EG' are not both halo;

EG and EG' are not both CN;

EG and EG' are not both thiophenyl;

EG and EG' are not both methylthiophenyl; and/or

EG and EG' are not both heteroaryl.

In some embodiments, W is independently selected from:

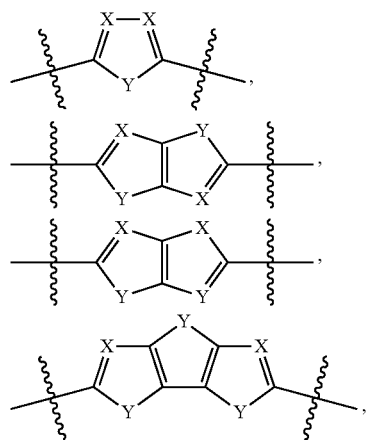

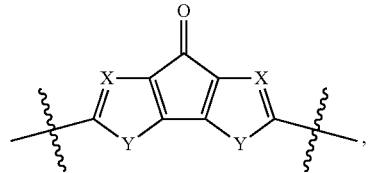

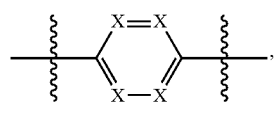, 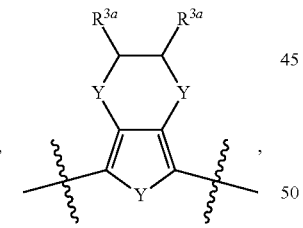,

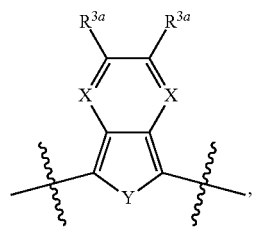, 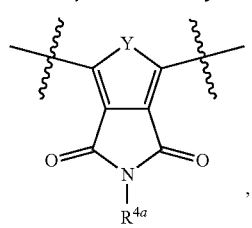,

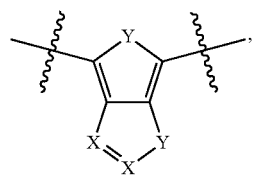, 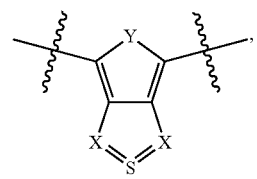,

-continued

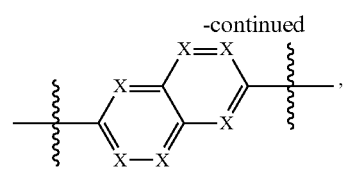,

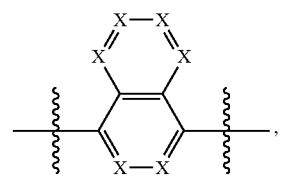,

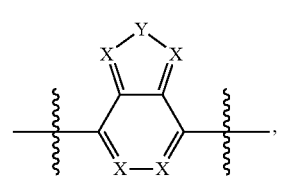,

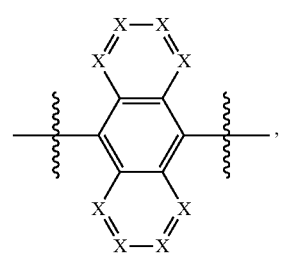,

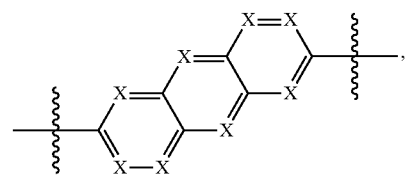,

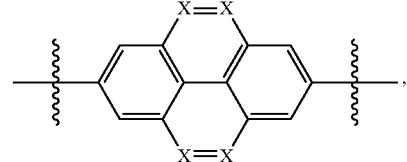,

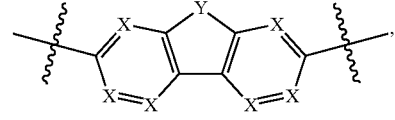,

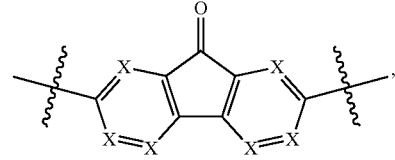,

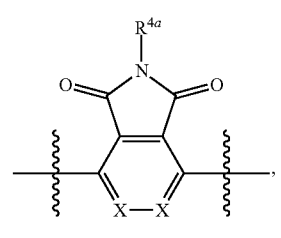, 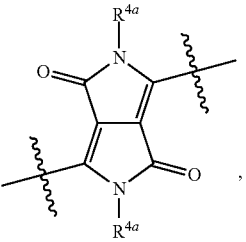,

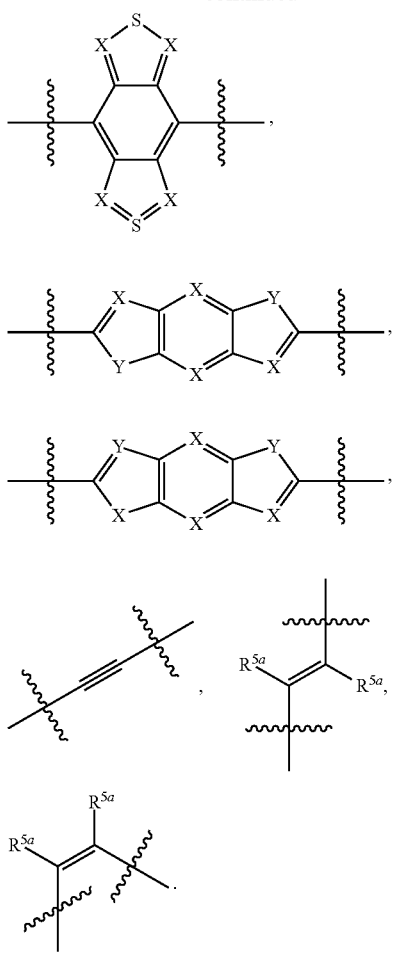
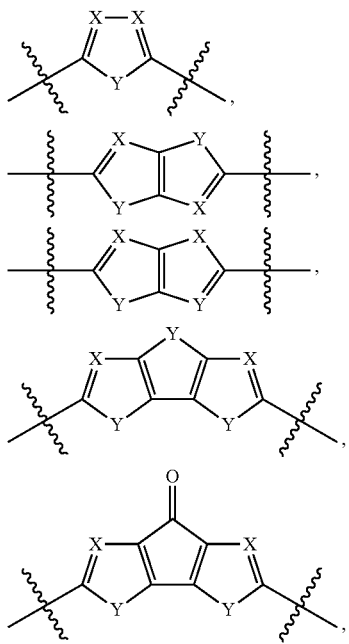
In some embodiments, W is independently selected from
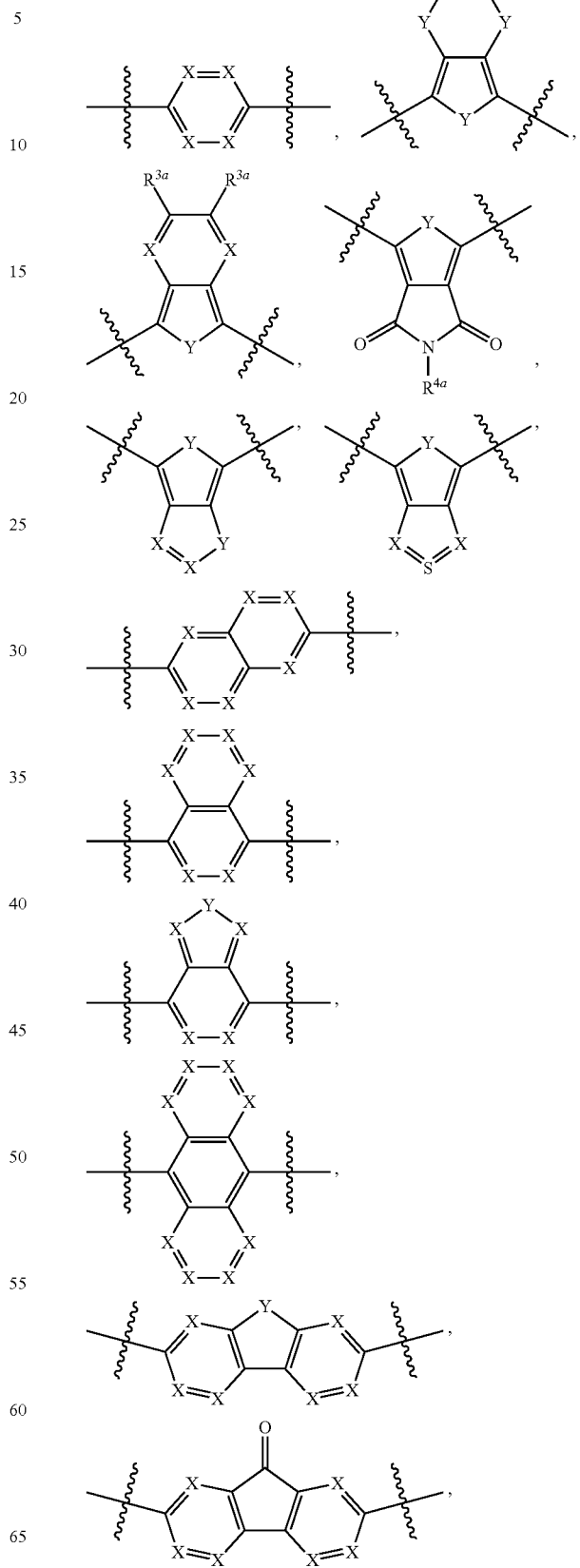

-continued

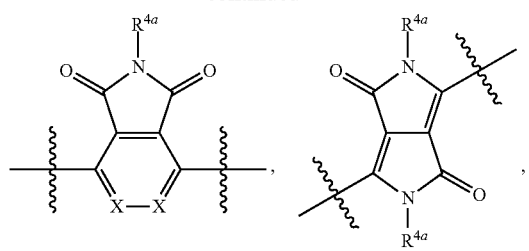

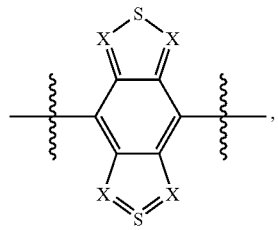

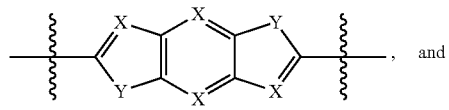, and

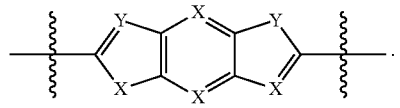.

In some embodiments, W is independently selected from

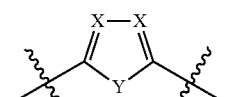,

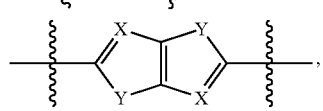,

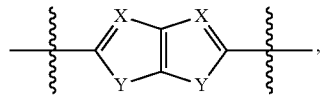,

,

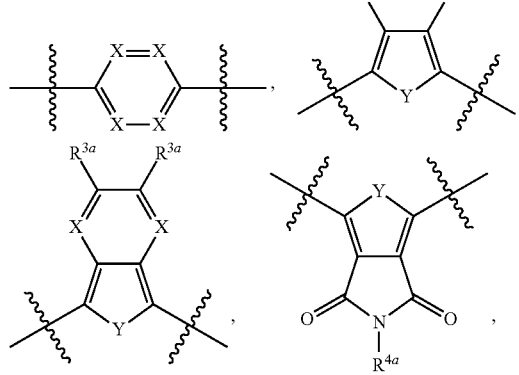,

-continued

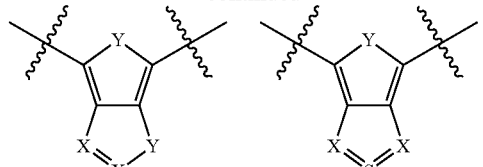,

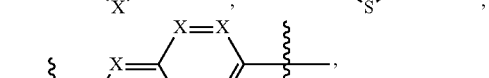,

,

,

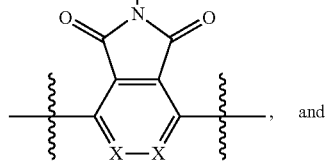, and

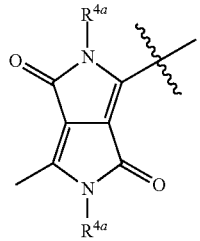.

In some embodiments, W is independently selected from

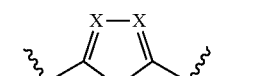 and

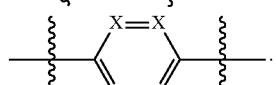.

In some embodiments, Y is independently selected from O, S, $SO_2$, Se, Te, $N(R^{3a})$, $C(R^{3a})_2$, $Si(R^{3a})_2$, and $Ge(R^{3a})_2$.
In some embodiments, Y is independently selected from O, S, $SO_2$, $N(R^{3a})$, and $C(R^{3a})_2$.
In some embodiments, Y is independently selected from O, S, $N(R^{3a})$, and $C(R^{3a})_2$.
In some embodiments, Y is independently selected from O, S, and $C(R^{3a})_2$.
In some embodiments, Y is $C(R^{3a})_2$.
In some embodiments, Y is O.
In some embodiments, Y is S.

In some embodiments, X is independently selected from $CR^{6a}$ and N.

In some embodiments, X is $CR^{6a}$.

In some embodiments, X is N.

In some embodiments, $R^{3a}$, $R^{4a}$, $R^{5a}$, and $R^{6a}$, when present, are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, $C_{2-50}$ alkoxy, CN, $NO_2$, and OH.

In some embodiments, $R^{3a}$, $R^{4a}$, $R^{5a}$, and $R^{6a}$, when present, are each independently selected from H, halo, alkyl, alkenyl, alkynyl, alkoxy, aryl, heteroaryl, cycloalkyl, heterocycloalkyl, CN, $NO_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, $C_{1-50}$ alkyl, $C_{2-50}$ alkenyl, $C_{2-50}$ alkynyl, $C_{2-50}$ alkoxy, CN, $NO_2$, and OH.

In some embodiments, $R^{3a}$, $R^{4a}$, $R^{5a}$, and $R^{6a}$, when present, are each independently selected from H, halo, alkyl, alkenyl, alkynyl, and alkoxy, wherein said alkyl, alkenyl, alkynyl, or alkoxy is optionally substituted with 1, 2, 3, 4, or 5 substituents independently selected from halo, $C_{1-50}$ alkyl, $C_{2-50}$ alkenyl, and $C_{2-50}$ alkynyl.

In some embodiments, $R^{3a}$, $R^{4a}$, $R^{5a}$, and $R^{6a}$, when present, are each independently selected from H and alkyl, wherein said alkyl is optionally substituted with 1, 2, 3, 4, or 5 substituents independently selected from halo, $C_{1-50}$ alkyl, $C_{2-50}$ alkenyl, and $C_{2-50}$ alkynyl.

In some embodiments, W' is independently selected from

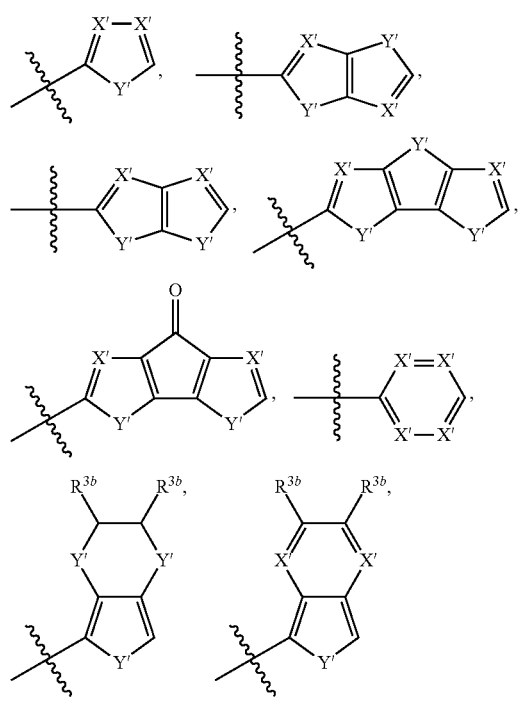

-continued

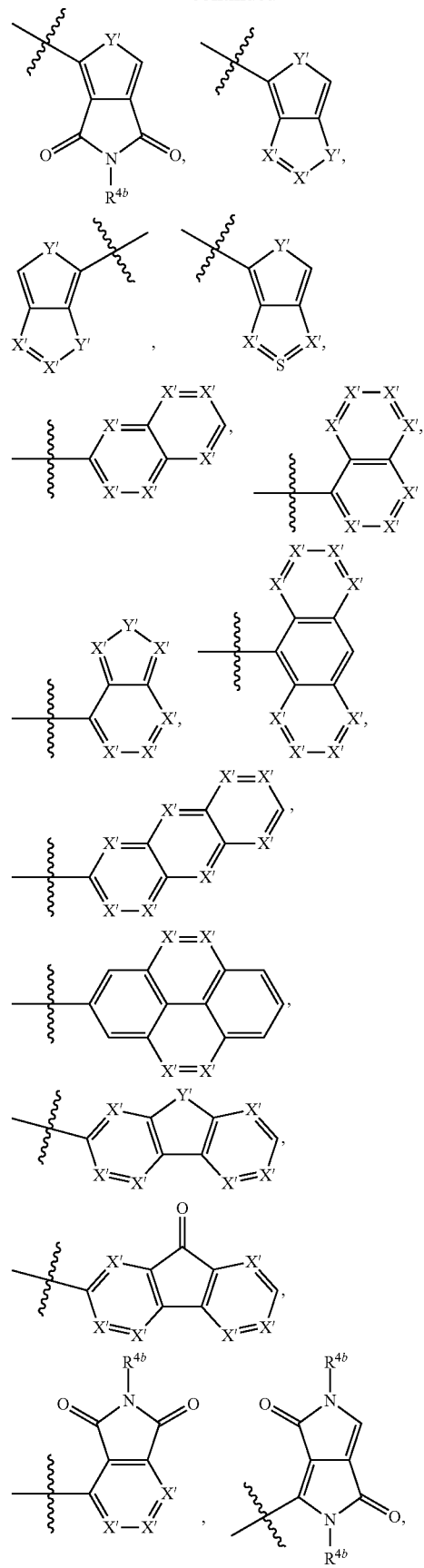

-continued
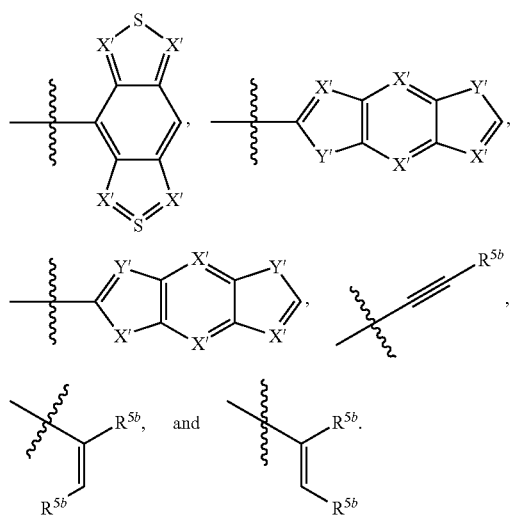
In some embodiments, W' is independently selected from
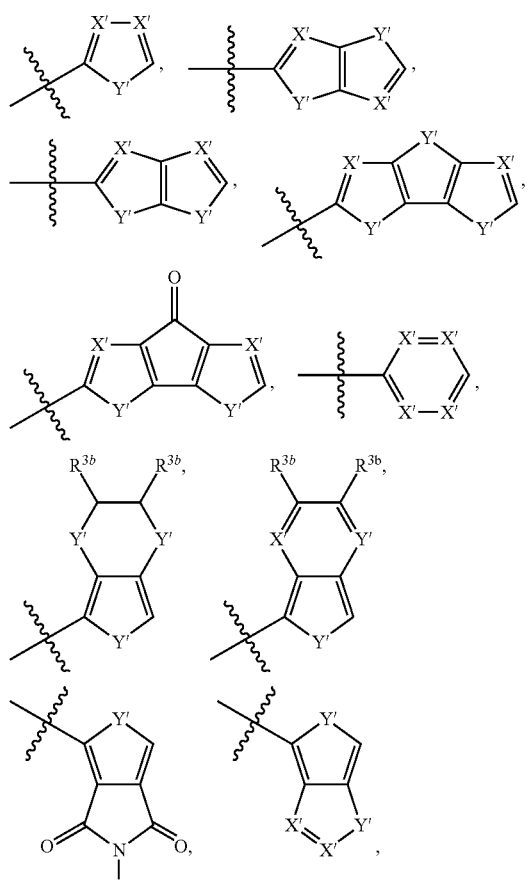
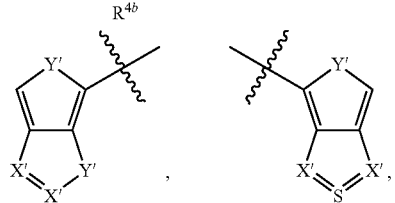
-continued
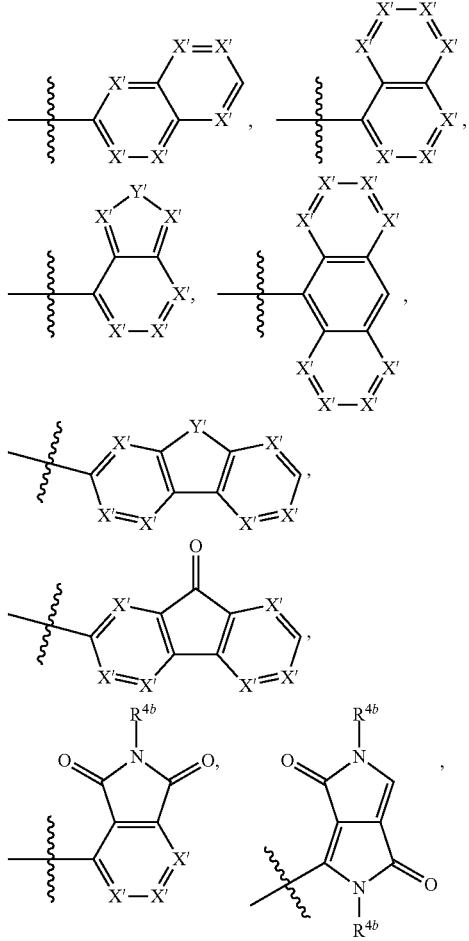
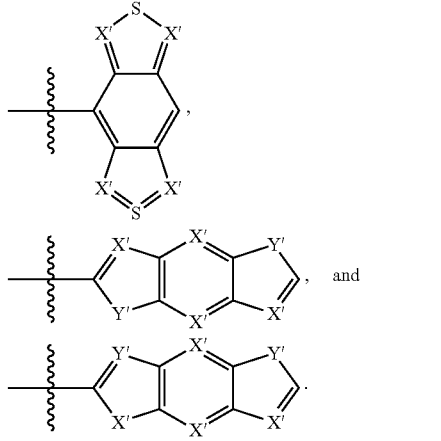
In some embodiments, W' is independently selected from
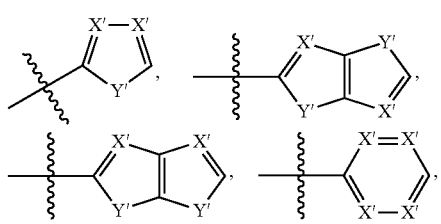

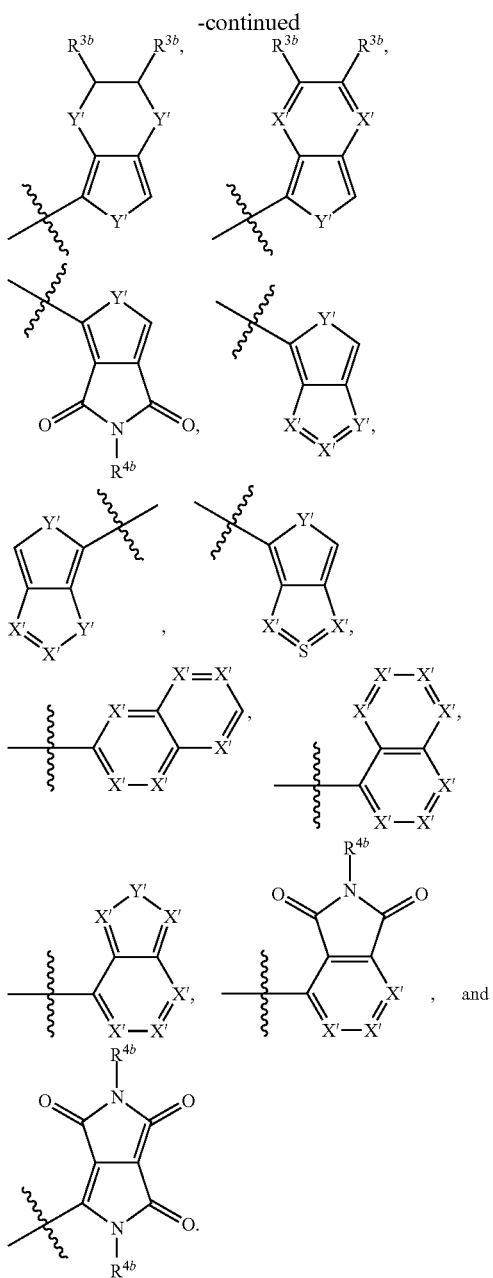

In some embodiments, W' is independently selected from

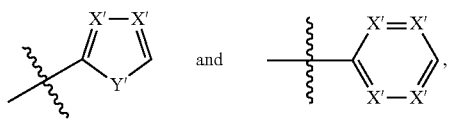

In some embodiments, Y' is independently selected from O, S, SO$_2$, Se, Te, N(R$^{3b}$), C(R$^{3b}$)$_2$, Si(R$^{3b}$)$_2$, and Ge(R$^{3b}$)$_2$.

In some embodiments, Y' is independently selected from O, S, SO$_2$, N(R$^{3b}$), and C(R$^{3b}$)$_2$.

In some embodiments, Y' is independently selected from O, S, N(R$^{3b}$), and C(R$^{3b}$)$_2$.

In some embodiments, Y' is independently selected from O, S, and C(R$^{3b}$)$_2$.

In some embodiments, Y' is C(R$^{3b}$)$_2$.

In some embodiments, Y' is O.

In some embodiments, Y' is S.

In some embodiments, X' is independently selected from CR$^{6b}$ and N.

In some embodiments, X' is CR$^{6b}$.

In some embodiments, X' is N.

In some embodiments, R$^{3b}$, R$^{4b}$, R$^{5b}$, and R$^{6b}$, when present, are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

In some embodiments, R$^{3b}$, R$^{4b}$, R$^{5b}$, and R$^{6b}$, when present, are each independently selected from H, halo, alkyl, alkenyl, alkynyl, alkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

In some embodiments, R$^{3b}$, R$^{4b}$, R$^{5b}$, and R$^{6b}$, when present, are each independently selected from H, halo, alkyl, alkenyl, alkynyl, and alkoxy, wherein said alkyl, alkenyl, alkynyl, or alkoxy is optionally substituted with 1, 2, 3, 4, or 5 substituents independently selected from halo, C$_{1-50}$ alkyl, C$_{2-50}$ alkenyl, and C$_{2-50}$ alkynyl.

In some embodiments, R$^{3b}$, R$^{4b}$, R$^{5b}$, and R$^{6b}$, when present, are each independently selected from H and alkyl, wherein said alkyl is optionally substituted with 1, 2, 3, 4, or 5 substituents independently selected from halo, C$_{1-50}$ alkyl, C$_{2-50}$ alkenyl, and C$_{2-50}$ alkynyl.

In some embodiments, Ar$^1$ is absent.

In some embodiments, Ar$^1$ is arylene or heteroarylene each optionally substituted by 1, 2, 3, or 4 substituents independently selected from halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

In some embodiments, Ar$^1$ is ethynylene or ethenylene, wherein said ethenylene is optionally substituted by 1 or 2 substituents independently selected from halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

In some embodiments, Ar$^1$ is independently selected from

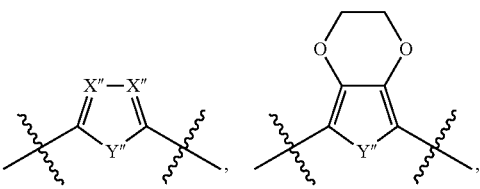

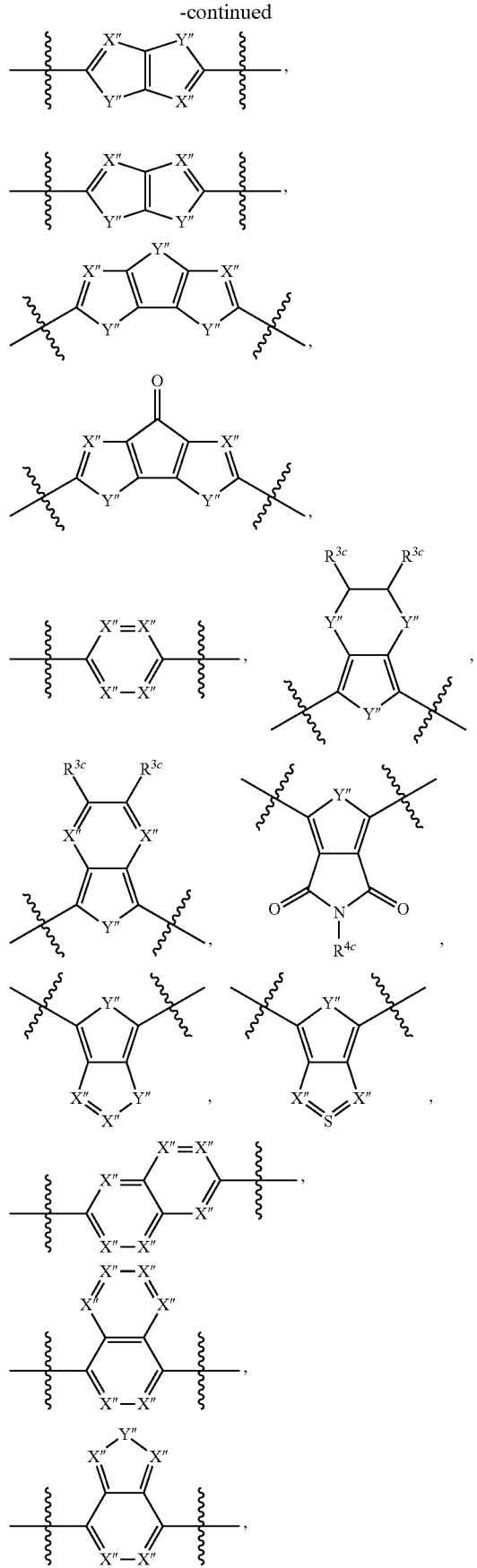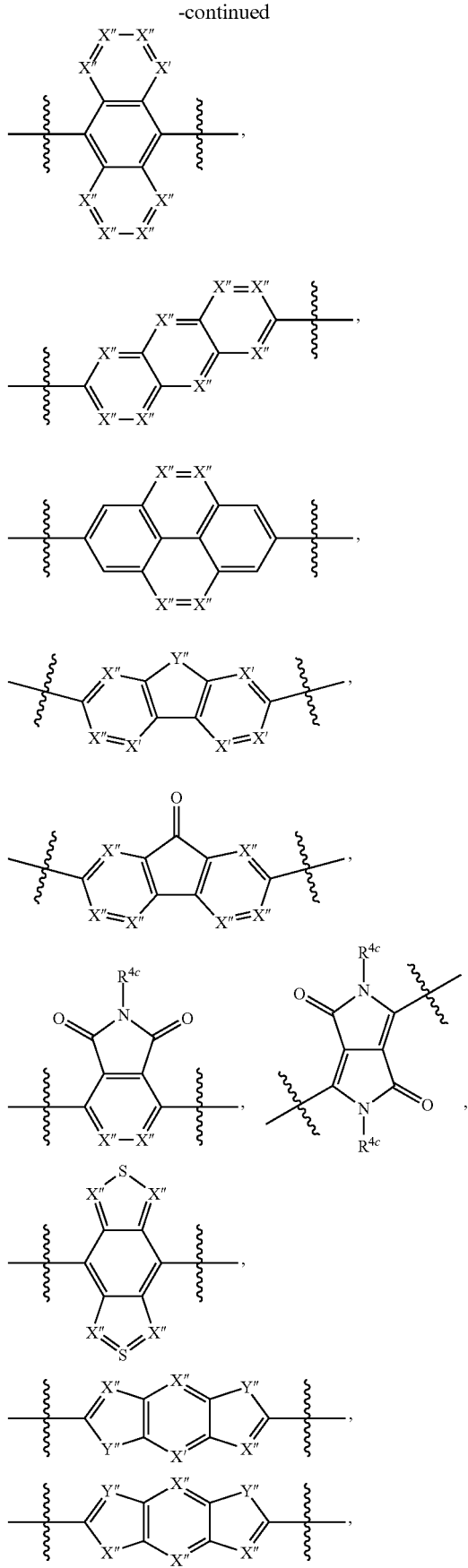

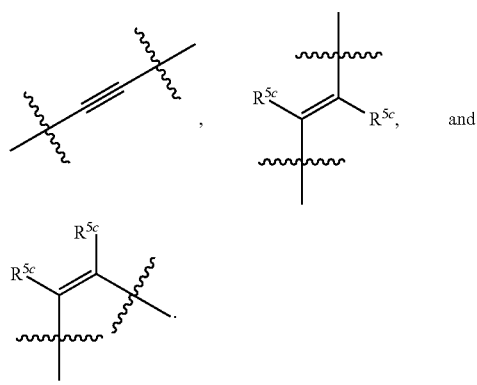
In some embodiments, Ar¹ is independently selected from
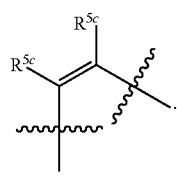
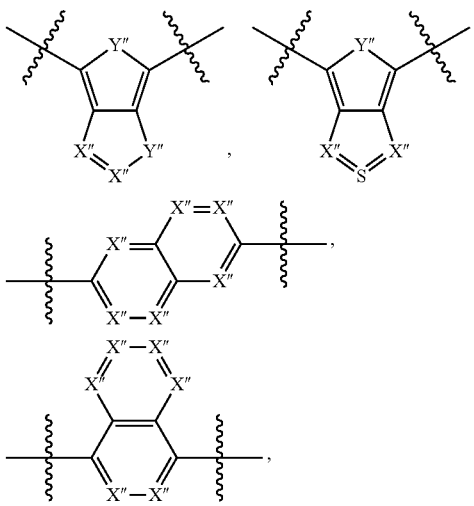
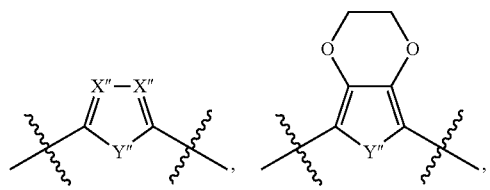
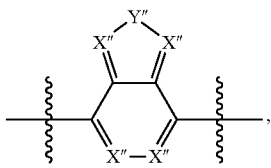
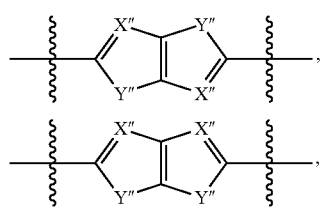
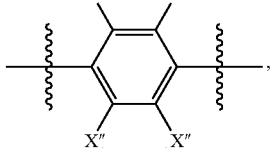
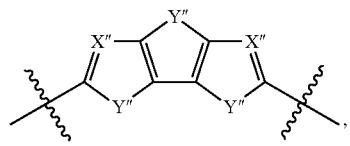
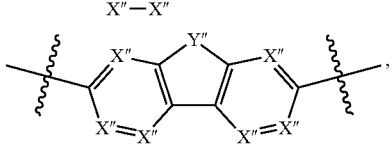
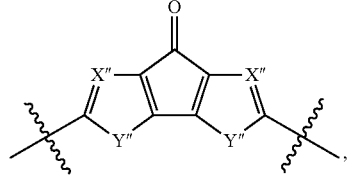
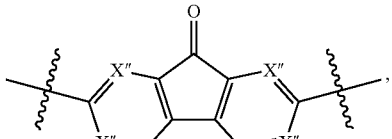
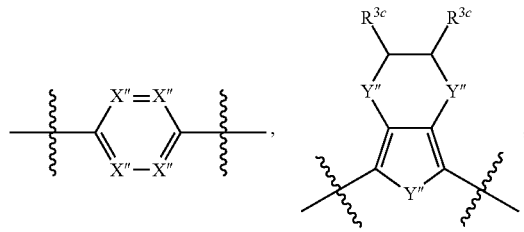
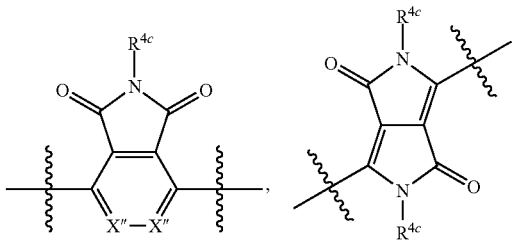
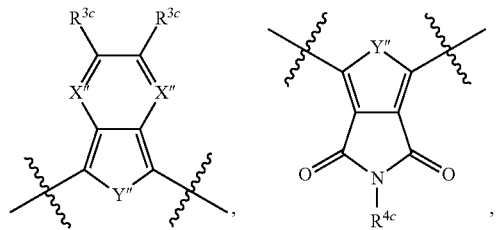
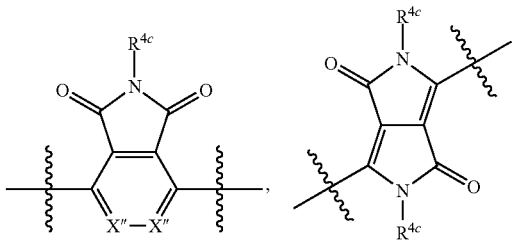
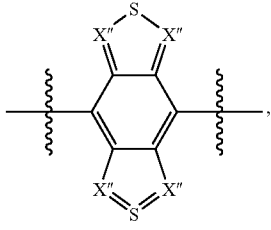

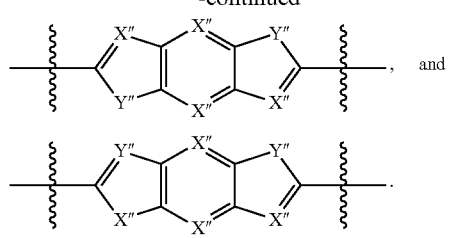, and

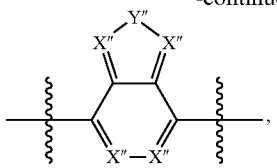,

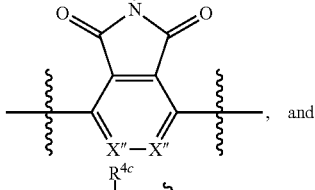, and

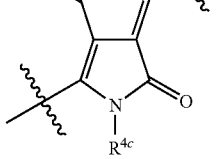

In some embodiments, Ar¹ is independently selected from

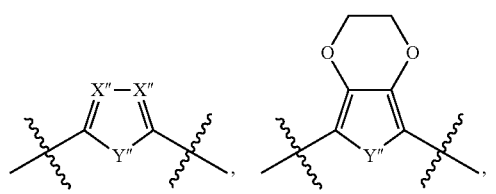,

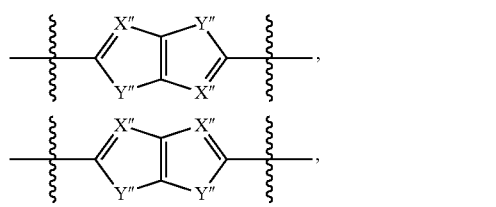,

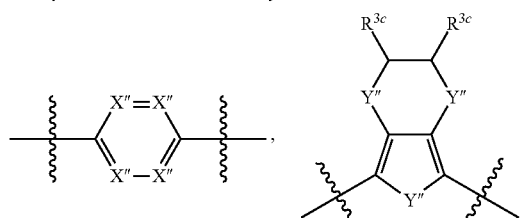,

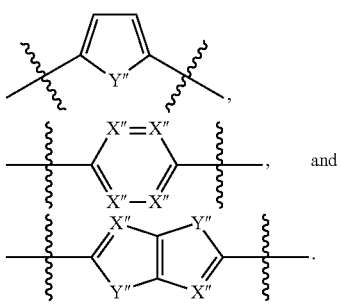

In some embodiments, Ar¹ is independently selected from

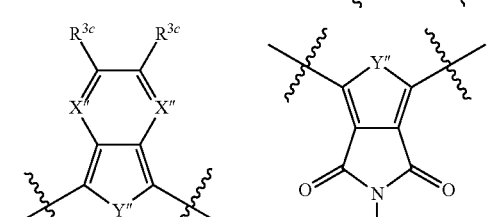,

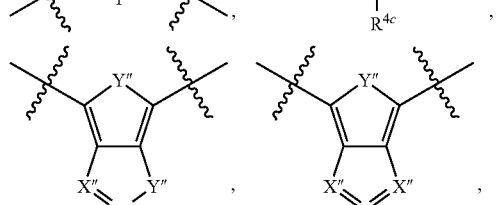,

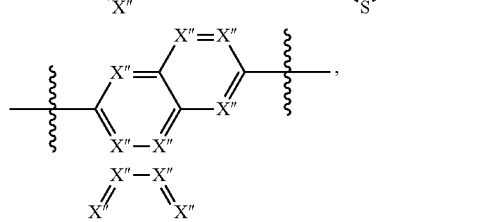,

In some embodiments, Ar¹ is

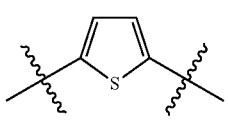 [SMILES: *c1ccc(*)s1]

In some embodiments, Y" is independently selected from O, S, SO₂, Se, Te, $N(R^{3c})$, $C(R^{3c})_2$, $Si(R^{3c})_2$, and $Ge(R^{3c})_2$.

In some embodiments, Y" is independently selected from O, S, SO₂, $N(R^{3c})$, and $C(R^{3c})_2$.

In some embodiments, Y" is independently selected from O, S, $N(R^{3c})$, and $C(R^{3c})_2$.

In some embodiments, Y" is independently selected from O, S, and $C(R^{3c})_2$.

In some embodiments, Y" is $C(R^{3c})_2$.

In some embodiments, Y" is O.

In some embodiments, Y" is S.

In some embodiments, X" is independently selected from $CR^{6c}$ and N.

In some embodiments, X" is $CR^{6c}$.

In some embodiments, X" is N.

In some embodiments, $R^{3c}$, $R^{4c}$, $R^{5c}$, and $R^{6c}$, when present, are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

In some embodiments, R$^{3c}$, R$^{4c}$, R$^{5c}$, and R$^{6c}$, when present, are each independently selected from H, halo, alkyl, alkenyl, alkynyl, alkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

In some embodiments, R$^{3c}$, R$^{4c}$, R$^{5c}$, and R$^{6c}$, when present, are each independently selected from H, halo, alkyl, alkenyl, alkynyl, and alkoxy, wherein said alkyl, alkenyl, alkynyl, or alkoxy is optionally substituted with 1, 2, 3, 4, or 5 substituents independently selected from halo, C$_{1-50}$ alkyl, C$_{2-50}$ alkenyl, and C$_{2-50}$ alkynyl.

In some embodiments, R$^{3c}$, R$^{4c}$, R$^{5c}$, and R$^{6c}$, when present, are each independently selected from H and alkyl, wherein said alkyl is optionally substituted with 1, 2, 3, 4, or 5 substituents independently selected from halo, C$_{1-50}$ alkyl, C$_{2-50}$ alkenyl, and C$_{2-50}$ alkynyl.

In some embodiments, R$^{3a}$, R$^{4a}$, R$^{5a}$, R$^{6a}$, R$^{3b}$, R$^{4b}$, R$^{5b}$, R$^{6b}$, R$^{3c}$, R$^{4c}$, R$^{5c}$, and R$^{6c}$, when present, are each independently selected from H, halo, alkyl, alkenyl, alkynyl, alkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

In some embodiments, R$^{3a}$, R$^{4a}$, R$^{5a}$, R$^{6a}$, R$^{3b}$, R$^{4b}$, R$^{5b}$, R$^{6b}$, R$^{3c}$, R$^{4c}$, R$^{5c}$, and R$^{6c}$, when present, are each independently selected from H, halo, alkyl, alkenyl, alkynyl, alkoxy, aryl, heteroaryl, cycloalkyl, and heterocycloalkyl, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

In some embodiments, R$^{3a}$, R$^{4a}$, R$^{5a}$, R$^{6a}$, R$^{3b}$, R$^{4b}$, R$^{5b}$, R$^{6b}$, R$^{3c}$, R$^{4c}$, R$^{5c}$, and R$^{6c}$, when present, are each independently selected from H, halo, alkyl, alkenyl, alkynyl, and alkoxy, wherein said alkyl, alkenyl, alkynyl, or alkoxy is optionally substituted with 1, 2, 3, or 4 substituents independently selected from halo, C$_{1-50}$ alkyl, C$_{2-50}$ alkenyl, and C$_{2-50}$ alkynyl.

In some embodiments, R$^{6a}$, R$^{6b}$, and R$^{6c}$, when present, are each independently selected from H, halo, CN, and NO$_2$.

In some embodiments, R$^{6a}$, R$^{6b}$, and R$^{6c}$, when present, are each independently selected from H and alkyl.

In some embodiments, R$^{6a}$, R$^{6b}$, and R$^{6c}$, when present, are each H.

In some embodiments, R$^{6c}$ is selected from H, halo, CN, and NO$_2$.

In some embodiments, R$^{7a}$ and R$^{8a}$, when present, are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

In some embodiments, R$^{7a}$ and R$^{8a}$, when present, are each independently selected from H, halo, alkyl, alkenyl, alkynyl, alkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

In some embodiments, R$^{7a}$ and R$^{8a}$, when present, are each independently selected from H, halo, alkyl, alkenyl, alkynyl, and alkoxy, wherein said alkyl, alkenyl, alkynyl, or alkoxy is optionally substituted with 1, 2, 3, 4, or 5 substituents independently selected from halo, C$_{1-50}$ alkyl, C$_{2-50}$ alkenyl, and C$_{2-50}$ alkynyl.

In some embodiments, R$^{7a}$ and R$^{8a}$, when present, are each independently selected from H and alkyl, wherein said alkyl is optionally substituted with 1, 2, 3, 4, or 5 substituents independently selected from halo, C$_{1-50}$ alkyl, C$_{2-50}$ alkenyl, and C$_{2-50}$ alkynyl.

In some embodiments, R$^{7a}$ and R$^{8a}$, when present, are each alkyl optionally substituted with 1, 2, 3, 4, or 5 substituents independently selected from halo, C$_{1-50}$ alkyl, C$_{2-50}$ alkenyl, and C$_{2-50}$ alkynyl.

In some embodiments, x is 1, 2, or 3. In some embodiments, x is 1 or 2. For example, x is 1. As another example, x is 2. As yet another example, x is 3.

In some embodiments, y is 2, 3 or 4. In some embodiments, y is 2 or 3. For example, y is 2. As another example, y is 3. As yet another example, y is 4.

In some embodiments, n' is 0 to 24, 0 to 12, 0 to 6, 0 to 3, 1 to 24, 1 to 12, 1 to 6, or 1 to 3. In some embodiments, n' is 1, 2, 3, 4, 5, or 6.

In some embodiments, n" is 0 to 24, 0 to 12, 0 to 6, 0 to 3, 1 to 24, 1 to 12, 1 to 6, or 1 to 3. In some embodiments, n" is 1, 2, 3, 4, 5, or 6.

In some embodiments, the compound of Formula (I) is selected from

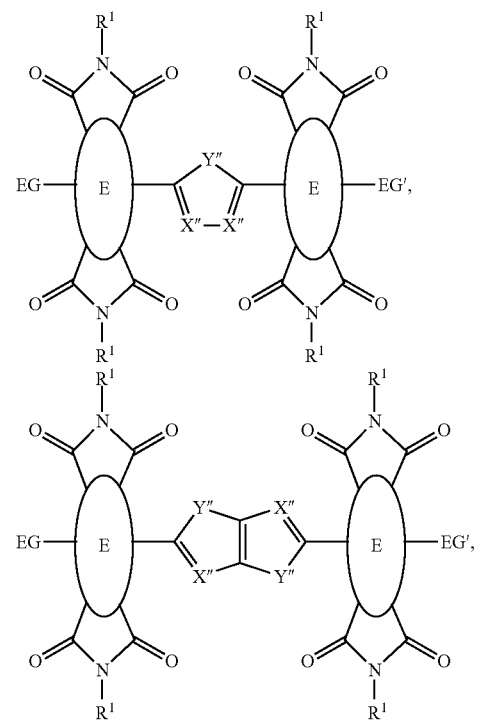

-continued
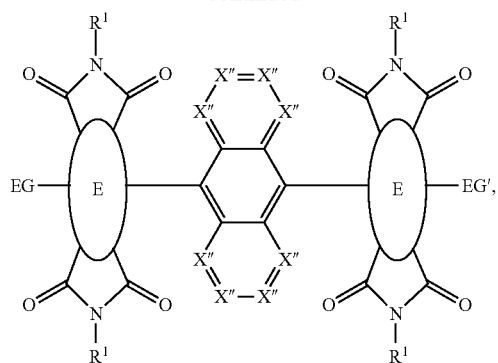
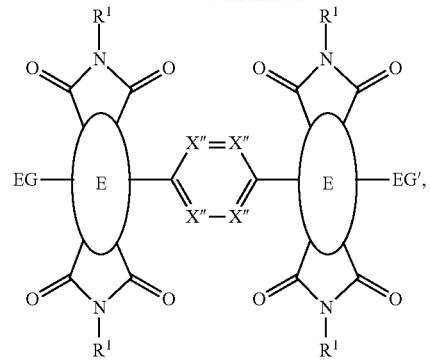
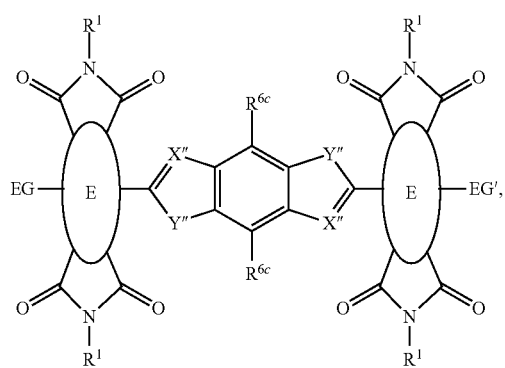
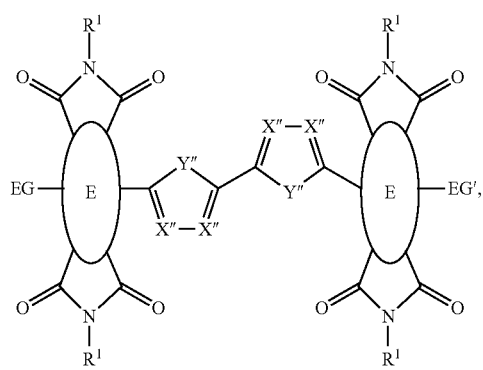
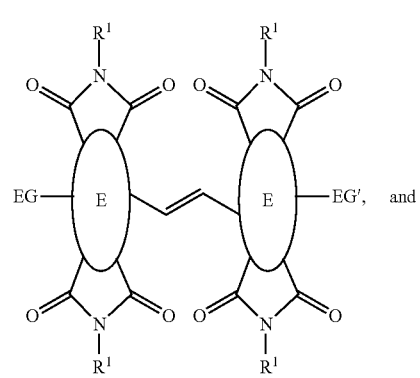
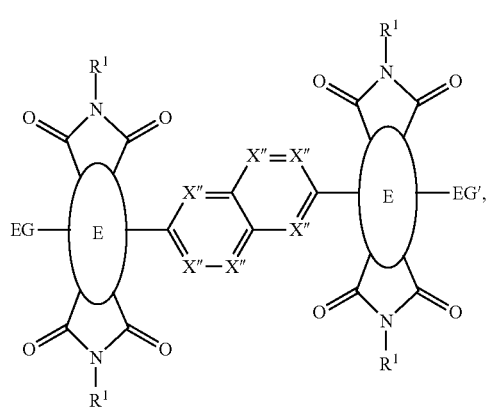
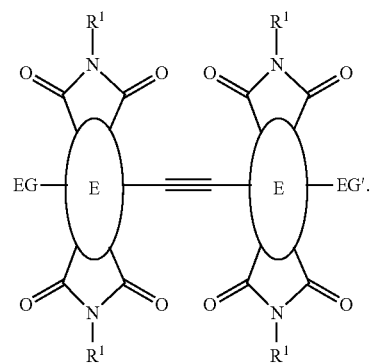
In some embodiments, the compound of Formula (I) is selected from 51
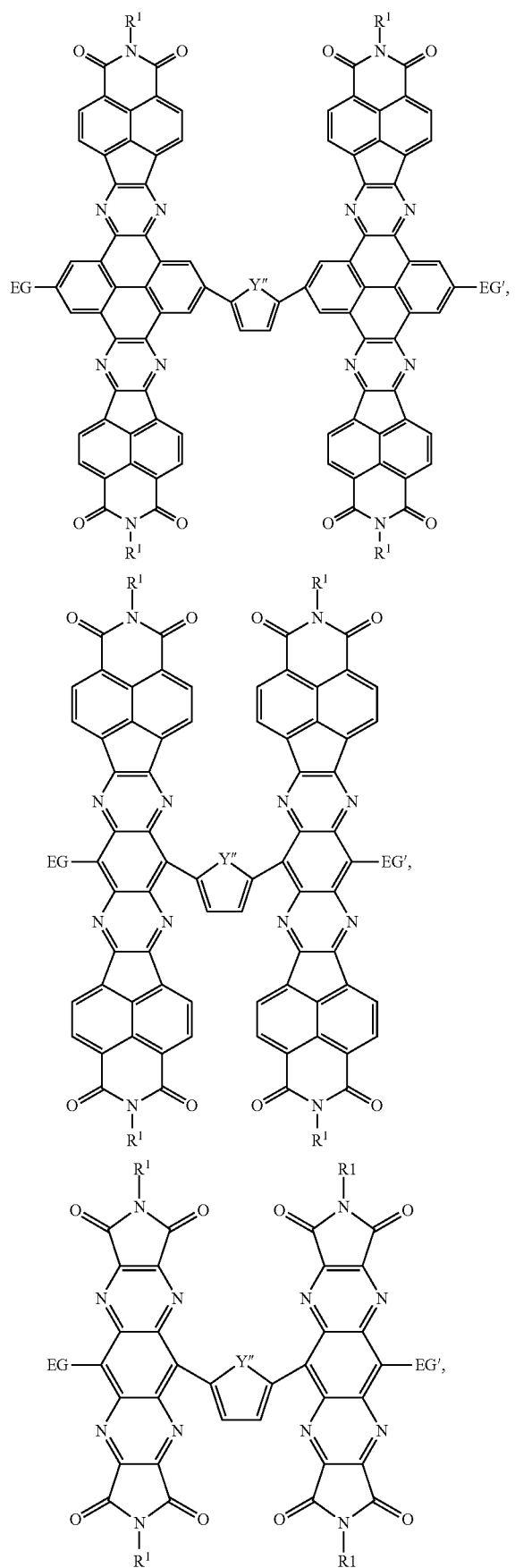
52
-continued
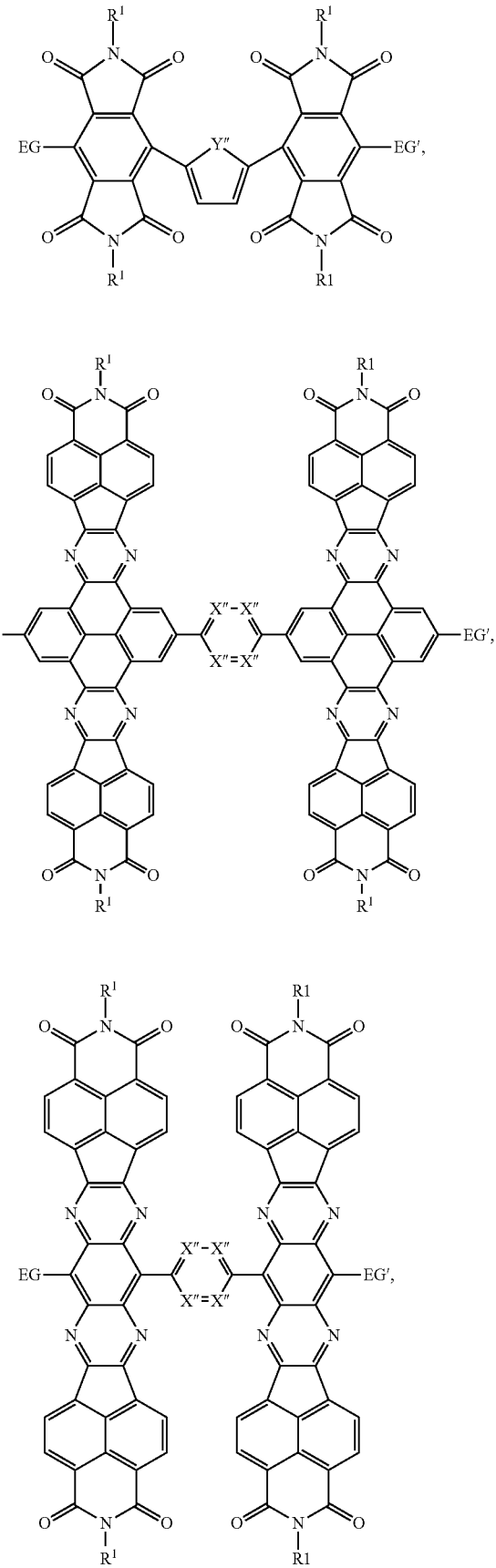

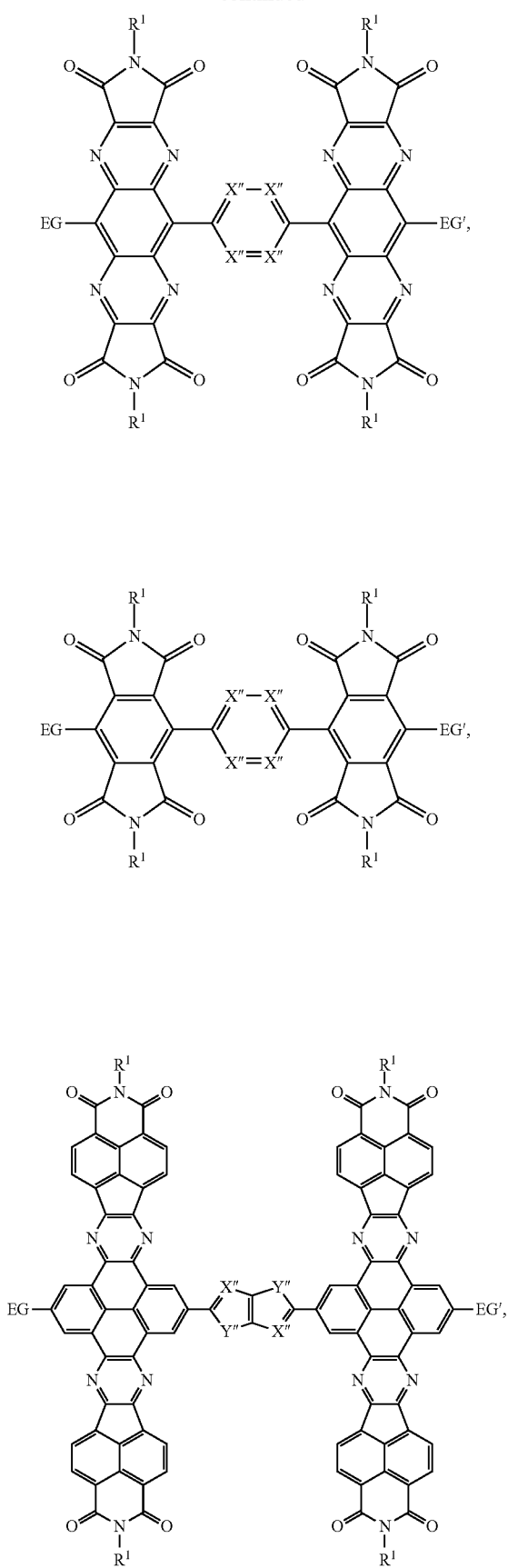
In some embodiments, the compound of Formula (I) is selected from

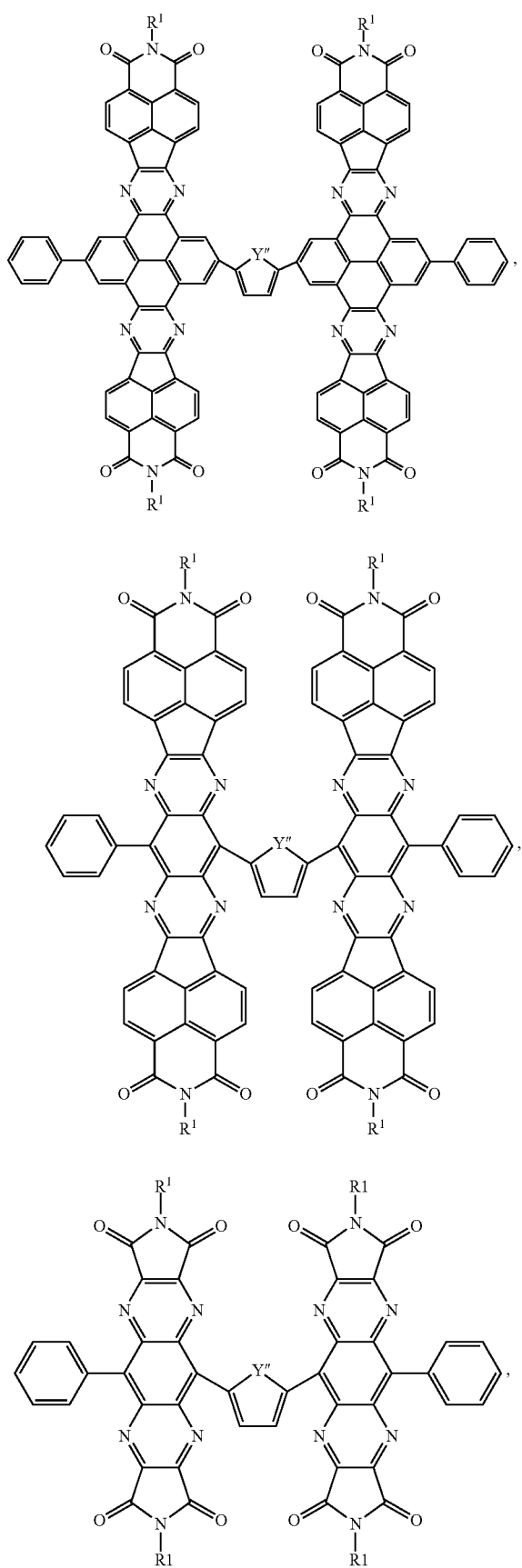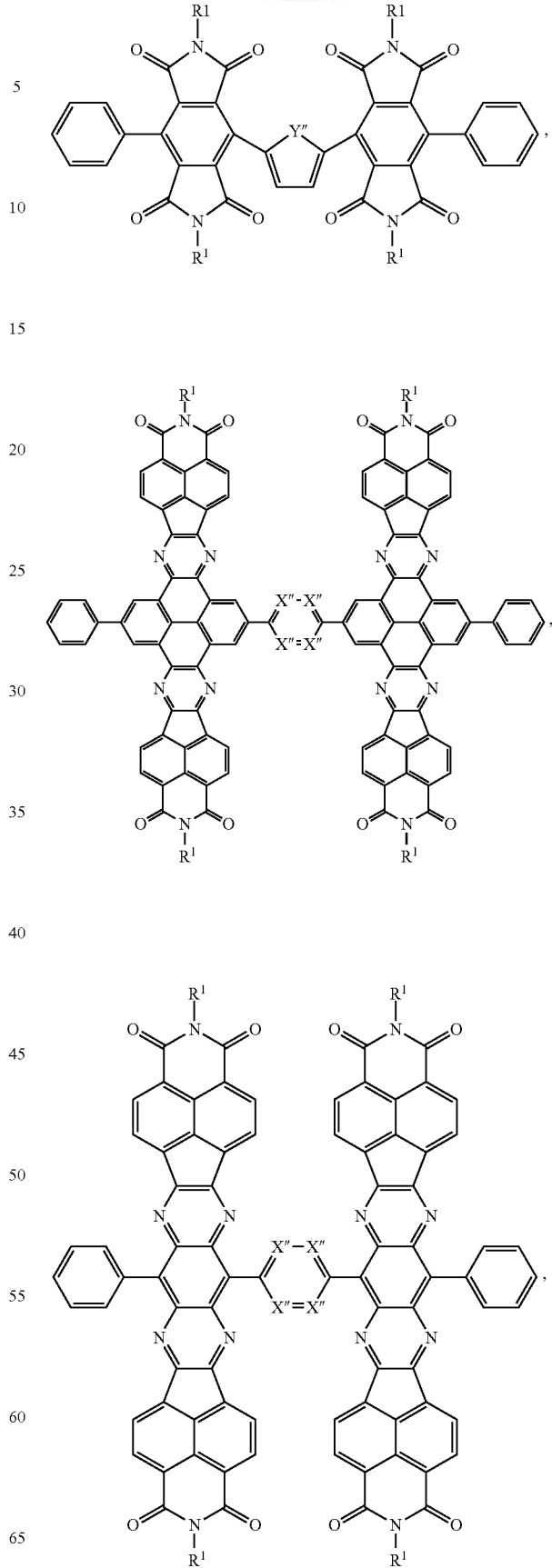

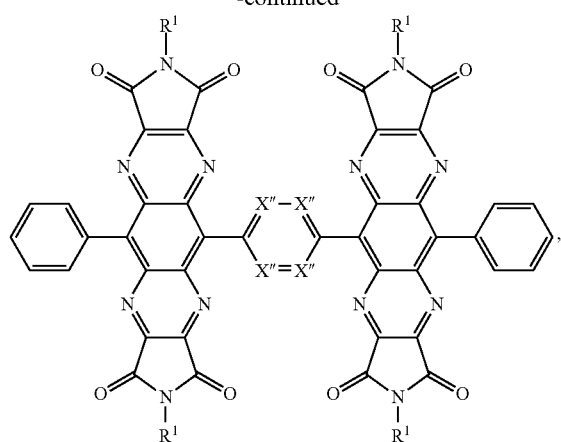
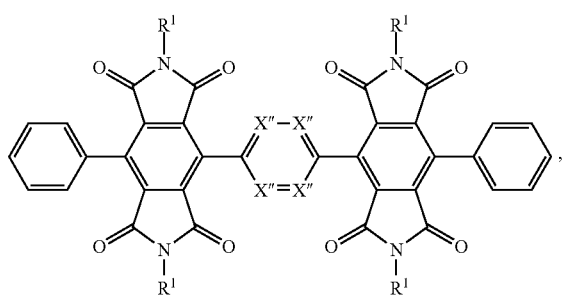
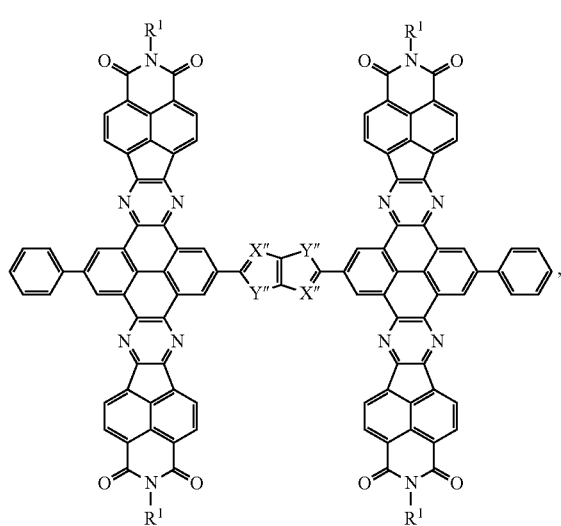
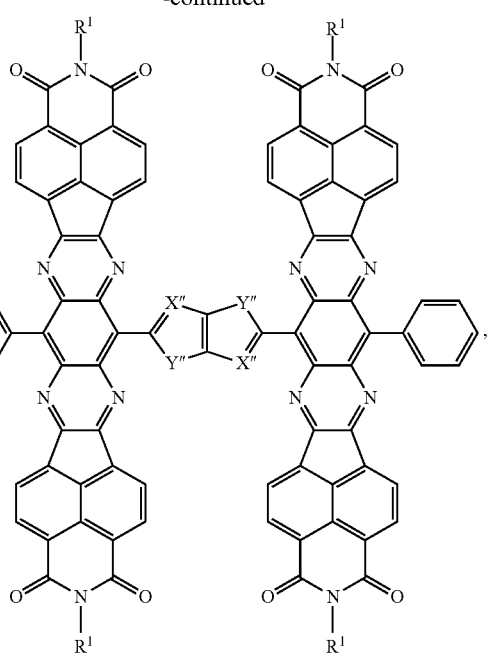
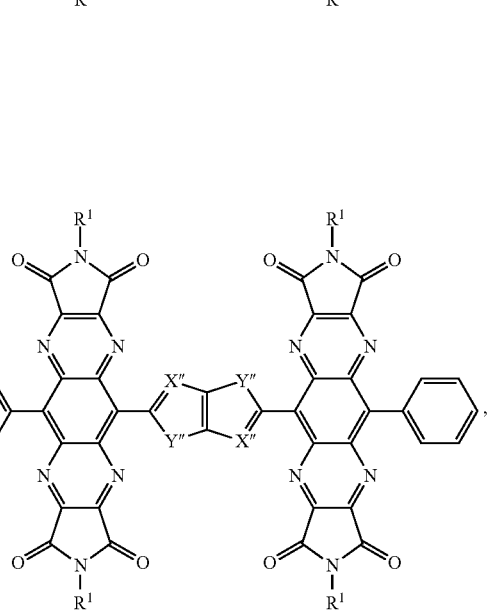
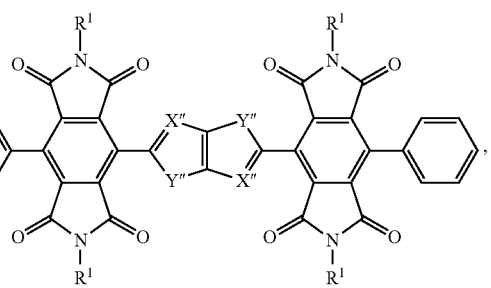

59
-continued
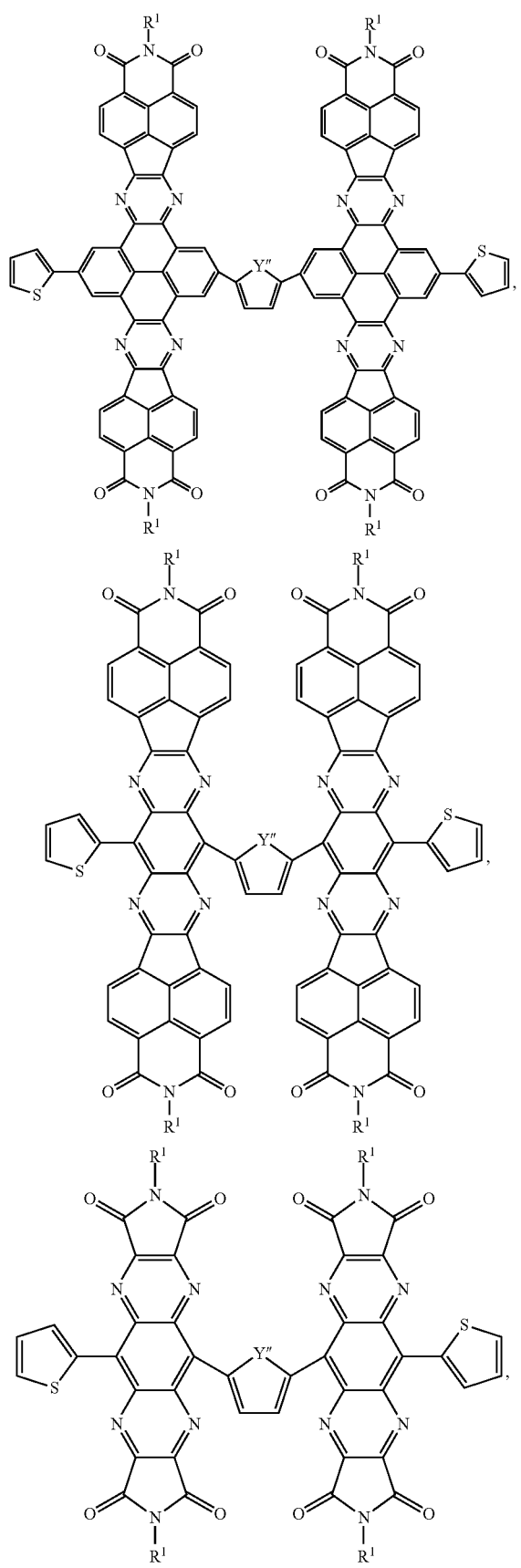
60
-continued
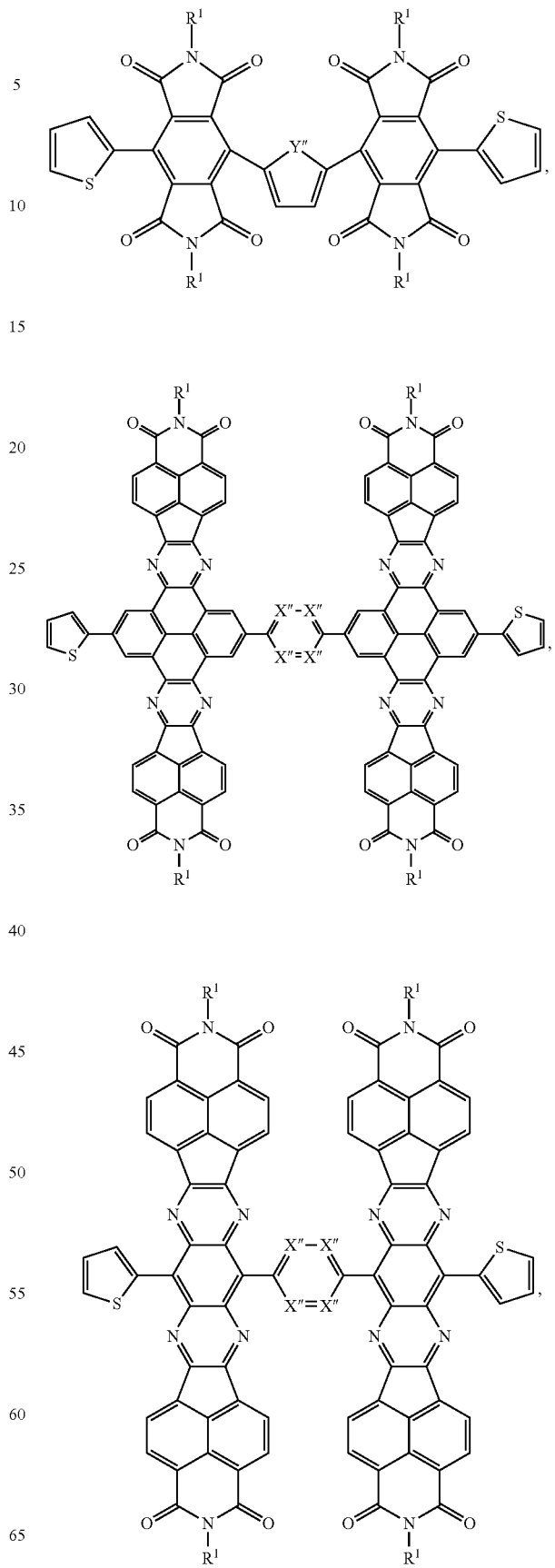

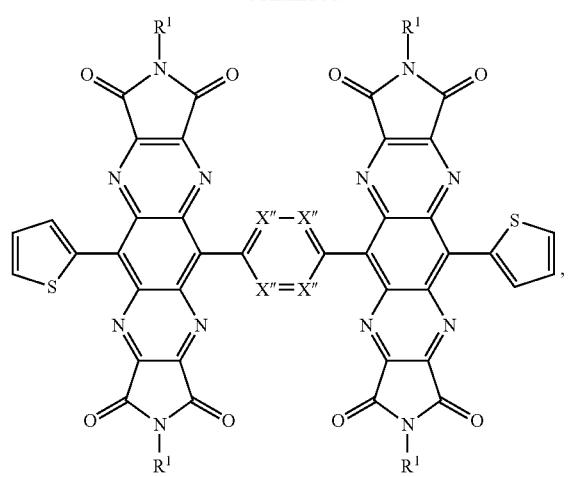
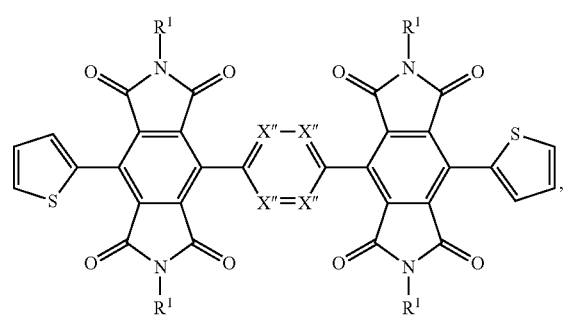
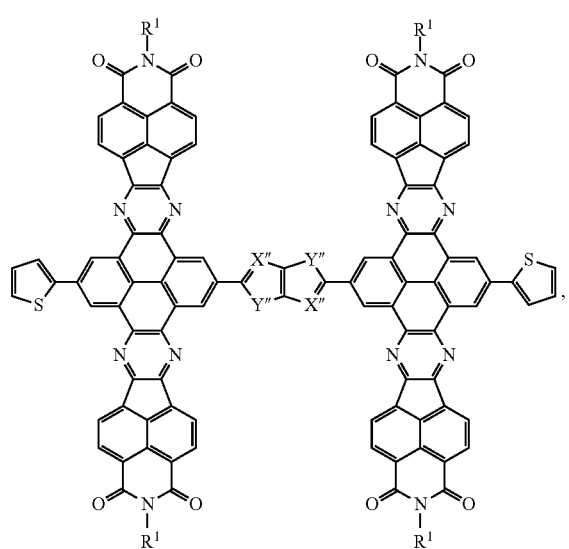
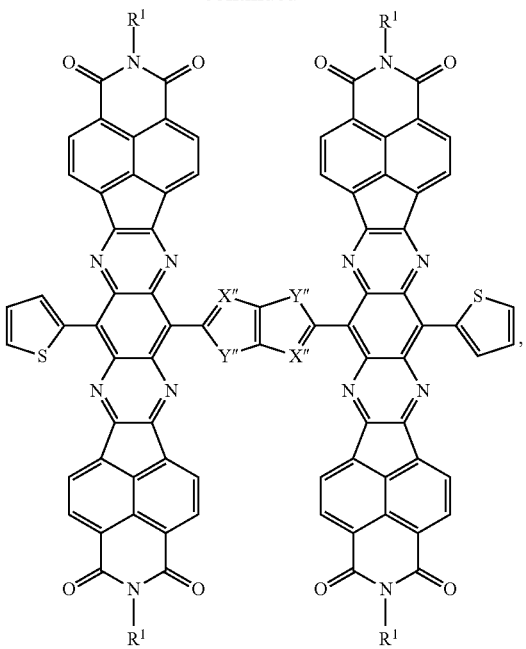
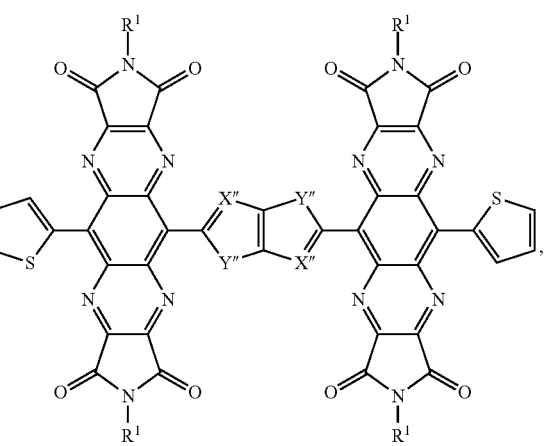
and
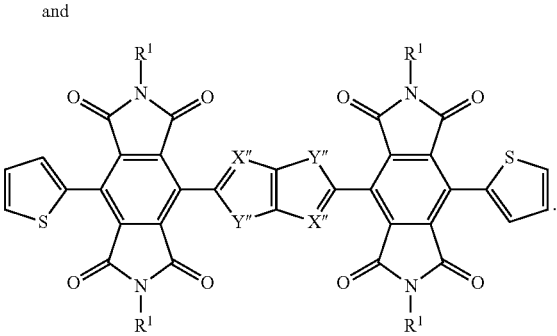
In some embodiments, the compound of Formula (I) is selected from

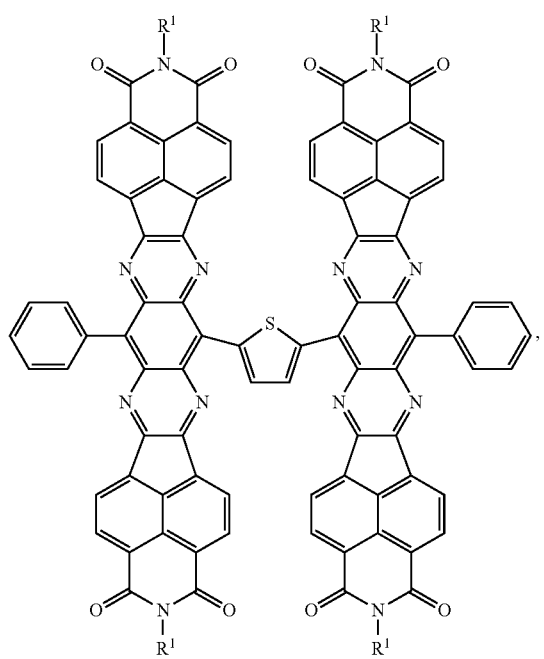
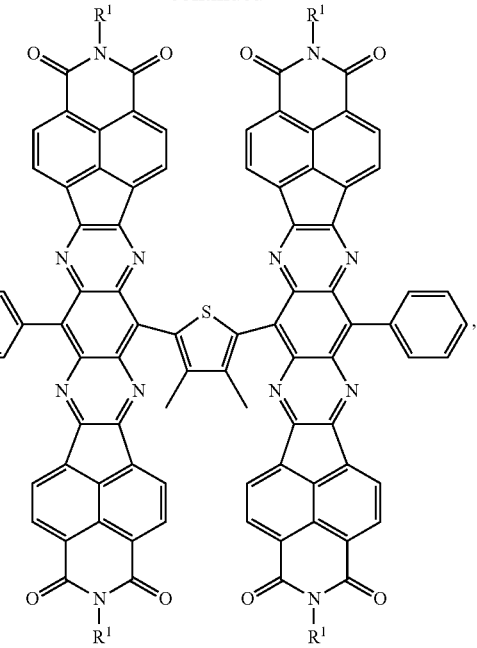
and
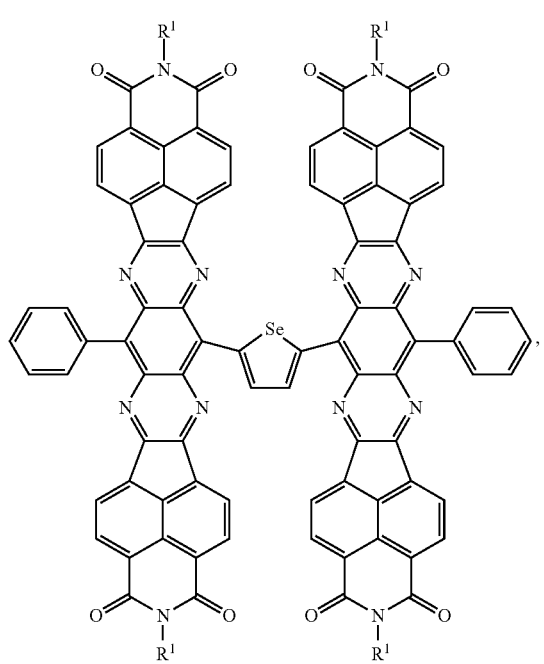
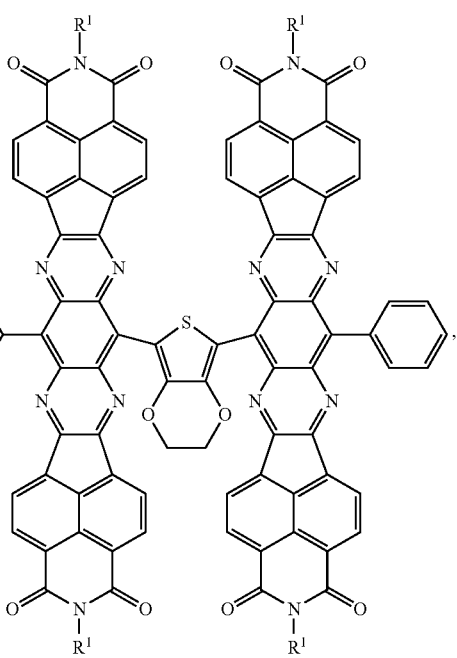
wherein R¹ is a branched alkyl (e.g., $(CH_2)CH(C_{10}H_{21})(C_{12}H_{25})$ or $(CH_2)CH(C_4H_9)(C_6H_{13})$).
In some embodiments, the compound of Formula (II) is selected from:

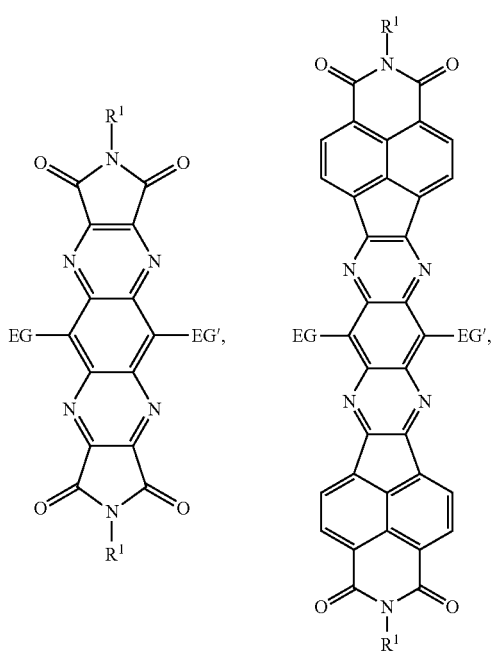
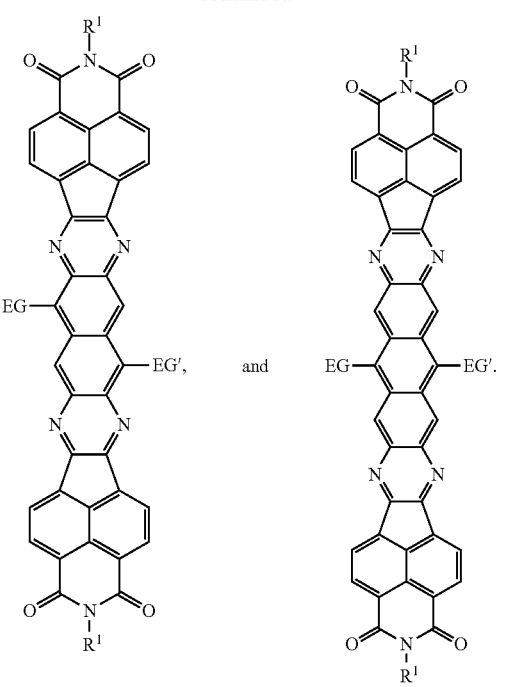
In some embodiments, the compound of Formula (II) is selected from:
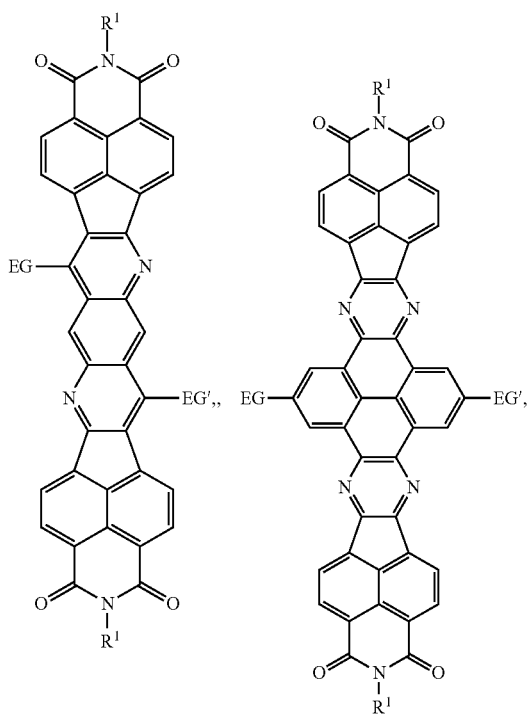
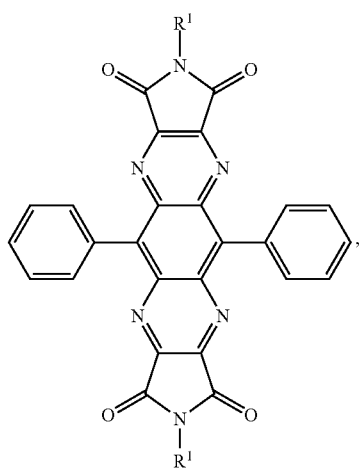

67
-continued
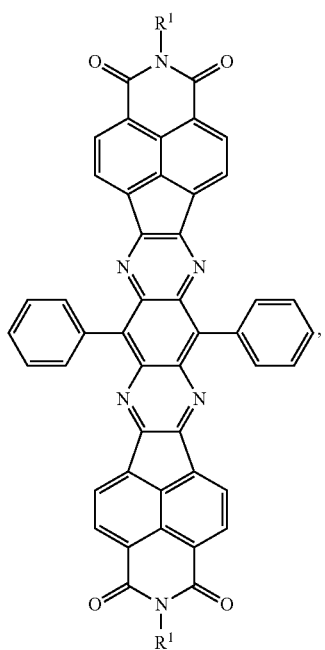
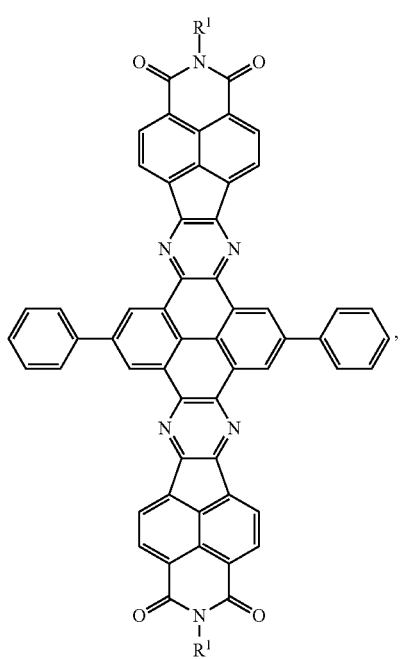
68
-continued
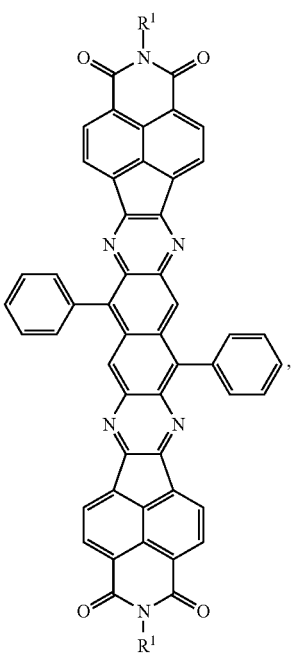
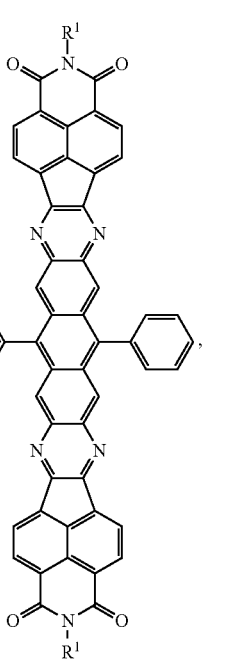, and

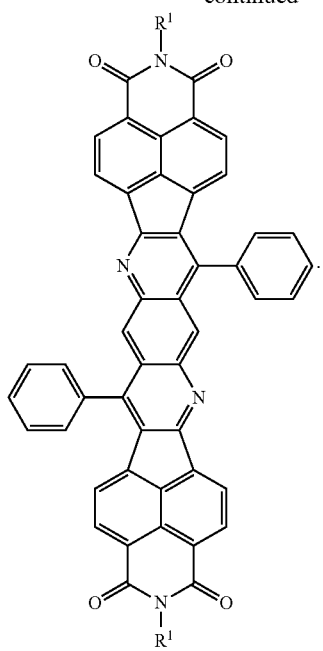
In some embodiments, the compound of Formula (II) is selected from
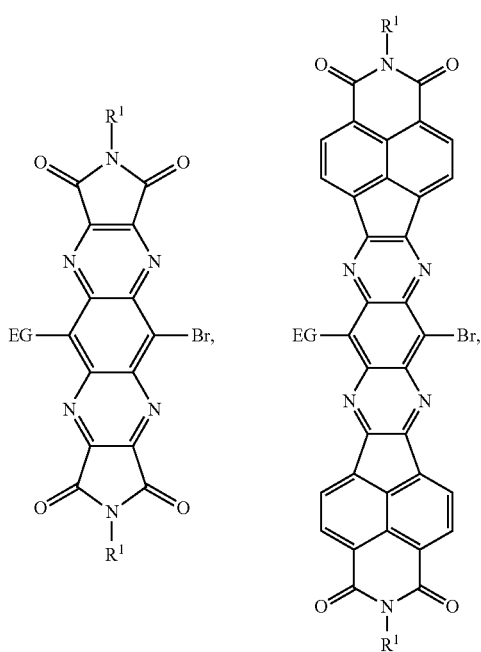
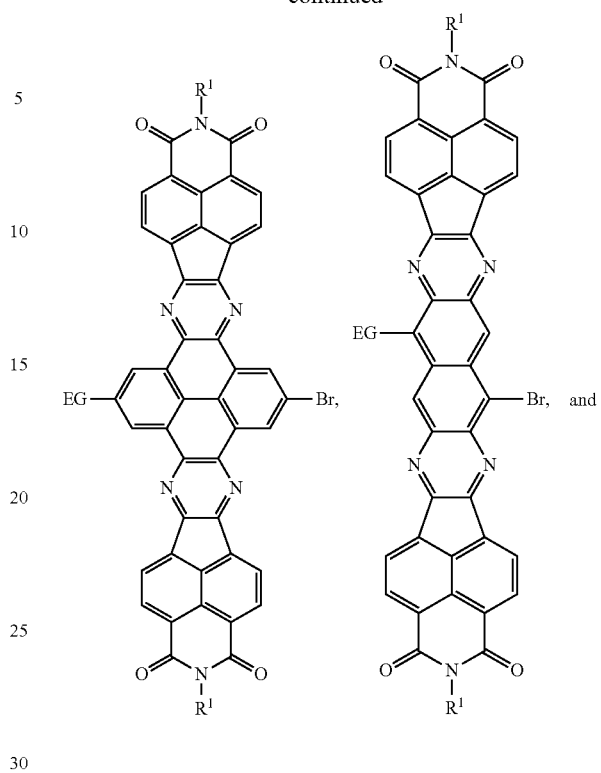
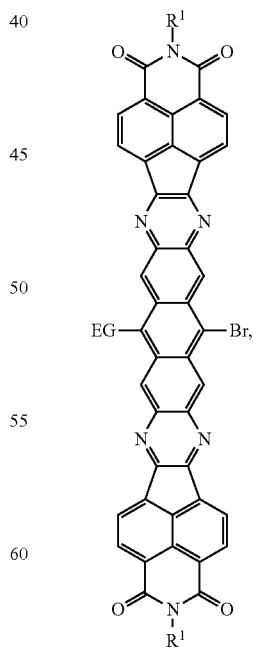
In some embodiments, the compound of Formula (II) is selected from

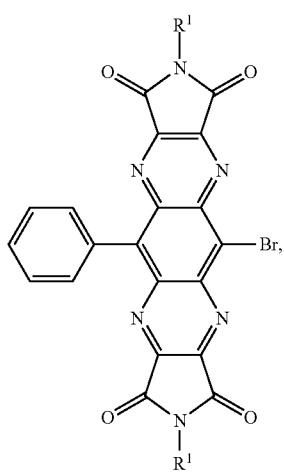
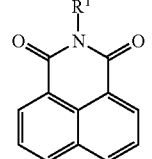
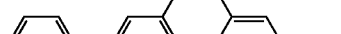
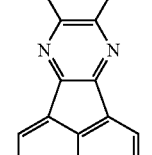
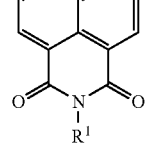
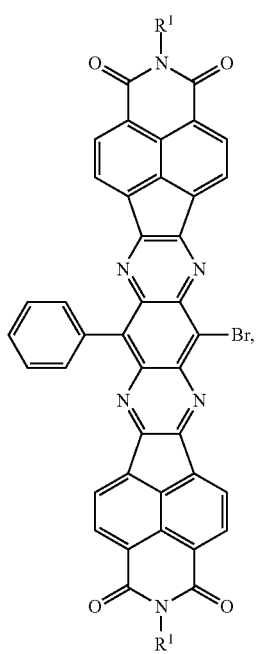
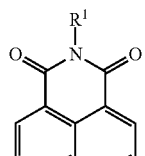
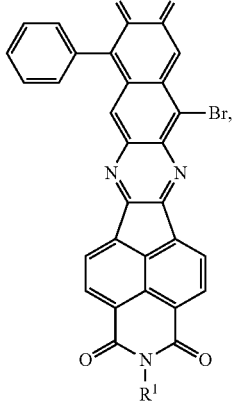

In some embodiments, the compound of Formula (II) is selected from

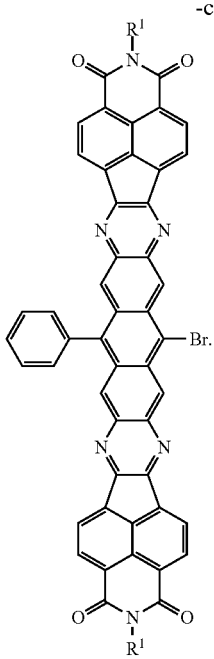

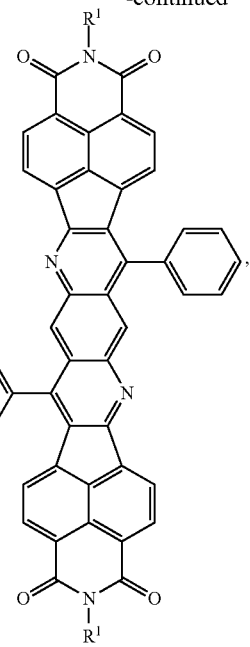

wherein $R^1$ is a branched alkyl (e.g., $(CH_2)CH(C_{10}H_{21})(C_{12}H_{25})$ or $(CH_2)CH(C_4H_9)(C_6H_{13})$.).

Without wishing to be bound by theory, it is believed that the molecular conformation of the non-fullerene electron acceptor depends primarily on the $Ar^1$ linker and secondarily on EG and EG' groups. Thus, the molecular structure of the non-fullerene electron acceptors can be fine-tuned by varying the $Ar^1$ linker, for example, from a single aromatic ring (e.g., thiophene or benzene) to two-ring groups (e.g., thienothiophene, selenoselenophene, bithiophene, etc.). For example, the conformation of each non-fullerene electron acceptor molecule can depend on the size and the orientation of the two connecting $Ar^1$ linkers: a large linker group and 180° catenation angle (the angle between two covalent bonds that connect to two neighboring $A^1$ units), such as 1,4-phenylene or 5,5'-bithiophene, can lower a steric hindrance between the two adjacent $A^1$ units, and thus result in a relatively planar conformation, stronger molecular π-π stacking, improved crystallinity, greater 2D electron delocalization, increased electron mobility, and enhanced electron delocalization along the $EG-A^1-Ar^1-A^1-EG'$ direction. In contrast, a small $Ar^1$ linkage group and a smaller catenation angle, such as 2,5-thienylene, will increase the steric hindrance between the two $A^1$ units and lead to a significantly twisted 3D architecture, poor crystallinity, and moderate charge transport.

The EG and EG' groups can each be individually modified to fine-tune the solubility, molecular packing, and crystallinity of the non-fullerene electron acceptor. The electronic properties of $A^1$ units can also be tuned by using different donor or acceptor-type EG and/or EG' groups through electron delocalization and induction effects of EG and EG'. For example, EG and/or EG' groups can include alkyl chains, alkoxy chains, aromatic rings with or without substituent groups (e.g., octyl, phenyl, 2-methyl phenyl, 2,5-dimethylphenyl, thienyl, 5-methylthienyl, etc.). Furthermore, the solubility, solid state morphology, and crystallinity of the non-fullerene electron acceptor can be improved by varying the substituents on the imine-N atoms. For example, moving the branch site of the R group from C-2 to a carbon that is further away (e.g., C-3, C-4) from the π-conjugated backbone can lower the steric hindrance between the alkyl chains and/or between the alkyl chain and the backbone, and thus increase intermolecular interactions and lead to improved crystallinity morphology in OPV devices.

In some embodiments, enhancing light harvesting by the new organic acceptors can be accomplished by extending the size of the non-fullerene electron acceptor by forming oligomers having greater than one

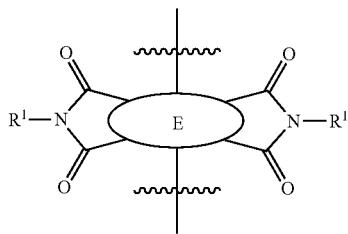

chromophore group (e.g., Formula (I) where x is 1 or 2, or Formula (III) where y is 2 or 3). However, the size of the oligomer should be balanced with processability and ease of synthesis. For example, while an oligomer having three chromophore groups (trimer) can enlarge the π-conjugated framework, increase electron delocalization and thus increase the electron-accepting and electron conducting properties compared to an oligomer having two chromophore groups (dimer), the trimer can be more insoluble and difficult to process compared to a dimer. In some embodiments, compared to a non-fullerene electron acceptor including a single chromophore, it is believed that dimers and trimers of the present disclosure can improve the ruggedness, air-stability, π-stacking, and charge carrier mobility of non-fullerene electron acceptor, while providing solution processability and tuning the degree of crystallinity. Furthermore, it is believed that dimers and trimers of the present disclosure can expand the scope of accessible morphology and energetic factors that control charge photogeneration and/or recombination processes.

Definitions

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the disclosure are stable. As used herein "stable" refers to a compound that is sufficiently robust to survive isolation to a useful degree of purity from a reaction mixture.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

"Optionally substituted" groups can refer to, for example, functional groups that may be substituted or unsubstituted by additional functional groups. For example, when a group is unsubstituted, it can be referred to as the group name, for example alkyl or aryl. When a group is substituted with additional functional groups, it may more generically be referred to as substituted alkyl or substituted aryl.

As used herein, the term "alkyl" is meant to refer to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 50, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "alkylene" refers to a linking alkyl group.

As used herein, "alkenyl" refers to an alkyl group having one or more double carbon-carbon bonds. The alkenyl group can be linear or branched. Example alkenyl groups include ethenyl, propenyl, and the like. An alkenyl group can contain from 2 to about 50, from 2 to about 24, from 2 to about 20, from 2 to about 10, from 2 to about 8, from 2 to about 6, or from 2 to about 4 carbon atoms.

As used herein, "alkenylene" refers to a linking alkenyl group.

As used herein, "alkynyl" refers to an alkyl group having one or more triple carbon-carbon bonds. The alkynyl group can be linear or branched. Example alkynyl groups include ethynyl, propynyl, and the like. An alkynyl group can contain from 2 to about 50, from 2 to about 24, from 2 to about 20, from 2 to about 10, from 2 to about 8, from 2 to about 6, or from 2 to about 4 carbon atoms.

As used herein, "alkynylene" refers to a linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "haloalkenyl" refers to an alkenyl group having one or more halogen substituents.

As used herein, "haloalkynyl" refers to an alkynyl group having one or more halogen substituents.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "arylene" refers to a linking aryl group.

As used herein, "monocyclic aromatic core" refers to monocyclic aromatic hydrocarbons and monocyclic aromatic heterocycles having at least one heteroatom ring member such as sulfur, oxygen, or nitrogen. Any ring-forming N atom in a monocyclic aromatic heterocycle can also be oxidized to form an N-oxo moiety. Examples of monocyclic aromatic hydrocarbons include benzene and the like. In some embodiments, the monocyclic aromatic hydrocarbons have 6 carbon atoms. Examples of monocyclic aromatic heterocycles include without limitation, pyridine, pyrimidine, pyrazine, pyridazine and the like. In some embodiments, the monocyclic aromatic heterocycle contains 6 to about 14 ring-forming atoms. In some embodiments, the monocyclic aromatic heterocycle has 1 to about 4, 1 to about 3, or 1 to 2 heteroatoms.

As used herein, "polycyclic aromatic core" refers to a fused aromatic ring system (e.g., having 2, 3, 4, 5, 6, 7, 8, 9, 10, 11, 12, 13, 14, 15, or 16 fused rings) that optionally includes one or more heteroatom ring members such as sulfur, oxygen, or nitrogen. Examples of polycyclic aromatic core include naphthyl, anthracenyl, phenanthrenyl, indanyl, indenyl, and the like. Examples of polycyclic aromatic cores that include one or more heteroatom ring members include quinoline, isoquinoline, benzofuran, benzothiophene, benzthiazole, pyrazino[2,3-g]quinoxaline, acenaphtho[1',2':5,6]pyrazino[2,3-g]acenaphtho[1,2-b]quinoxaline, and the like. In some embodiments, the polycyclic aromatic core has from 1 to about 30 carbon atoms, 1 to about 20 carbon atoms, and in further embodiments from about 6 to about 20 carbon atoms. In some embodiments, the polycyclic aromatic core contains 3 to about 20, 3 to about 14, 3 to about 7, or 5 to 6 ring-forming atoms. In some embodiments, the polycyclic aromatic core has 1 to about 8, 1 to about 4, 1 to about 3, or 1 to 2 heteroatoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbomyl, norpinyl, norcamyl, adamantyl, and the like.

As used herein, "cycloalkylene" refers to a linking cycloalkyl group.

As used herein, "heteroalkyl" refers to an alkyl group having at least one heteroatom such as sulfur, oxygen, or nitrogen.

As used herein, "heteroalkylene" refers to a linking heteroalkyl group.

As used herein, a "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heteroarylene" refers to a linking heteroaryl group.

As used herein, "heterocycloalkyl" refers to a non-aromatic heterocycle where one (or more) of the ring-forming atom(s) is a heteroatom such as an O, N, or S atom. Heterocycloalkyl groups can include mono- or polycyclic (e.g., having 2, 3 or 4 fused rings) ring systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. A heterocycloalkyl group having one or more fused aromatic rings can be attached though either the aromatic or non-aromatic portion. Also included in the definition of heterocycloalkyl are moieties where one (or more) ring-forming atom(s) is substituted by 1 or 2 oxo or sulfido groups. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "heterocycloalkylene" refers to a linking heterocycloalkyl group.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-(haloalkyl) group.

As used herein, "amino" refers to $NH_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated.

Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone— enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the disclosure can also include all isotopes of atoms occurring in the intermediates or final compounds. Isotopes include those atoms having the same atomic number but different mass numbers. For example, isotopes of hydrogen include tritium and deuterium.

In some embodiments, the compounds of the disclosure, and salts thereof, are substantially isolated. By "substantially isolated" is meant that the compound is at least partially or substantially separated from the environment in which it was formed or detected. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Synthesis

The novel compounds of the present disclosure can be prepared in a variety of ways known to one skilled in the art of organic synthesis. The compounds of the present disclosure can be synthesized using the methods as hereinafter described below, together with synthetic methods known in the art of synthetic organic chemistry or variations thereon as appreciated by those skilled in the art.

The compounds of this disclosure can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 4th. Ed., Wiley & Sons, 2006, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

The compounds of the disclosure can be prepared, for example, using the reaction pathways and techniques as described below.

Compounds of formula I described herein can be synthesized by coupling reactions, for example, Stille coupling reaction or Suzuki coupling reactions, as described, for example, in Stille, J. K. *Angew. Chem. Int. Ed.* 1986, 25, 508; N. Miyaura and A. Suzuki, *Chem. Rev.* 1995, 95, 2457; and J. Seechurn, et al., *Angew. Chem. Int. Ed.* 2012, 51, 5062, each of which is herein incorporated in its entirety. EG,

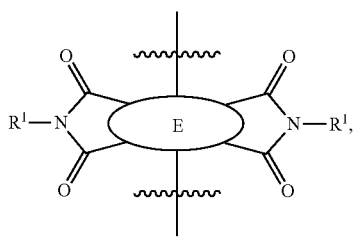

$A^1$, and $Ar^1$ can be covalently bonded through coupling reactions of corresponding mono- or di-functional starting materials, such as EG-FG, FG-$A^1$-FG, FG-$Ar^1$-FG, $A^1$-FG, and $Ar^1$-FG, where FG denotes a functional group and the FG's can be the same or different.

The functional group (FG) can be independently selected from, for example,

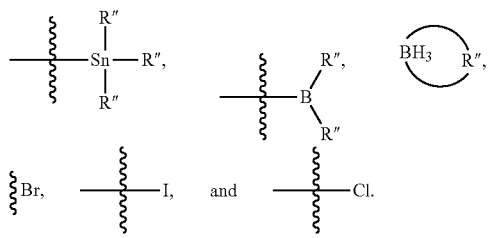

These mono- or di-functional starting materials can be made via different functionalization reactions, for example via halogenation, borylation, or stannylation reactions to introduce halide, boryl (e.g., boronic ester or boronic acid), or stannyl group, respectively, as described, for example, at www2.chemistry.msu.edu/faculty/reusch/VirtTxtJml/intro1.htm; and in *Organic chemistry*. Englewood Cliffs, N.J: Prentice Hall, p. 947.ISBN 0-13-643669-2, each of which is herein incorporated in its entirety.

R" can be an optionally substituted linear or branched alkylene moiety, or optionally substituted linear or branched heteroalkylene moiety.

As a non-limiting example, compounds of formula I can be synthesized by the route shown in Scheme 1. For simplicity, A is shown in Scheme 1. However, it is understood that the various A groups can correspond to

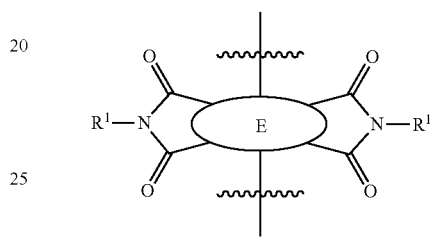

or $A^1$ to arrive at compounds of Formulas (I) and (II). Compounds of Formula (III) can be obtained by coupling FG-A-EG with A-FG.

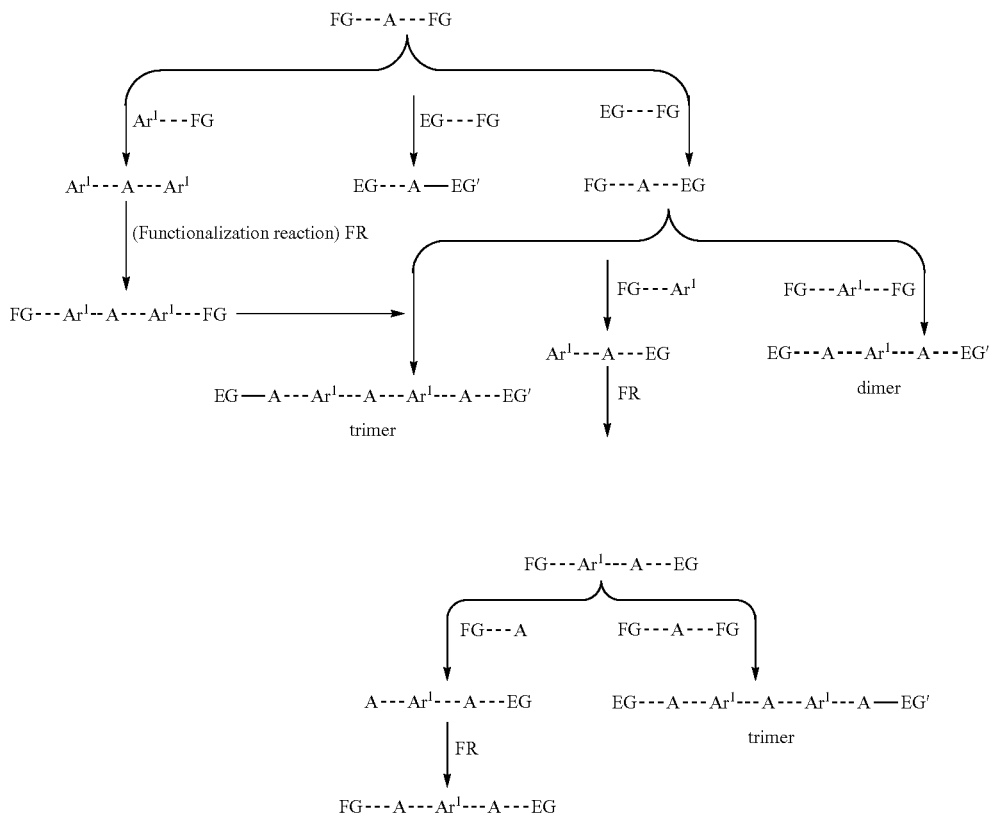

Scheme 1.

As another example, a compound of Formula (I) and (II) can be synthesized by a route (or a similar route, as known to a person of skill in the art) shown in Scheme 2. In some embodiments, compounds of Formula (III) can be made in an analogous manner, for example, by coupling dibromo-functionalized starting material (e.g., compound A) with a mono-brominated compound (e.g., compound D).

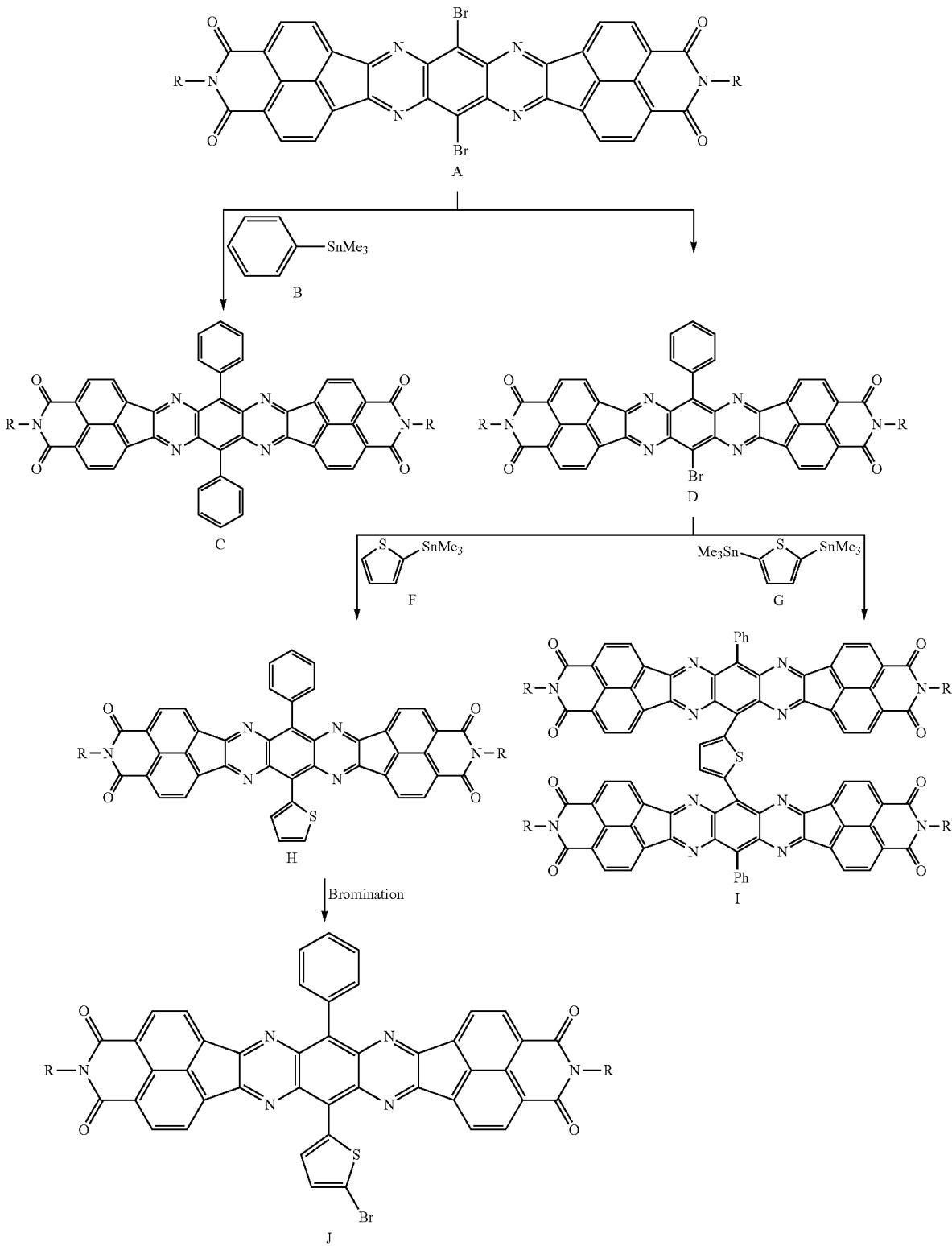

Scheme 2.

Compounds of formula FG-A¹-FG can be synthesized by ring closure reaction, as described in H. Li et al., *Angew. Chem. Int. Ed.* 2013, 52, 5513; Y. Zhu et al., *Macromol. Rapid Commun.* 2004, 25, 1829, each of which is herein incorporated by reference, of a diketo intermediate with a second compound represented by

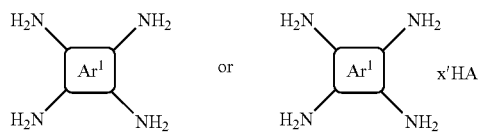

(where HA is HCl, HBr, HI, CH₃COOH, H₂SO₄ or H₃PO₄, and x' is 1, 2, 3 or 4) to obtain a third compound represented by

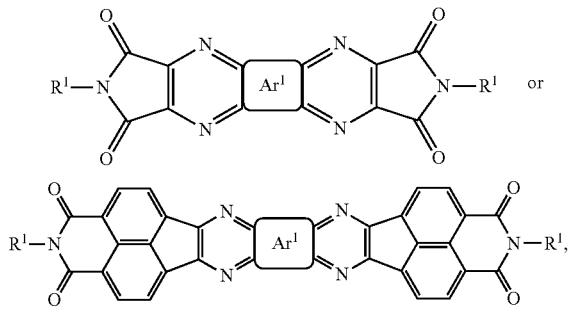

where Ar¹ can be, for example, a phenylene, pyrenylene, naphthalenylene, or anthracenylene group, with or without FG. The functional group FG can be added before or after the ring closure reaction, for example, by halogenation, borylation, or stannylation reaction to add one or two halogen, boryl, or stannyl groups respectively to the Ar¹ group.

The diketone intermediate can be, for example,

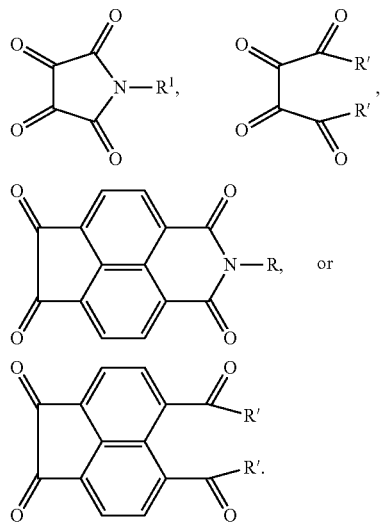

In some embodiments, if the diketone intermediate is

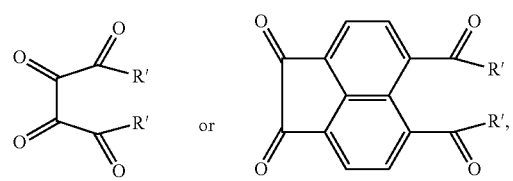

the dicarboxylic imide group(s) in FG-A¹-FG,

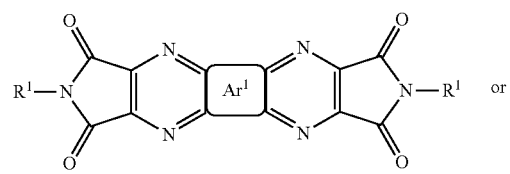

can be obtained by following procedures, as described, for example in B. M. Trost, et al., *J. Am. Chem. Soc.* 1971, 93, 737; H. Li, et al., *Angew. Chem. Int. Ed.* 2013, 52, 5513; each of which is herein incorporated in its entirety.

Compound of formula

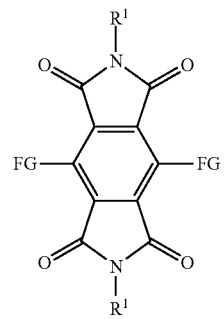

can be synthesized, for example, using procedures, as described, for example, in PCT Publication No. WO2010/011658, herein incorporated by reference in its entirety.

Compound of formula

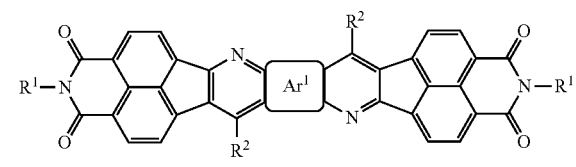

can be made by, for example, reacting a monoketo intermediate

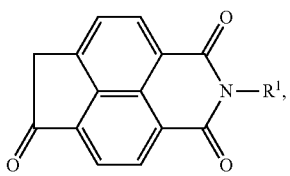

with a second compound represented by

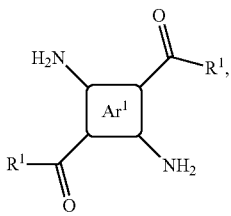

wherein $Ar^1$ and $R^1$ have the same definitions as previously described.

Organic Electronic Devices

The non-fullerene electron acceptors herein have advantageous electronic structures and solid morphologies for applications in organic electronic and optoelectronic devices. Therefore, also provided are organic electronic devices and optoelectronic devices including one or more of the non-fullerene electron acceptors, such as organic photovoltaics (OPVs), solar cells, transistors, organic field effect transistors (OFETs), photodetectors, thin film transistors (TFTs), logic circuits, integrated circuits, radio frequency identification tags (RFID), flat displays, light emitting diodes (LEDs), light emitting transistor, high-performance field-effect transistor, complementary inverter, etc. Examples of organic electronic devices are described, for example, in Anthony, J. E. Chem. Mater. 2011, 23, 583; Sonar, P., et al. Energy Environ. Sci. 2011, 4, 1558; Anthony, J. E., et al. Adv. Mater. 2010, 22, 3876-3892; Zaumseil, J., Sirringhaus, H. Chem. Rev. 2007, 107, 1296; and Usta, H., et al. J. Acc. Chem. Res. 2011, 44, 501; each of which is herein incorporated in its entirety. The non-fullerene electron acceptors can also be used as photoconducting, charge transporting, semiconducting, and/or light emitting components in electronic or optoelectronic devices.

Without wishing to be bound by theory, it is believed that orbital energy levels, which determine the facility of electron injection from electrodes, and close molecular packing in a highly crystalline film, can contribute to stability and durability of a device including the non-fullerene electron acceptors. When used in solar cells, because of the differences in molecular geometry between the non-spherical non-fullerene electron acceptors compared with spherical fullerenes and the ensuing differences in blend morphology, the mechanism of the charge photogeneration and collection in non-fullerene electron acceptor/p-polymer solar cells can be different from those of the well-studied polymer/fullerene systems. For example, the significant light harvesting by non-fullerene electron acceptors in BHJ solar cells can be attributed to photoinduced hole transfer, which can be a major pathway in the charge photogeneration process. In contrast, hole transfer plays a relatively minor role in charge photogeneration in polymer/fullerene systems because of the negligible light absorption by the fullerene acceptor in the visible-near IR region.

The non-fullerene electron acceptors can be present as a thin film in the electronic or optoelectronic devices. In some embodiments, the non-fullerene electron acceptors have good solubility in common organic solvents; therefore they can be processed using solution processing techniques including spin coating, casting, dip coating, inkjet printing, screen printing, spray coating, doctor blade coating, roll coating, bar coating, die coating and dispense methods, and may also be employed in thermal evaporation or solution processes for making organic electronic devices. The solution can be prepared by dissolving the non-fullerene electron acceptors into a solvent or mixed solvents such as chloroform, dichloromethane, toluene, chlorobenzene, dichlorobenzene, trichlorobenzene, xylene, trifluoroacetic acid, formic acid, acetic acid, etc. at room temperature or at high temperature. The thickness of the thin films can be adjusted to fit the need of different applications.

Solar Cells

Figure 4A:
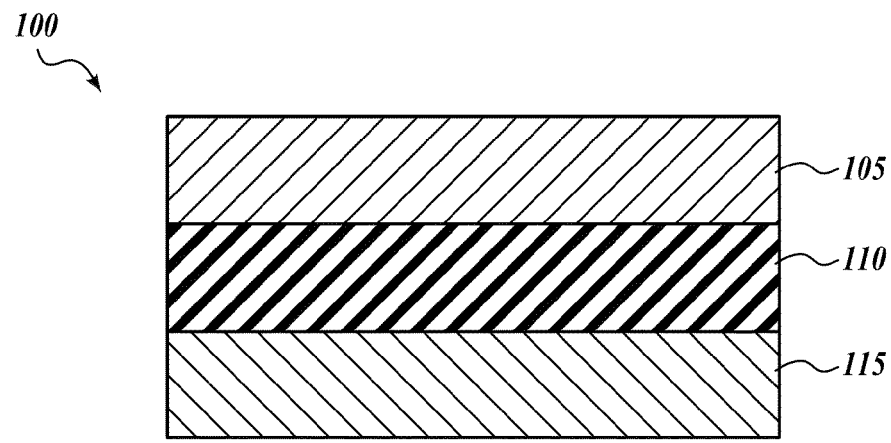
FIG. 4A is a schematic illustration of a representative photovoltaic device of the disclosure having a bulk heterojunction layer that includes an embodiment of a non-fullerene electron acceptor.
Figure 4B:
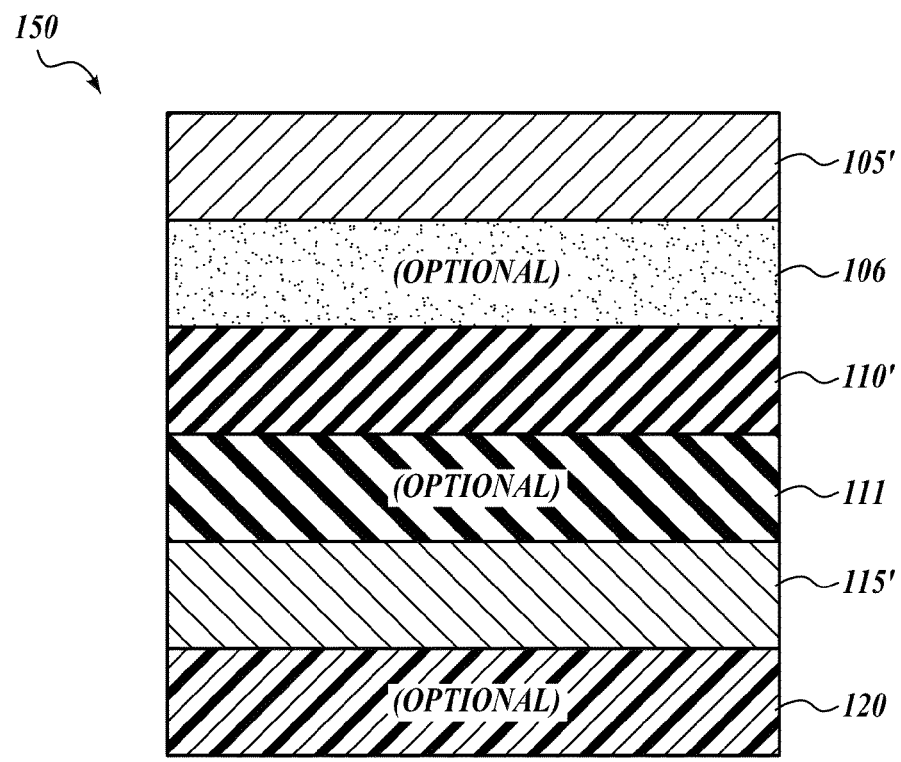
FIG. 4B is schematic illustration of a representative photovoltaic device of the disclosure having a bulk heterojunction layer that includes an embodiment of a non-fullerene electron acceptor.

FIGS. 4A and 4B are schematic illustrations of representative solar cells that advantageously incorporate the non-fullerene electron acceptors of the present disclosure. In these devices, the non-fullerene electron acceptors are a component of the devices' photovoltaic layer.

Referring to FIG. 4A, representative device 100 includes hole-collecting electrode 115, electron-collecting electrode 105, and photovoltaic layer 110. Photovoltaic layer 110 can include non-fullerene electron acceptors of the present disclosure. Hole-collecting electrodes can include a material such as a continuous metal, a metal grid, indium-tin oxide, and a conductive polymeric material. Electron-collecting electrodes can include a conductive metal.

Referring to FIG. 4B, representative device 150, in addition to hole collecting electrode 115', electron-collecting electrode 105', and photovoltaic layer 110', device 150 includes optional layers 106 (electron-transporting layer), 111 (hole-transporting layer), and 120 (substrate). Electron-transporting layers 106 can include a metal oxide (e.g., zinc oxide, titanium oxide, etc.). Hole transporting layer 111 is intermediate to the photovoltaic layer and the hole-collecting electrode. Substrate 120 abuts either the electron-collecting electrode or the hole-collecting electrode.

The non-fullerene electron acceptors can function as high performance acceptors in BHJ solar cells. In current organic solar cells, poor exciton dissociation and high charge carrier recombination generally lead to efficiency decrease with increasing light intensity. The non-fullerene electron acceptors promise to alleviate this bottleneck, while offering many additional opportunities for innovation in the design of devices, ranging from better light harvesting and charge transport to novel mechanism of photocurrent generation.

Organic solar cells including at least one non-fullerene electron acceptor can be made by, for example, first spin-coating a buffer layer, such as a PEDOT:PSS buffer layer, on top of an electrode and substrate, such as ITO-coated glass substrates (e.g., 10Ω/sq, Shanghai B. Tree Tech. Consult Co., Ltd., Shanghai, China). Spin coating is known in the art and the spin coating can be adapted to the needs. One example is to spin coat at 1500 rpm for 60 s and dry at 150° C. for 10 min under vacuum. The thickness of the buffer layer (e.g., PEDOT:PSS) can be, for example, around 10 nm to 100 nm, or about 40 nm.

Solar cells described herein can also be fabricated by, for example, first spin-coating a buffer layer, such as a ZnO, on top of an electrode and substrate, such as ITO-coated glass substrates (e.g., 10Ω/sq, Shanghai B. Tree Tech. Consult Co., Ltd., Shanghai, China). Spin coating is known in the art and the spin coating can be adapted to the needs. One example is to spin coat at 1500 rpm for 60 s and dry at 250° C. for 60 min in air. The thickness of the buffer layer (e.g., ZnO) can be, for example, around 10 nm to 100 nm, or about 30 nm. In some embodiments, a thin layer of surface modifier such as ethanoamine, 2-aminophenol, 3-aminophenol, a fullerene derivative, etc. can be spin-coated on top of the buffer layer (e.g., ZnO). For example, a dilute ethanoamine solution in 2-methoxyethanol (1 vol %) can be spin-coated, followed by drying at 110° C. for 10 min.

The active layer of the solar cells including the non-fullerene electron acceptors can include a mixed "heterojunction" active layer that is a phase separated blend of the non-fullerene electron acceptors described herein and an electron donor material. The electron donor materials can be a variety of organic materials (small molecules, oligomers, polymers, or polymer composites) that have a LUMO energy level that is at least about 0.2 to 0.6 eV more positive than the LUMO energy level of the compounds described herein, and a HOMO energy level that is more positive than the HOMO energy level of the compounds described herein.

In some embodiments, a composite or composition including a solution or dispersion of one or more of non-fullerene electron acceptors and one or more donor materials, for example, P3HT or poly[(4,4'-bis(3-(2-ethyl-hexyl) dithieno[3,2-b:2',3'-d]silole)-2,6-diyl-alt-(2,5-bis(3-(2-ethyl-hexyl)thiophen-2yl)thiazolo[5,4-d]thiazole)] (PSEHTT, (as described in Chinese Patent Application No. CN102782011A, European application Patent Application EP2493960A1, U.S. Publication No. US20120273732, and *Adv. Energy Mater.* 2011, 1, 854-860, each of which is herein incorporated by reference in its entirety), is spin-coated on top of the PEDOT:PSS layer to form a layer including the one or more material described herein and one or more electron donating materials. Other examples of polymeric donor materials include poly[(4,8-bis-(2-ethylhexyloxy)-benzo(1,2-b:4,5-b')dithiophene)-2,6-diyl-alt-(4-(2-ethyl-hexyl)-3-fluorothieno[3,4-b]thiophene-)-2-carboxylate-2-6-diyl)] ("PTB7," available from Solarmer Materials, Inc.), poly[4,8-bis(5-(2-ethylhexyl)thiophen-2-yl)benzo[1,2-b;4,5-b']dithiophene-2,6-diyl-alt-(4-(2-ethylhexanoyl)-thieno[3,4-b]thiophene-)-2-6-diyl)] ("PBDTTT-C-T," available from Solarmer materials, Inc.), and poly[4,8-bis(5-(2-ethylhexyl)thiophen-2-yl)benzo[1,2-b;4,5-b']dithiophene-2,6-diyl-alt-(4-(2-ethylhexyl)-3-fluorothieno[3,4-b]thiophene-)-2-carboxylate-2-6-diyl)] ("PBDTT-FTTE," available from Solarmer materials, Inc.).

In some embodiments, the active layer of the solar cells that includes the non-fullerene electron acceptors and/or the polymer donors described herein can include a mixed "heterojunction" active layer that is a phase separated blend of the materials described herein and an electron acceptor material. The electron acceptor material can include one or more non-fullerene electron acceptors of the present disclosure and one or more other organic electron acceptor materials (e.g., small molecules, oligomers, or polymers) that have a LUMO energy level that is at least about 0.2 to 0.6 eV more negative than the LUMO energy level of the polymeric donors described herein, and a HOMO energy level that is more negative than the HOMO energy level of the polymeric donors described herein. In some embodiments, in addition to the non-fullerene electron acceptors of the present disclosure, the electron acceptor material can further include a fullerene or a modified fullerene (e.g., $C_{61}$-phenyl-butyric acid methyl ester, $PC_{61}BM$, or $C_{71}$-phenyl-butyric acid methyl ester, $PC_{71}BM$). Examples of other organic electron acceptor materials can include small molecules, oligomers, polymers, or polymers having highly electron deficient functional groups, such as naphthalene diimide, perylene diimide, phthalimide, benzothiadiazole, diketopyrrolopyrrole, indan-1,3-dione, fluoroanthene imide, and derivatives thereof.

In some embodiments, a composition including a solution or dispersion of one or more non-fullerene electron acceptors of the present disclosure and one or more other organic electron acceptor materials (for example fullerene derivatives) is spin-coated (e.g. at 1000 rpm for 30 seconds) on top of a buffer layer, such as a PEDOT:PSS layer, to form a layer including one or more non-fullerene electron acceptors described herein and one or more other organic electron acceptor materials. In some embodiments, the solution or dispersion is applied using a hot solvent, and dried under vacuum immediately after the deposition the donor polymers (e.g., P3HT, PSEHTT, PBDTT-FTTE, etc.).

The coated device precursor can then be annealed, for example on a hot plate in a glove box, to form the active layer. The active layer can also be spin-coated in air and dried in a vacuum oven without thermal annealing. The solvents for dissolving the mixture of the non-fullerene electron acceptors and the electron donors can be chloroform, chlorobenzene, 1,2-dichlorobenzene, etc. The solvents for the blend can be a single solvent such as chloroform, chlorobenzene, 1,2-dichlorobenzene or a mixture of two or three different solvents, the second (third) solvent can be 1,8-diiodooctane, 1,8-dibromoctane, 1,8-octanedithiol, etc. Optionally, the solvents can be heated so as to increase the solubility of the material described herein and/or the electron donors or the electron acceptors, as an aid to film formation.

Thermal annealing is believed to induce at least partial phase separation between the electron acceptors and the electron donors, forming the "heterojunctions" on the nanometer scale that are believed to be the site of light-induced charge separation.

After cooling down, the solar cell precursors comprising the active material-coated substrates can be taken out of the glove box and loaded in a thermal evaporator (e.g., BOC Edwards, 306) for the deposition of the cathode. The cathode consisting of, for example, 1.0 nm LiF and 80 nm aluminum layers, can be sequentially deposited through a shadow mask on top of the active layers in a vacuum of, for example, $8 \times 10^{-7}$ torr. Each substrate can contain, for example, a plurality of (e.g., 5) solar cells with an active area of, for example, 4 mm$^2$.

A BHJ including a non-fullerene electron acceptor of the present disclosure can perform more efficiently than an analogous BHJ including a fullerene electron acceptor. For example, a BHJ including a non-fullerene electron acceptor of the present disclosure can improve PCE by about 0.5% to 3% (e.g., by about 0.5% to about 2%, by about 0.5% to about 1.5%, by about 0.5% to 1%, by about 1% to 3%, or by about 1% to 2%), compared to an analogous BHJ including a fullerene electron acceptor.

Examples of organic photovoltaics are further described, for example, in Ren, G et al., *Adv. Energy Mater.* 2011, 1, 946-953; Li, H. et al., *Angew. Chem. Int. Ed.* 2013, 52, 5513-5517; Earmme, T. et al., *J. Am. Chem. Soc.* 2013, 135, 14960-14963; Zang, Y., et al. *Adv. Mater.* 2014, 10.1002/adma.201401992; Earmme, T., et al. *Adv. Mater.* 2014, DOI: 10.1002/adma.201401490, each of which is herein incorporated by reference in its entirety.

Transistors

Figure 5A:
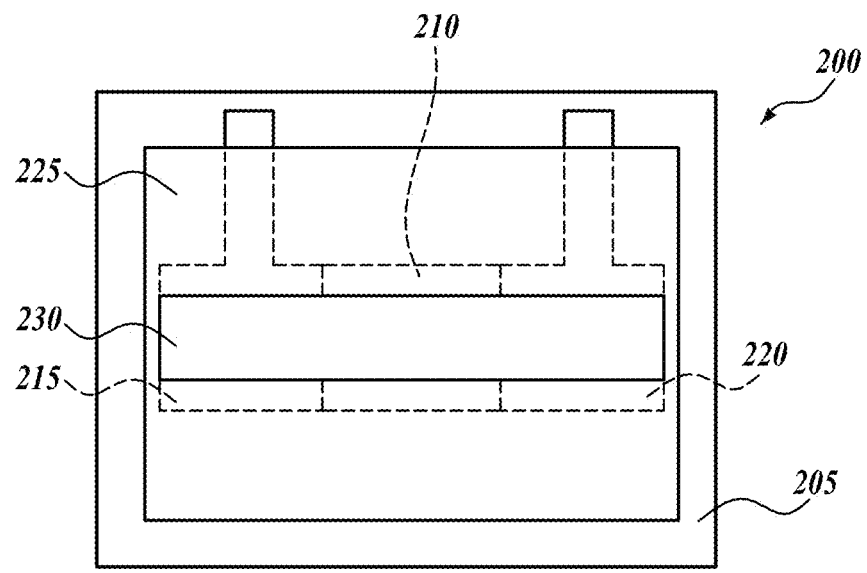
FIG. 5A is a schematic diagram showing the top view of a top-gate organic transistor.
Figure 5B:
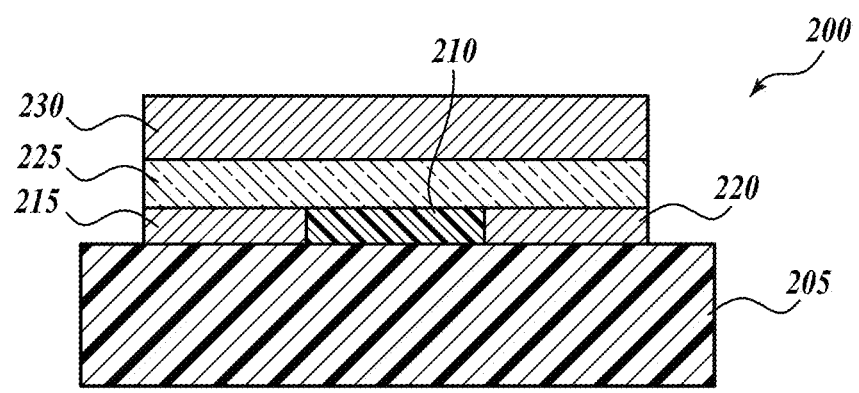
FIG. 5B is a side view of the organic transistor shown in FIG. 5A.

OFETs are devices that are compatible with manufacture by printing. One type of OFET, a top-gate OFET, will now be described. FIGS. 5A and 5B illustrate a top view (FIG.

5A) and a side view (FIG. 5B) of an organic field-effect transistor (OFET). Referring now FIGS. 5A and 5B, the OFET 200 is built on a foundation of a substrate 205 comprised of any material capable of supporting the following layers. Representative substrate materials include polymers, semiconductor and insulator wafers, and crystals. Upon the substrate 205, a source electrode 215 and a drain electrode 220 are patterned using techniques known to those of skill in the art (e.g., photolithography). The source 215 and drain 220 electrodes are typically metals, but can also be conducting organic materials. A semiconductor layer 210 having substantially planar upper and lower surfaces and uniform thickness, typically composed of a polymer or small molecule semiconductor, is deposited between the source electrode 215 and drain electrode 220. An insulating layer 225 of uniform thickness is deposited upon the source electrode 215, drain electrode 220, and semiconductor layer 210. Finally, a gate electrode 230 is deposited on the insulating layer 225 such that the gate electrode 230 is substantially aligned with the area of the semiconductor layer 210 (e.g., the gate electrode 230 spans the semiconductor layer 210 between the source electrode 215 and the drain electrode 220).

The field-effect transistor can include a thin-film of the non-fullerene electron acceptors described herein, within (or as part of) the semiconductor layer 210. The thin film can be deposited from a solution of the non-fullerene electron acceptors. The thin-film can be fabricated by spin coating. The thin-film can be fabricated by vacuum vapor deposition.

The field-effect transistor can be an n-channel transistor, or an ambipolar transistor. The electron mobility of the field-effect transistor can be, for example, $1 \times 10^{-5}$ cm$^2$/Vs or higher, or $1 \times 10^{-4}$ cm$^2$/Vs or higher, or $1 \times 10^{-3}$ cm$^2$/Vs or higher, or $1 \times 10^{-2}$ cm$^2$/Vs or higher, or 0.1 cm$^2$/Vs or higher. The on/off current ratio of the field-effect transistor can be, for example, at least $10^4$, or at least $10^5$, or at least $10^6$, or about $10^4$-$10^7$, or about $10^5$-$10^6$.

The organic thin film transistors described herein can have a configuration such that a semiconductor layer including the compounds described herein is formed therein while also contacting the source electrode, drain electrode and insulating layer of the transistor.

The organic thin film transistor can be thermally annealed. Annealing is performed while the film is set on a substrate, and is believed (without wishing to be bound by theory) to allow for at least partial self-ordering and/or π-stacking of the compounds and/or polymers to occur in the solid state. The annealing temperature is determined depending on the property of the material, but is preferably from room temperature to 300° C., and more preferably from 50 to 300° C. In many embodiments, thermal annealing is carried out at least 150° C., or preferably above 170° C., or above 200° C. When the annealing temperature is too low, the organic solvent remaining in the organic film cannot be well removed therefrom. In contrast, when the annealing temperature is too high, the organic film can be thermally decomposed. Annealing is preferably performed in a vacuum, or under nitrogen, argon or air atmosphere. In some embodiments annealing is performed in an atmosphere including a vapor of an organic solvent capable of dissolving the material so that the molecular motion of the material is accelerated, and thereby a good organic thin film can be prepared. The annealing time is properly determined depending on the aggregation speed of the material.

An insulating (dielectric) layer is used in the organic thin film transistors, situated between the gate electrode and the organic thin film comprising the non-fullerene electron acceptors. Various insulating materials can be used for the insulating layer. Specific examples of the insulating materials include inorganic insulating materials such as silicon oxide, silicon nitride, aluminum oxide, aluminum nitride, titanium oxide, tantalum oxide, tin oxide, vanadium oxide, barium strontium titanate, barium zirconate titanate, lead zirconium titanate, lead lanthanum titanate, strontium titanate, barium titanate, barium magnesium fluoride, bismuth tantalate niobate, hafnium oxide, and trioxide yttrium; organic insulating materials such as polymer materials, e.g., polyimide, polyvinyl alcohol, polyvinyl phenol, polystyrene, polyester, polyethylene, polyphenylene sulfide, unsubstituted or halogen-atom substituted polyparaxylylene, polyacrylonitrile, and cyanoethyl pullulan; etc. These materials can be used alone or in combination. Among these materials, materials having a high dielectric constant and a low conductivity are preferably used.

Suitable methods for forming such an insulating layer include dry processes such as CVD methods, plasma CVD methods, plasma polymerization methods, and vapor deposition methods; wet processes such as spray coating methods, spin coating methods, dip coating methods, inkjet coating methods, cast coating methods, blade coating methods, and bar coating methods; etc.

In order to improve the adhesion between the insulating layer and organic semiconductor layer, to promote charge transport, and to reduce the gate voltage and leak current, an organic thin film (intermediate layer) can be employed between the insulating layer and organic semiconductor layer. The materials for use in the intermediate layer are not particularly limited as long as the materials do not chemically affect the properties of the organic semiconductor layer, and for example, molecular films of organic materials, and thin films of polymers can be used therefor. Specific examples of the materials for use in preparing the molecular films include coupling agents such as octadecyltrichlorosilane, octyltrichlorosilane, octyltrimethoxysilane, hexamethyldisilazane (HMDS), and octadecylphosphonic acid. Specific examples of the polymers for use in preparing the polymer films include the polymers mentioned above for use in the insulating layer. Such polymer films can serve as the insulating layer as well as the intermediate layer.

The materials of the electrodes (such as gate electrodes, source electrodes and drain electrodes) of the organic thin film transistor described herein are not particularly limited as long as the materials are electrically conductive. Specific examples of the materials include metals such as platinum, gold, silver, nickel, chromium, copper, iron, tin, antimony, lead, tantalum, indium, aluminum, zinc, tungsten, titanium, calcium, and magnesium; alloys of these metals; electrically conductive metal oxides such as indium tin oxide (ITO); inorganic or organic semiconductors, whose electroconductivity is improved by doping or the like, such as silicon single crystal, polysilicon, amorphous silicon, germanium, graphite, carbon nanotube, polyacetylene, polyparaphenylene, polythiophene, polypyrrole, polyaniline, polythienylenevinylene, polyparaphenylenevinylene, and complexes of polyethylenedioxythiophene (PEDOT) and polystyrene sulfonic acid.

Organic field effect transistors and complementary circuits are further described, for example, in Li, H., et al., *Angew. Chem. Int. Ed.* 2013, 52, 5513-5517; Yan, H., et al. *Nature* 2009, 457, 679-686; and Li, H., et al. *J. Am. Chem. Soc.* 2013, 135, 14920-14923, each of which is herein incorporated by reference in its entirety.

The following examples are included for the purpose of illustrating, not limiting, the described embodiments.

Examples 1, 4, 9, 12, 14, 16, and 20 describe the synthesis and characterization of examples of non-fullerene electron acceptors of the present disclosure. Examples 2, 3, 5-8, 10, 11, 13, 15, 17-20 describe the fabrication and characterization of devices including examples of non-fullerene electron acceptors of the present disclosure.

EXAMPLES

Unless stated otherwise, starting materials were purchased and used without further purification. $^1$H NMR and $^{13}$C NMR spectra were recorded on a Bruker AV500 at 500 MHz using either deuterochloroform (CDCl$_3$) as the solvent. Mass spectra were obtained from Bruker AutoFlex II Matrix-Assisted LASER Desorption Ionization-Time of Flight Mass Spectrometer (MALDI-TOF) using benzo[α] pyrene as a matrix recorded in a (+)-reflector mode. Thermogravimetric analysis of the molecules was conducted on a TA Instruments model Q50TGA. A heating rate of 10° C./min under a flow of N$_2$ was used with runs conducted from room temperature to 800° C. Cyclic voltammetry was done on an EG&G Princeton Applied Research potentiostat/galvanostat (model 273A). Data were analyzed by using a Model 270 Electrochemical Analysis System Software on a PC computer. A three-electrode cell was used, using platinum wire electrodes as both counter and working electrode. Silver/silver ion (Ag in 0.1 M AgNO$_3$ solution, Bioanalytical System, Inc.) was used as a reference electrode. Ferrocene/ferrocenium (Fc/Fc$^+$) was used as an internal standard. All solutions were purged with N$_2$ for 20 min before each experiment. UV-Vis absorption spectra were collected on a Perkin-Elmer model Lambda 900 UV/Vis/near-IR spectrophotometer. The photoluminescence (PL) emission spectra were obtained with a Photon Technology International (PTI) Inc. model QM2001-4 spectrofluorimeter.

Example 1

Synthesis and Characterization of BrPh-BFI and BFI-P2

Scheme 3.

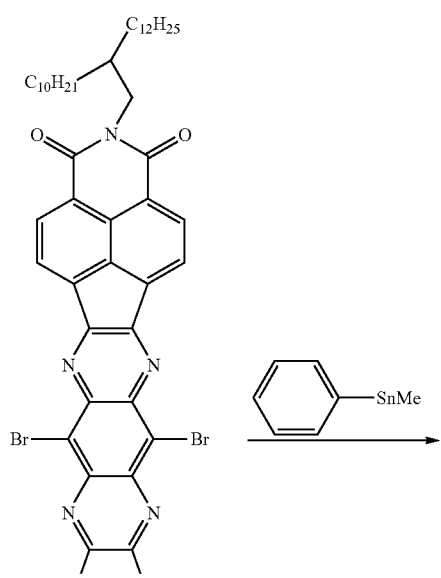

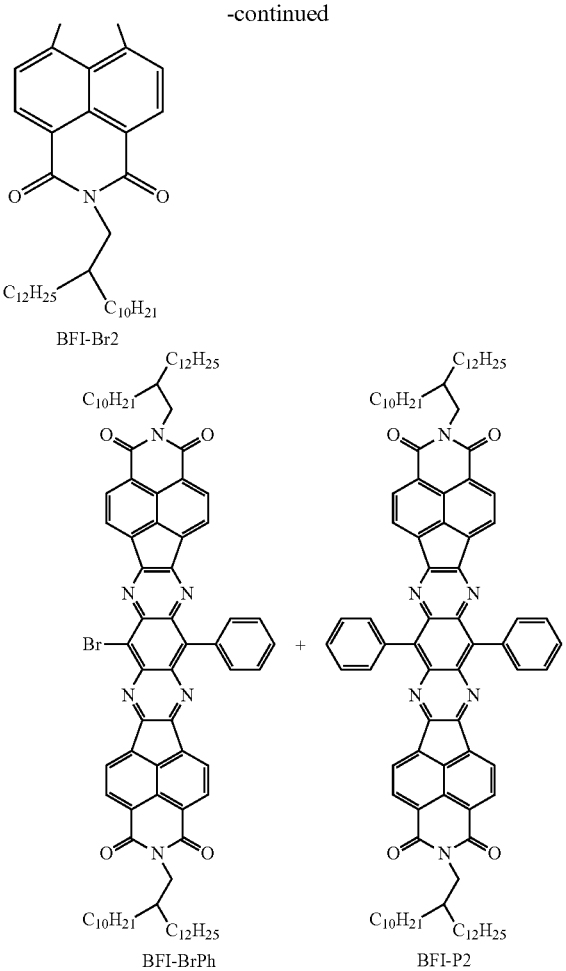

Under argon, 8,17-dibromo-7,9,16,18-tetraazabenzodifluoranthene-3,4,12,13-tetracarboxylic acid diimide (BFI-Br$_2$) (1.0 g, 0.71 mmole), trimethyl(phenyl)tin (172 mg, 0.71 mmole), Pd$_2$(dba)$_3$ (24 mg) and P($^o$ Tol)$_3$ (32 mg) were transferred into a Schlenk tube and dissolved in 50 mL of degassed toluene. The mixture was heated to reflux and kept stirring for 24 hours. After removing all the volatile materials, the solid residue was purified by chromatography with chloroform as the eluent. BFI-Br2 was synthesized according to the procedures described in Li, H. et al. *Angew. Chem. Int. Ed.* 2013, 52, 5513-5517, herein incorporated by reference in its entirety.

8,17-diphenyl-7,9,16,18-tetraazabenzodifluoranthene-3,4,12,13-tetracarboxylic acid diimide (BFI-P2) was isolated as a red solid. Yield: 380 mg, 38%. $^1$H NMR (CDCl$_3$, 25° C., 500 MHz): δ=8.47 (d, 4H, $^3$J=7.5 Hz, BFI), 8.16 (d, 4H, $^3$J=7.5 Hz, BFI), 7.82 (br, 4H, Ph), 7.70 (m, 6H, Ph), 3.87 (d, 4H, $^3$J=7.0 Hz, CH$_2$), 1.84 (br, 2H, CH), 1.4-1.0 (m, 80H, CH$_2$), 0.86 ppm (m, 12H, Me). $^{13}$C NMR (125 MHz, 25° C., CDCl$_3$): δ 135.8, 141.3, 138.1, 136.2, 136.0, 134.7, 133.4, 132.6, 128.0, 127.4, 125.0, 124.3, 123.2, 44.7, 37.0, 32.2, 32.1, 31.9, 30.3, 29.9, 29.9, 29.9, 29.6, 26.7, 22.9, 14.3 ppm; HRMS (m/z): [M]$^+$ calcd. for C$_{94}$H$_{116}$N$_6$O$_4$, 1393.91; found, 1394.55. Elemental analysis calcd for C$_{94}$H$_{116}$N$_6$O$_4$: C, 80.99%: H, 8.39%: N, 6.03%. found C, 80.95%: H, 8.33%: N, 5.93%.

8-bromo-17-phenyl-7,9,16,18-tetraazabenzodifluoranthene-3,4,12,13-tetracarboxylic acid diimide (BFI-BrPh)

was isolated as a red solid. Yield: 400 mg, 40%. $^1$H NMR (CDCl$_3$, 25° C., 500 MHz): δ=8.51 (d, 2H, $^3$J=7.5 Hz, BFI), 8.41 (d, 2H, $^3$J=7.0 Hz, BFI), 8.22 (d, 4H, $^3$J=7.5 Hz, BFI), 8.05 (br, 2H, Ph), 7.77 (m, 3H, Ph), 3.76 (d, $^3$J=6.0 Hz, 4H, CH$_2$), 1.79 (br, 2H, CH), 1.4-1.0 (m, 80H, CH$_2$), 0.87 ppm (m, 12H, Me). $^{13}$C NMR (125 MHz, 25° C., CDCl$_3$): δ 162.3, 162.2, 153.3, 153.2, 141.4, 137.9 136.8, 135.4, 134.6, 134.1, 133.7, 133.4, 132.5, 132.2, 128.3, 128.0, 127.2, 124.3, 124.2, 124.1, 123.6, 123.2, 44.0, 37.0, 32.2, 32.1, 31.6, 30.4, 30.0, 29.9, 29.6, 29.6, 26.4, 22.9, 14.4 ppm; HRMS (m/z): [M]$^+$ calcd. for C$_{88}$H$_{111}$BrN$_6$O$_4$, 1394.79; found, 1397.62.

BFI-P2 has good solubility in organic solvents including chloroform, toluene, dichloromethane, chlorobenzene, etc. Thermogravimetric analysis (TGA) showed BFI-P2 has excellent thermal stability with a thermal decomposition temperature at T$_d$=440° C.

The thin film absorption spectrum of BFI-P2 had an intense UV band centered at 373 nm with an absorption coefficient of 8.1×10$^4$ cm$^{-1}$ and a weak, broad, visible band centered at ~500 nm (α=1.2×10$^4$ cm$^{-1}$). The LUMO energy level of −3.62 eV for BFI-P2 is estimated from the reduction wave of the cyclic voltammograms.

Example 2

Organic Solar Cell Incorporating BFI-P2

Solar cells with device structure of ITO/PEDOT:PSS/active layer/LiF/Al were fabricated. ITO substrates (10Ω/□, Shanghai B. Tree Tech. Consult Co., Ltd, Shanghai, China) were cleaned sequentially with acetone, deionized water and isopropyl alcohol in an ultrasonic bath, and blown with nitrogen until dried. A 40 nm PEDOT:PSS (Clevios P VP AI 4083) layer was spin-coated on top of the ITO and dried at 150° C. for 10 min under vacuum. The active layer was then spin-coated from PSEHTT:BFI-P2 (1:4 wt/wt) mixture solution in chloroform to make a thin film of ~120 nm thickness and thermally annealed at 150° C. for 10 min in a glovebox. The substrates were then loaded in a thermal evaporator (BOC Edwards, 306) to deposit a cathode composed of 1.0 nm LiF and 90 nm Al under high vacuum (8×10$^{-7}$ Torr). Five solar cells, each with an active area of 4 mm$^2$, were fabricated per ITO substrate. The current density-voltage (J-V) curves of solar cells were measured using a HP4155A semiconductor parameter analyzer under laboratory ambient air conditions. An AM1.5 illumination at 100 mW/cm2 was provided by a filtered Xe lamp and calibrated by using an NREL-calibrated Si diode. The external quantum efficiency (EQE) was measured using a QEX10 solar cell quantum efficiency measurement system (PV Measurements, Inc.) and was calibrated with a NREL-certified Si diode before measurement. The solar cells gave a PCE=1.03%, short circuit density (J$_{sc}$)=2.31 mAcm$^{-2}$, open circuit voltage (V$_{oc}$)=0.9 V, and fill factor (FF)=49%.

Solar cells with the inverted device structure of ITO/ZnO/active layer/MoO$_3$/Ag were fabricated. ITO substrates were cleaned as the same procedure mentioned above, followed by oxygen plasma treatment. Zinc oxide (ZnO) precursor was prepared as described, for example, in Earmme, T., et al. J. Am. Chem. Soc. 2013, 135, 14960-14963, herein incorporated by reference in its entirety, spin-coated on top of the ITO and annealed at 250° C. for 1 hr in air. The ZnO film thickness was approximately 30 nm which is measured by the profilometer. The active layers were spin-coated from the PSEHTT:BFI-P2 (1:4 wt/wt) mixture solution in chloroform, respectively, and thermally annealed at 150° C. for 10 min in a glovebox. The substrates were then loaded in a thermal evaporator (BOC Edwards, 306) to deposit an anode composed of thin layer of 10.0 nm MoO$_3$ and 100 nm Ag under high vacuum (8×10$^{-7}$ Torr). Five solar cells, each with an active area of 4 mm$^2$, were fabricated per ITO substrate. The devices were characterized similarly as the conventional devices mentioned above. The organic solar cells had a PCE of 1.44% with J$_{sc}$=3.16 mAcm$^{-2}$, V$_{oc}$=0.94 V and FF=49%

Example 3

Transistors Incorporating BFI-P2

Field-effect transistors were fabricated on a heavily n-doped silicon substrate with thermally grown silicon dioxide gate insulator (200 nm; capacitance density (C$_i$)=17 nF/cm$^2$). Photolithographically defined gold patterns (40 nm) with chromium adhesive layer (2 nm) acted as the source and drain electrodes in the bottom-contact/bottom-gate transistors, forming the channel width (W) of 800 µm and length (L) of 40 µm (W/L=20). The substrates were cleaned by ultrasonication with acetone and isopropyl alcohol and dried by flow of nitrogen. The surface of a silicon dioxide substrate was further cleaned by plasma and treated with octyltrichlorosilane (OTS8) to form a hydrophobic self-assembled monolayer (SAM). BFI-P2 was deposited onto the substrate by spin-coating from a solution in chloroform. The devices were annealed at various temperatures under argon environment. Electrical characteristics of the devices were measured using an HP4145B semiconductor parameter analyzer under nitrogen atmosphere.

The charge carrier mobilities were calculated from transfer curves using the standard saturation equation of metal-oxide-semiconductor field-effect transistors: Ids=(µWCo/2L)(Vg−Vt)$^2$. The electron mobility of up to 0.5 cm$^2$ V$^{-1}$ s$^{-1}$ was obtained for transistors based on BFI-P2.

Example 4

Synthesis and Characterization of Compound DBFI-T

Scheme 4.

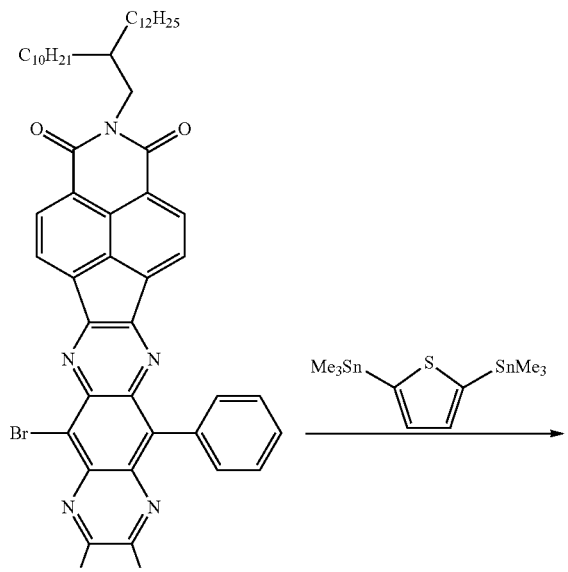

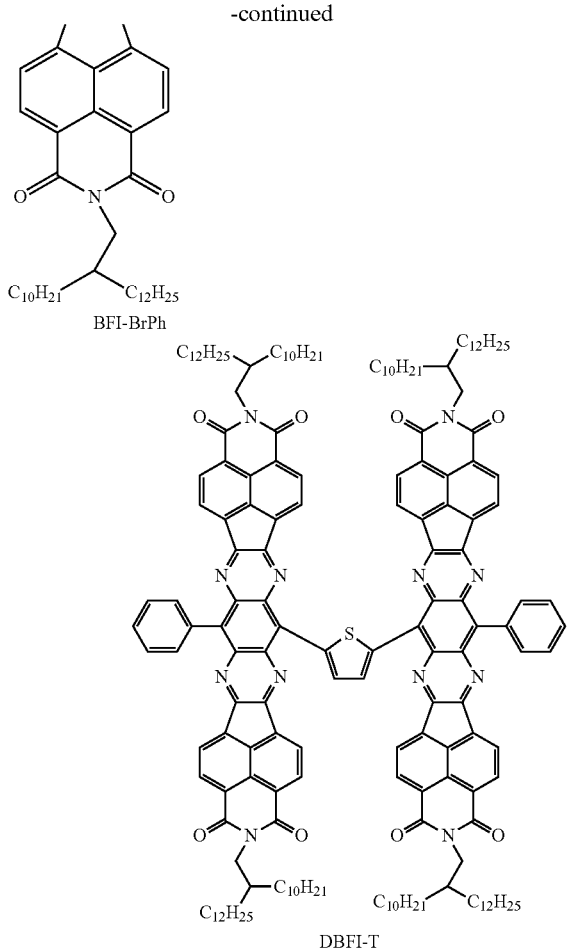

BFI-BrPh

DBFI-T

Synthesis of 2,5-bis(8-(17-phenyl)-7,9,16,18-tetraazabenzodifluoranthene-3,4,12,13-tetracarboxylic acid diimide) thiophene (DBFI-T). Under argon, 8-bromo-17-phenyl-7,9,16,18-tetraazabenzodifluoranthene-3,4,12,13-tetracarboxylic acid diimide (BFI-BrPh) (380 mg, 0.27 mmole), 2,5-bis(trimethylstannyl)thiophene (55.0 mg, 0.13 mmole), Pd$_2$(dba)$_3$ (9 mg) and P(oTol)$_3$ (12 mg) were transferred into a Schlenk tube and dissolved in 16 mL of degassed toluene. The mixture was heated to reflux and kept stirring for 72 hours. After removing all the volatile materials, the solid residue was purified by chromatography with chloroform and a few drops of methanol as the eluent. The product was isolated as a green solid. Yield: 200 mg, 54.9%. [$^1$H NMR (CDCl$_3$, 25° C., 500 MHz): δ=9.06 (s, 2H, Th), 8.74 (d, 2H, $^3$J=7.5 Hz, BFI), 8.65 (d, 2H, $^3$J=7.5 Hz, BFI), 8.55 (d, 4H, $^3$J=7.0 Hz, BFI), 8.32 (d, 2H, $^3$J=7.5 Hz, BFI+Ph), 8.27 (d, 2H, $^3$J=7.0 Hz, BFI+Ph), 8.14 (d, 2H, $^3$J=7.0 Hz, BFI), 8.00 (d, 4H, $^3$J=7.5 Hz, BFI), 7.87 (t, 4H, Ph), 7.79 (d, 4H, $^3$J=7.0 Hz, BFI), 4.14 (br, 4H, CH2), 3.31 (br, 2H, CH2), 2.97 (br, 2H, CH$_2$), 2.00 (br, 2H, CH), 1.63 (br, 2H, CH), 1.5-0.75 (m, 172H, CH$_2$+CH$_3$); HRMS (m/z): [M]$^+$ calcd. for C$_{180}$H$_{224}$N$_{12}$O$_8$S, 2714.12; found, 2713.61. Elemental analysis calcd for C$_{180}$H$_{224}$N$_{12}$O$_8$S, C, 79.60%: H, 8.31%: N, 6.19%. found C, 79.71%: H, 8.35%: N, 6.03%.

DBFI-T has good solubility in organic solvents including chloroform, toluene, dichloromethane, chlorobenzene, etc. Thermogravimetric analysis (TGA) showed DBFI-S has excellent thermal stability with a thermal decomposition temperature at T$_d$=430° C.

The thin film absorption spectrum of DBFI-T has an intense UV band ($\lambda_{max}$=384 nm, α=6.1×10$^4$ cm$^{-1}$) and a very broad visible band centered near 600 nm (α=7.1=10$^3$ cm$^{-1}$). The LUMO energy level of −3.77 eV for DBFI-T is estimated from the reduction wave of the cyclic voltammograms.

Example 5

Organic Solar Cell Incorporating PSEHTT:DBFI-T

Solar cells with device structure of ITO/PEDOT:PSS/active layer/LiF/Al were fabricated. ITO substrates (10Ω/□, Shanghai B. Tree Tech. Consult Co., Ltd, Shanghai, China) were cleaned sequentially with acetone, deionized water and isopropyl alcohol in an ultrasonic bath, and blown with nitrogen until dried. A 40 nm PEDOT:PSS (Clevios P VP AI 4083) layer was spin-coated on top of the ITO and dried at 150° C. for 10 min under vacuum. The active layer was then spin-coated from PSEHTT:DBFI-T (1:2 wt/wt) mixture solution in chloroform to make a thin film of ~120 nm thickness and thermally annealed at 150° C. for 10 min in a glovebox. The substrates were then loaded in a thermal evaporator (BOC Edwards, 306) to deposit a cathode composed of 1.0 nm LiF and 90 nm Al under high vacuum (8×10$^{-7}$ Torr). Five solar cells, each with an active area of 4 mm$^2$, were fabricated per ITO substrate. The current density-voltage (J-V) curves of solar cells were measured using a HP4155A semiconductor parameter analyzer under laboratory ambient air conditions. An AM1.5 illumination at 100 mW/cm2 was provided by a filtered Xe lamp and calibrated by using an NREL-calibrated Si diode. The external quantum efficiency (EQE) was measured using a QEX10 solar cell quantum efficiency measurement system (PV Measurements, Inc.) and was calibrated with a NREL-certified Si diode before measurement. The solar cells gave high PCE=4.24%, J$_{sc}$=9.82 mAcm$^{-2}$, V$_{oc}$=0.82 V, and FF=57%.

BHJ solar cells with the inverted structure of ITO/ZnO/active layer/MoO$_3$/Ag were fabricated. ITO substrates were cleaned similarly as above. Zinc oxide (ZnO) precursor was prepared Zinc oxide (ZnO) precursor was prepared as described, for example, in Earmme, T., et al., J. Am. Chem. Soc. 2013, 135, 14960-14963, herein incorporated by reference in its entirety, spin-coated on top of the ITO and annealed at 250° C. for 1 hr in air. The ZnO film thickness (~30 nm) was measured with a profilometer. ZnO surface modification was conducted by spin-coating a solution of ethanolamine in 2-methoxyethanol (1 vol %) followed by drying at 110° C. for 10 min. The PSEHTT:DBFI-T active layers were spin coated from a PSEHTT:DBFI-T (1:2 wt/wt) blend solutions in chloroform and thermally annealed at 175° C. for 10 min. The substrates were then loaded in a thermal evaporator (BOC Edwards, 306) to deposit an anode composed of thin layer (10.0 nm) of MoO$_3$ and 100 nm Ag under high vacuum (8 ther$^{-7}$ Torr). The devices were tested similarly as the conventional solar cells.

Five solar cells, each with an active area of 4 mm$^2$, were fabricated per ITO substrate. The devices were characterized similarly as the conventional devices mentioned above. The organic solar cells had a PCE of 5.04% with J$_{sc}$=10.14 mAcm$^{-2}$, V$_{oc}$=0.86 V and FF=58%.

Example 6

Organic Solar Cell Incorporating P3HT:DBFI-T

BHJ solar cells with the inverted structure of ITO/ZnO/active layer/MoO$_3$/Ag were fabricated. ITO substrates were cleaned similarly as above. Zinc oxide (ZnO) precursor was prepared as described, for example, in Earmme, T., et al. *J. Am. Chem. Soc.* 2013, 135, 14960-14963, herein incorporated by reference in its entirety, spin-coated on top of the ITO and annealed at 250° C. for 1 hr in air. The ZnO film thickness (~30 nm) was measured with a profilometer. ZnO surface modification was conducted by spin-coating a solution of ethanolamine in 2-methoxylethanol (1 vol %) followed by drying at 110° C. for 10 min. The P3HT:DBFI-T active layers were spin coated from a P3HT:DBFI-T (1:1.5 wt/wt) blend solutions in chloroform and thermally annealed at 175° C. for 10 min in a glovebox. The substrates were then loaded in a thermal evaporator (BOC Edwards, 306) to deposit an anode composed of thin layer (10.0 nm) of $MoO_3$ and 100 nm Ag under high vacuum ($8\times10^{-7}$ Torr). Five solar cells, each with an active area of 4 $mm^2$, were fabricated per ITO substrate. The devices were characterized similarly as the conventional devices mentioned above. The organic solar cells had a PCE of 2.33% with $J_{sc}$=7.36 $mAcm^{-2}$, $V_{oc}$=0.59 V and FF=54%.

Example 7

Organic Solar Cell Incorporating PBDTT-FTTE:DBFI-T

Solar cells with the inverted device structure of ITO/ZnO/active layer/$MoO_3$/Ag were fabricated. ITO substrates were cleaned as the same procedure mentioned above, followed by oxygen plasma treatment. Zinc oxide (ZnO) precursor was prepared as described, for example, in Earmme, T., et al. *J. Am. Chem. Soc.* 2013, 135, 14960-14963, herein incorporated by reference in its entirety, spin-coated on top of the ITO and annealed at 250° C. for 1 hr in air. The ZnO film thickness was approximately 30 nm which is measured by the profilometer. ZnO surface modification was conducted by spin-coating a solution of ethanolamine in 2-methoxylethanol (1 vol %) followed by drying at 110° C. for 10 min. The active layers were spin-coated from the PBDTT-FTTE:DBFI-T (1:2 wt/wt) mixture solution in chlorobenzene and dichlorobenzene mixture (9:1 v/v), respectively. The substrates were then loaded in a thermal evaporator (BOC Edwards, 306) to deposit an anode composed of thin layer of 10.0 nm $MoO_3$ and 100 nm Ag under high vacuum ($8\times10^{-7}$ Torr). Five solar cells, each with an active area of 4 $mm^2$, were fabricated per ITO substrate. The devices were characterized similarly as the conventional devices mentioned above. The organic solar cells had a PCE of 2.60% with $J_{sc}$=7.76 $mAcm^{-2}$, $V_{oc}$=0.97 V and FF=35%.

Example 8

Transistors Incorporating DBFI-T

Field-effect transistors were fabricated on a heavily n-doped silicon substrate with thermally grown silicon dioxide gate insulator (200 nm; capacitance density, $C_i$=17 $nF/cm^2$). Photolithographically defined gold patterns (40 nm) with chromium adhesive layer (2 nm) acted as the source and drain electrodes in the bottom-contact/bottom-gate transistors, forming the channel width (W) of 800 μm and length (L) of 40 μm (W/L=20). The substrates were cleaned by ultrasonication with acetone and isopropyl alcohol and dried by flow of nitrogen. The surface of a silicon dioxide substrate was further cleaned by plasma and treated with octyltrichlorosilane (OTS8) to form a hydrophobic self-assembled monolayer (SAM). DBFI-T was deposited onto the substrate by spin-coating from a solution in chloroform. The devices were annealed at various temperatures under argon environment. Electrical characteristics of the devices were measured using an HP4145B semiconductor parameter analyzer under nitrogen atmosphere.

The charge carrier mobilities were calculated from transfer curves using the standard saturation equation of metal-oxide-semiconductor field-effect transistors: $Ids=(\mu WC_o/2L)(Vg-Vt)^2$. The electron mobility of up to 0.006 $cm^2 V^{-1} s^{-1}$ was obtained for transistors based on DBFI-T.

Example 9

Synthesis and Characterization of Compound DBFI-S

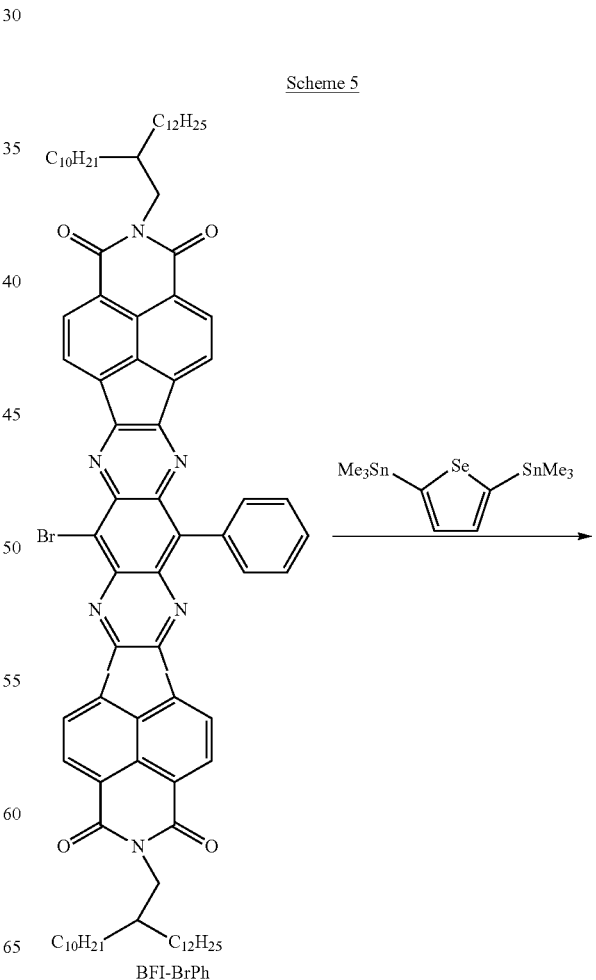

Scheme 5

BFI-BrPh

-continued

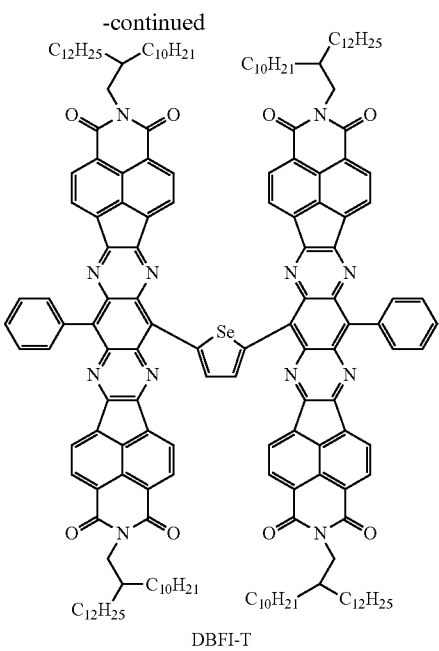

DBFI-T

Synthesis of 2,5-bis(8-(17-phenyl)-7,9,16,18-tetraazabenzodifluoranthene-3,4,12,13-tetracarboxylic acid diimide)selenophene (DBFI-S)

Under argon, BFI-BrPh (140 mg, 0.10 mmole), 2,5-bis(trimethylstannyl)selenophene (22.0 mg, 0.05 mmole), $Pd_2(dba)_3$ (9 mg) and $P(^oTol)_3$ (12 mg) were transferred into a Schlenk tube and dissolved in 10 mL of degassed toluene. The mixture was heated to reflux and kept stirring for 72 hours. After removing all the volatile materials, the solid residue was purified by chromatography with chloroform and a few drops of methanol as the eluent. The product was isolated as a green solid. Yield: 72 mg, 52.0%. $^1$H NMR ($CDCl_3$, 0° C., 500 MHz): δ=9.33 (s, 2H, Th), 8.66 (m, 6H), 8.64 (2H), 8.30 (d, 4H), 8.16 (s, 2H), 8.03 (m, 4H), 7.86 (m, 4H), 7.67 (s, 2H), 7.38 (s, 2H), 4.14 (br, 4H, CH2), 3.31 (br, 2H, CH2), 2.97 (br, 2H, $CH_2$), 2.00 (br, 2H, CH), 1.63 (br, 2H, CH), 1.5-0.75 (m, 186H, $CH_2+CH_3$). HRMS (m/z): $[M]^+$ calcd. for $C_{180}H_{224}N_{12}O_8Se$, 2763.67; found, 2761.64. Elemental analysis calcd for $C_{180}H_{224}N_{12}O_8Se$, C, 78.25%: H, 8.17%: N, 6.08%. found C, 78.13%: H, 8.10%: N, 5.99%.

DBFI-S has good solubility in organic solvents including chloroform, toluene, dichloromethane, chlorobenzene, etc. Thermogravimetric analysis (TGA) showed DBFI-S has excellent thermal stability with a thermal decomposition temperature at $T_d$=394° C.

The thin film absorption spectrum of DBFI-S has an intense UV band ($λ_{max}$=386 nm, α=7.5×10$^4$ cm$^{-1}$) and a very broad visible band centered near 590 nm (α=8.2×10$^3$ cm$^{-1}$). The LUMO energy level of −3.70 eV for DBFI-S is estimated from the reduction wave of the cyclic voltammograms.

Example 10

Organic Solar Cell Based on Compound DBFI-S

Solar cells with device structure of ITO/PEDOT:PSS/active layer/LiF/Al were fabricated. ITO substrates (10Ω/□, Shanghai B. Tree Tech. Consult Co., Ltd, Shanghai, China) were cleaned sequentially with acetone, deionized water and isopropyl alcohol in an ultrasonic bath, and blown with nitrogen until dried. A 40 nm PEDOT:PSS (Clevios P VP AI 4083) layer was spin-coated on top of the ITO and dried at 150° C. for 10 min under vacuum. The active layer was then spin-coated from PSEHTT:DBFI-S (1:2 wt/wt) mixture solution in chloroform to make a thin film of ~120 nm thickness and thermally annealed at 150° C. for 10 min in a glovebox. The substrates were then loaded in a thermal evaporator (BOC Edwards, 306) to deposit a cathode composed of 1.0 nm LiF and 90 nm Al under high vacuum (8×10$^{-7}$ Torr). Five solar cells, each with an active area of 4 mm$^2$, were fabricated per ITO substrate. The current density-voltage (J-V) curves of solar cells were measured using a HP4155A semiconductor parameter analyzer under laboratory ambient air conditions. An AM1.5 illumination at 100 mW/cm$^2$ was provided by a filtered Xe lamp and calibrated by using an NREL-calibrated Si diode. The external quantum efficiency (EQE) was measured using a QEX10 solar cell quantum efficiency measurement system (PV Measurements, Inc.) and was calibrated with a NREL-certified Si diode before measurement. The solar cells gave high PCE=1.04%, $J_{sc}$=3.53 mAcm$^{-2}$, $V_{oc}$=0.70 V, and FF=42%.

Solar cells with the inverted device structure of ITO/ZnO/active layer/MoO$_3$/Ag were fabricated. ITO substrates were cleaned as the same procedure mentioned above, followed by oxygen plasma treatment. Zinc oxide (ZnO) precursor was prepared as described, for example, in Earmme, T., et al. *J. Am. Chem. Soc.* 2013, 135, 14960-14963, herein incorporated by reference in its entirety, spin-coated on top of the ITO and annealed at 250° C. for 1 hr in air. The ZnO film thickness was approximately 30 nm which is measured by the profilometer. The active layers were spin-coated from the PSEHTT:DBFI-S (1:2 wt/wt) mixture solution in chloroform, respectively, and thermally annealed at 150° C. for 10 min in a glovebox. The substrates were then loaded in a thermal evaporator (BOC Edwards, 306) to deposit an anode composed of thin layer of 10.0 nm MoO$_3$ and 100 nm Ag under high vacuum (8×10$^{-7}$ Torr). Five solar cells, each with an active area of 4 mm$^2$, were fabricated per ITO substrate. The devices were characterized similarly as the conventional devices mentioned above. The organic solar cells had a PCE of 1.00% with $J_{sc}$=2.99 mAcm$^{-2}$, $V_{oc}$=0.71 V and FF=47%.

Example 11

Transistors Incorporating DBFI-S

Field-effect transistors were fabricated on a heavily n-doped silicon substrate with thermally grown silicon dioxide gate insulator (200 nm; capacitance density, $C_i$=17 nF/cm$^2$). Photolithographically defined gold patterns (40 nm) with chromium adhesive layer (2 nm) acted as the source and drain electrodes in the bottom-contact/bottom-gate transistors, forming the channel width (W) of 800 μm and length (L) of 40 μm (W/L=20). The substrates were cleaned by ultrasonication with acetone and isopropyl alcohol and dried by flow of nitrogen. The surface of a silicon dioxide substrate was further cleaned by plasma and treated with octyltrichlorosilane (OTS8) to form a hydrophobic self-assembled monolayer (SAM). DBFI-S was deposited onto the substrate by spin-coating from a solution in chloroform. The devices were annealed at various temperatures under argon environment. Electrical characteristics of the devices were measured using an HP4145B semiconductor parameter analyzer under nitrogen atmosphere.

The charge carrier mobilities were calculated from transfer curves using the standard saturation equation of metal-oxide-semiconductor field-effect transistors: $Ids=(\mu WCo/2L)(Vg-Vt)^2$. (Kang, S.-M., Leblebici, Y. *CMOS Digital Integrated Circuits: Analysis and Design*, McGraw-Hill, New York, 1996.) The electron mobility of up to $10^{-5}$ cm$^2$ V$^{-1}$ s$^{-1}$ was obtained for transistors based on DBFI-S.

Example 12

Synthesis and Characterization of Compound DBFI-DMT

Scheme 6

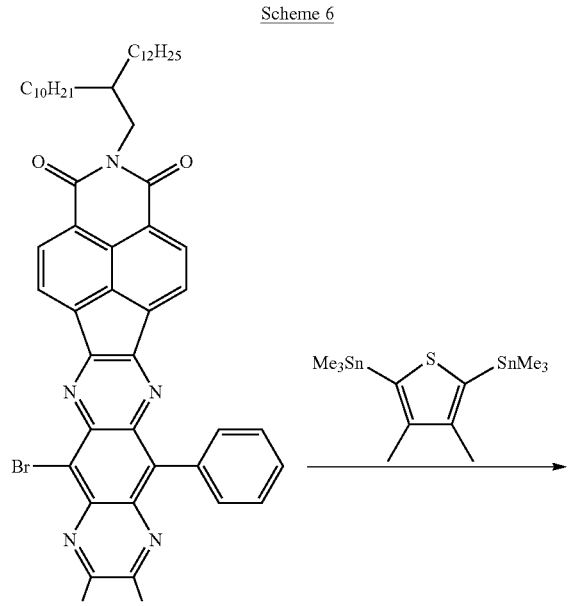

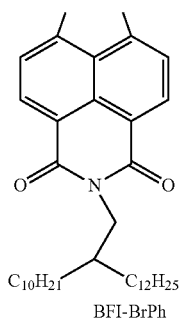

BFI-BrPh

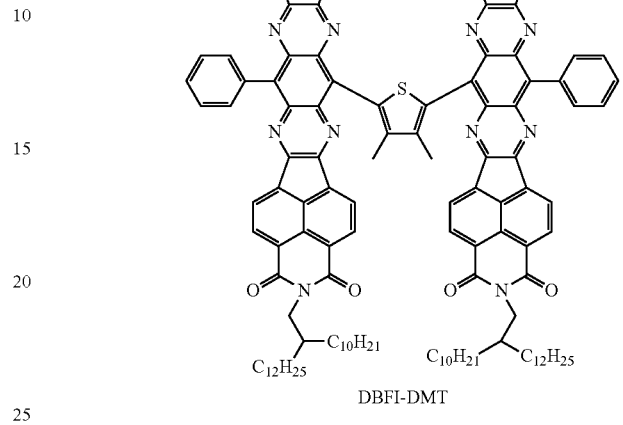

DBFI-DMT

Synthesis of 2,5-bis(8-(17-phenyl)-7,9,16,18-tetraazabenzodifluoranthene-3,4,12,13-tetracarboxylic acid diimide)-3,4-dimethylthiophene (DBFI-DMT)

Under argon, BFI-BrPh (200 mg, 0.14 mmole), 3,4-dimethyl-2,5-bis(trimethylstannyl)thiophene (31.5 mg, 0.07 mmole), Pd$_2$(dba)$_3$ (9 mg) and P($^o$Tol)$_3$ (12 mg) were transferred into a Schlenk tube and dissolved in 14 mL of degassed toluene. The mixture was heated to reflux and kept stirring for 72 hours. After removing all the volatile materials, the solid residue was purified by chromatography with chloroform and a few drops of methanol as the eluent. The product was isolated as a green solid. Yield: 121 mg, 61.5%. HRMS (m/z): [M]$^+$ calcd. for C$_{182}$H$_{228}$N$_{12}$O$_8$S, 2742.76; found, 2742.31.

DBFI-DMT has good solubility in organic solvents including chloroform, toluene, dichloromethane, chlorobenzene, etc. Thermogravimetric analysis (TGA) showed DBFI-DMT has excellent thermal stability with a thermal decomposition temperature at T$_d$=417° C.

The thin film absorption spectrum of DBFI-DMT has an intense UV band ($\lambda_{max}$=381 nm, $\alpha$=6.3×10$^4$ cm$^{-1}$) and a low-energy band centered near 510 nm ($\alpha$=6.7×10$^3$ cm$^{-1}$). The LUMO energy level of −3.6 eV for DBFI-DMT is estimated from the reduction wave of the cyclic voltammograms.

Example 13

Organic Solar Cell Incorporating DBFI-DMT

BHJ solar cells with the inverted structure of ITO/ZnO/active layer/MoO$_3$/Ag were fabricated. ITO substrates were cleaned similarly as above. Zinc oxide (ZnO) precursor was prepared as described, for example, in Earmme, T., et al. *J. Am. Chem. Soc.* 2013, 135, 14960-14963, herein incorporated by reference in its entirety, spin-coated on top of the ITO and annealed at 250° C. for 1 hr in air. The ZnO film thickness (~30 nm) was measured with a profilometer. ZnO surface modification was conducted by spin-coating a solution of ethanolamine in 2-methoxyethanol (1 vol %) followed by drying at 110° C. for 10 min. The PSEHTT:DBFI-DMT active layers were spin-coated from the PSEHTT:DBFI-DMT (1:2 wt/wt) blend solutions in chloroform, respectively, and thermally annealed at 175° C. for 10 min in a glovebox. The substrates were then loaded in a thermal evaporator (BOC Edwards, 306) to deposit an anode composed of thin layer (10.0 nm) of MoO$_3$ and 100 nm Ag under high vacuum (8×10$^{-7}$ Torr). Five solar cells, each with an active area of 4 mm$^2$, were fabricated per ITO substrate. The devices were characterized similarly as the conventional devices mentioned above. The organic solar cells had a PCE of 5.02% with J$_{sc}$=9.51 mAcm$^{-2}$, V$_{oc}$=0.86 V and FF=62%.

Example 14

Synthesis and Characterization of DBFI-EDOT

Scheme 7

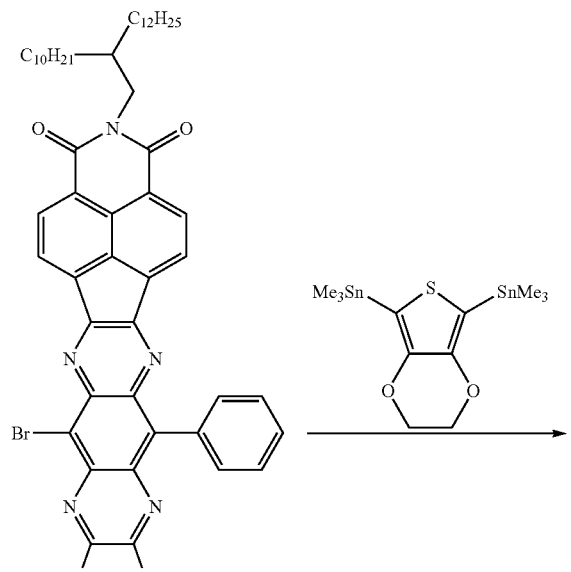

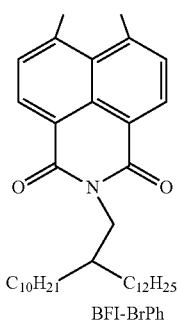

BFI-BrPh

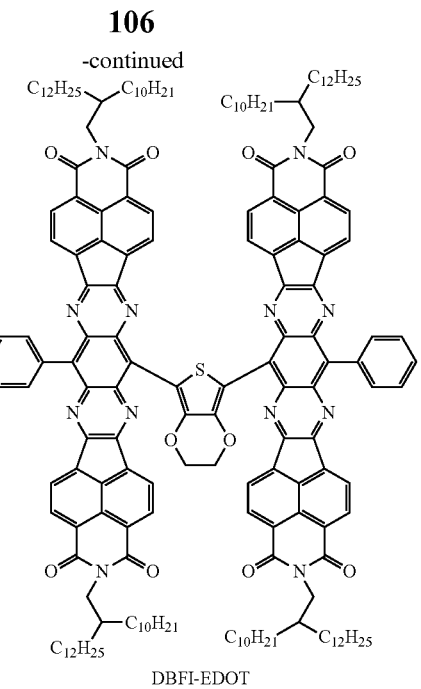

DBFI-EDOT

Synthesis of 2,5-bis(8-(17-phenyl)-7,9,16,18-tetraazabenzodifluoranthene-3,4,12,13-tetracarboxylic acid diimide)-3,4-ethylenedioxythiophene (DBFI-EDOT)

Under argon, BFI-BrPh (200 mg, 0.14 mmole), 3,4-dimethyl-2,5-bis(trimethylstannyl)thiophene (33.5 mg, 0.07 mmole), Pd$_2$(dba)$_3$ (9 mg) and P($^o$Tol)$_3$ (12 mg) were transferred into a Schlenk tube and dissolved in 14 mL of degassed toluene. The mixture was heated to reflux and kept stirring for 72 hours. After removing all the volatile materials, the solid residue was purified by chromatography with chloroform and a few drops of methanol as the eluent. The product was isolated as a green solid. Yield: 109 mg, 54.8%. HRMS (m/z): [M]$^+$ calcd. for C$_{182}$H$_{226}$N$_{12}$O$_{10}$S, 2772.73; found, 2773.39.

DBFI-EDOT has good solubility in organic solvents including chloroform, toluene, dichloromethane, chlorobenzene, etc. Thermogravimetric analysis (TGA) showed DBFI-EDOT has excellent thermal stability with a thermal decomposition temperature at T$_d$=421° C.

The thin film absorption spectrum of DBFI-EDOT has an intense UV band ($\lambda_{max}$=391 nm, $\alpha$=6.5×10$^4$ cm$^{-1}$) and a low-energy band centered near 614 nm ($\alpha$=7.1×10$^3$ cm$^{-1}$). The LUMO energy level of −3.7 eV for DBFI-EDOT is estimated from the reduction wave of the cyclic voltammograms.

Example 15

Organic Solar Cell Incorporating DBFI-EDOT

BHJ solar cells with the inverted structure of ITO/ZnO/active layer/MoO$_3$/Ag were fabricated. ITO substrates were cleaned similarly as above. Zinc oxide (ZnO) precursor was prepared as described, for example, in Earmme, T., et al. *J. Am. Chem. Soc.* 2013, 135, 14960-14963, herein incorporated by reference in its entirety, spin-coated on top of the ITO and annealed at 250° C. for 1 hr in air. The ZnO film thickness (~30 nm) was measured with a profilometer. ZnO surface modification was conducted by spin-coating a solution of ethanolamine in 2-methoxylethanol (1 vol %) followed by drying at 110° C. for 10 min. The PSEHTT:DBFI-EDOT active layers were spin-coated from the PSEHTT:DBFI-EDOT (1:2 wt/wt) blend solutions in chloroform, respectively, and thermally annealed at 175° C. for 10 min in a glovebox. The substrates were then loaded in a thermal evaporator (BOC Edwards, 306) to deposit an anode composed of thin layer (10.0 nm) of MoO$_3$ and 100 nm Ag under high vacuum (8×10$^{-7}$ Torr). Five solar cells, each with an active area of 4 mm$^2$, were fabricated per ITO substrate. The devices were characterized similarly as the conventional devices mentioned above. The organic solar cells had a PCE of 4.86% with J$_{sc}$=9.23 mAcm$^{-2}$, V$_{oc}$=0.86 V and FF=61%.

Example 16

Synthesis and Characterization of Compound BNIDPA

Scheme 8

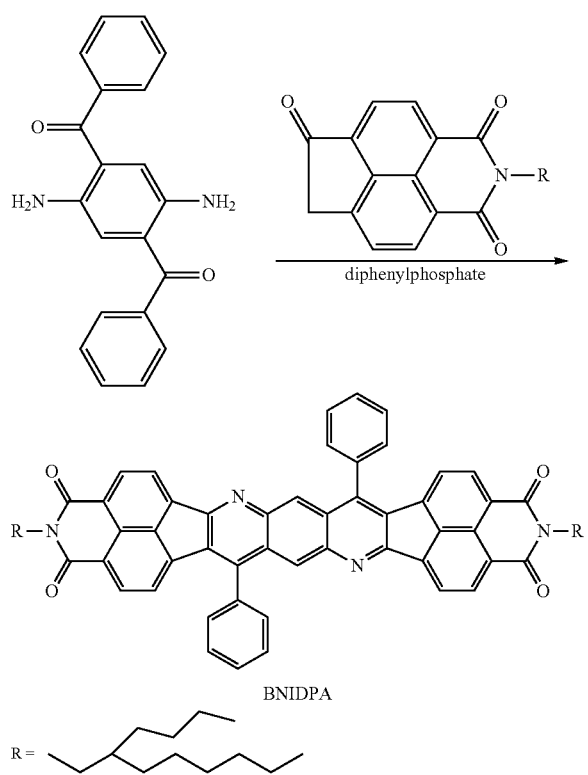

Synthesis of 2,3,6,7-bis(N-2'-butyloctyl-1",8"-naphthalene-4",5"-dicarboxylicimide)-3,6-diphenyl-1,4-anthrazoline (BNIDPA)

Inside a reaction tube, monoketone mixture 2 (222 mg, 0.25 mmol, 50%), (2,5-diamino-1,4-phenylene)bis(phenylmethanone) (39 mg, 0.12 mmol) and diphenyl phosphate (800 mg) were mixed with 5 mL of toluene. The mixture was slowly warmed up to 110° C. and kept stirring overnight. After cooling back to room temperature, the dark red solution was precipitated into 80 mL of methanol and triethylamine mixed solvents (2:1, v/v). A red solid formed which was collected and washed with 3×20 mL of methanol. The solid was further purified by column chromatography with CHCl$_3$ as the eluent solvent. Yield: 91 mg (69.9%). $^1$H NMR (CDCl$_3$, 500 MHz): δ=8.27 (d, 2H, $^3$J=7.5 Hz, Np), 8.23 (s, 2H, An), 7.91 (t, 4H, $^3$J=7.5 Hz, Ph), 7.83 (t, 6H, $^3$J=7.5 Hz, Ph), 7.73 (d, 2H, $^3$J=6.5 Hz, Np), 7.45 (d, 2H, $^3$J=8.0 Hz, Np), 6.97 (d, 2H, $^3$J=7.5, Np), 4.10 (d, 4H, $^3$J=7.0 Hz, CH$_2$), 1.90 (m, 2H, CH), 1.4-1.2 (m, 32H, CH$_2$), 1.0-0.8 (m, 12H, CH$_3$). $^{13}$C NMR (CDCl$_3$, 125.7 MHz): 163.5, 163.3, 159.9, 144.1, 144.0, 138.4, 138.3, 134.8, 134.3, 132.4, 130.9, 130.0, 129.8, 129.4, 129.2, 128.6, 127.8, 124.7, 123.2, 122.9, 122.2, 120.9, 44.7, 36.9, 32.1, 32.0, 31.6, 30.0, 29.0, 26.8, 23.3, 22.9, 14.3; HRMS (m/z): [M]$^+$ calcd. for C$_{72}$H$_{70}$N$_4$O$_4$, 1054.54; found, 1055.50. Elemental analysis calcd for C$_{80}$H$_{86}$N$_4$O$_4$, C, 81.94%: H, 6.69%: N, 5.31%. found C, 81.38%: H, 6.71%: N, 5.10%.

BNIDPA has good solubility in organic solvents including chloroform, toluene, dichloromethane, chlorobenzene, etc. BNIDPAs have multiple absorption bands in the wide range from 320 nm to 540 nm with peaks at λ$_{max}$=507, 474, 444, 410 380 (highest) and 363 nm. The LUMO energy level of −3.56 eV determined from cyclic voltammetry.

Example 17

Organic Solar Cell Incorporating PSEHTT:BNIDPA

BHJ solar cells with the inverted structure of ITO/ZnO/active layer/MoO$_3$/Ag were fabricated. ITO substrates were cleaned similarly as above. Zinc oxide (ZnO) precursor was prepared as described, for example, in Earmme, T., et al. *J. Am. Chem. Soc.* 2013, 135, 14960-14963, herein incorporated by reference in its entirety, spin-coated on top of the ITO and annealed at 250° C. for 1 hr in air. The ZnO film thickness (~30 nm) was measured with a profilometer. ZnO surface modification was conducted by spin-coating a solution of ethanolamine in 2-methoxylethanol (1 vol %) followed by drying at 110° C. for 10 min. The PSEHTT:BNIDPA active layers were spin-coated from the PSEHTT:BNIDPA (1:4 wt/wt) blend solutions in chloroform, respectively, and thermally annealed at 175° C. for 10 min in a glovebox. The substrates were then loaded in a thermal evaporator (BOC Edwards, 306) to deposit an anode composed of thin layer (10.0 nm) of MoO$_3$ and 100 nm Ag under high vacuum (8×10$^{-7}$ Torr). Five solar cells, each with an active area of 4 mm$^2$, were fabricated per ITO substrate. The devices were characterized similarly as the conventional devices mentioned above. The organic solar cells had a PCE of 3.02% with J$_{sc}$=6.64 mAcm$^{-2}$, V$_{oc}$=0.94 V and FF=48%.

Example 18

Organic Solar Cell Incorporating PBDTT-FTTE:BNIDPA

BHJ solar cells with the inverted structure of ITO/ZnO/active layer/MoO$_3$/Ag were fabricated. ITO substrates were cleaned similarly as above. Zinc oxide (ZnO) precursor was prepared as described, for example, in Earmme, T., et al. *J. Am. Chem. Soc.* 2013, 135, 14960-14963, herein incorporated by reference in its entirety, spin-coated on top of the ITO and annealed at 250° C. for 1 hr in air. The ZnO film thickness (~30 nm) was measured with a profilometer. ZnO surface modification was conducted by spin-coating a solution of ethanolamine in 2-methoxylethanol (1 vol %) followed by drying at 110° C. for 10 min. The PBDTT-FTTE:BNIDPA active layers were spin-coated from the PBDTT- FTTE:BNIDPA (1:4 wt/wt) blend solutions in chlorobenzene and dichlorobenzene (9:1 v/v). The substrates were then loaded in a thermal evaporator (BOC Edwards, 306) to deposit an anode composed of thin layer (10.0 nm) of $MoO_3$ and 100 nm Ag under high vacuum ($8 \times 10^{-7}$ Torr). Five solar cells, each with an active area of 4 $mm^2$, were fabricated per ITO substrate. The devices were characterized similarly as the conventional devices mentioned above. The organic solar cells had a PCE of 3.00% with $J_{sc}$=9.02 $mAcm^{-2}$, $V_{oc}$=0.96 V and FF=35%.

Example 19

Organic Solar Cell Incorporating PTB7:BNIDPA

BHJ solar cells with the inverted structure of ITO/ZnO/active layer/$MoO_3$/Ag were fabricated. ITO substrates were cleaned similarly as above. Zinc oxide (ZnO) precursor was prepared as described, for example, in Earmme, T., et al. *J. Am. Chem. Soc.* 2013, 135, 14960-14963, herein incorporated by reference in its entirety, spin-coated on top of the ITO and annealed at 250° C. for 1 hr in air. The ZnO film thickness (~30 nm) was measured with a profilometer. ZnO surface modification was conducted by spin-coating a solution of ethanolamine in 2-methoxylethanol (1 vol %) followed by drying at 110° C. for 10 min. The PTB7:BNIDPA active layers were spin-coated from the PTB7:BNIDPA (1:3 wt/wt) blend solutions in chlorobenzene and dichlorobenzene (9:1 v/v). The substrates were then loaded in a thermal evaporator (BOC Edwards, 306) to deposit an anode composed of thin layer (10.0 nm) of $MoO_3$ and 100 nm Ag under high vacuum ($8 \times 10^{-7}$ Torr). Five solar cells, each with an active area of 4 $mm^2$, were fabricated per ITO substrate. The devices were characterized similarly as the conventional devices mentioned above. The organic solar cells had a PCE of 3.08% with $J_{sc}$=8.23 $mAcm^2$, $V_{oc}$=0.98 V and FF=39%.

Example 20

3D Benzodifluoranthene Diimide Acceptors

Two related π-conjugated molecules, one with 1D and the other with 3D architecture, were synthesized to explore the effects of dimensionality on non-fullerene electron acceptors for OPVs. The linear 8,17-diphenyl-7,9,16,18-tetraazabenzodifluoranthene-3,4,12,13-tetracarboxylic acid diimide (BFI-P2) molecule (FIG. 1A) was synthesized by Stille coupling reaction of electron deficient 8,17-dibromo-7,9,16,18-tetraazabenzodifluoranthene-3,4,12,13-tetracarboxylic acid diimide (BFI-Br2) building block, as described, for example in EXAMPLE 1. The 3D molecule was designed as a nonlinear dimer, 2,5-bis(8-(17-phenyl)-7,9,16,18-tetraazabenzodifluoranthene-3,4,12,13-tetracarboxylic acid diimide)thiophene (DBFI-T, FIG. 1B), synthesized from the BFI-Br2 building block, as described, for example, in EXAMPLE 4. The molecular structures of BFI-P2 and DBFI-T were confirmed by high resolution mass spectroscopy, elemental analysis, and NMR spectroscopy. Both BFI-P2 and DBFI-T have excellent solubility in organic solvents (chloroform, toluene, chlorobenzene, etc.) and are thus suitable for spin coating, printing and other solution processing methods. Thermogravimetric analysis showed that both molecules were thermally stable up to 410° C. while differential scanning calorimetry scans from 20 to 300° C. did not reveal any glass or melting transitions, indicating robust thermal stability desirable for OPV applications.

The molecular ordering of the new acceptors, BFI-P2 and DBFI-T were evaluated by X-ray diffraction (XRD) from solution-cast films. BFI-P2 exhibits an intense and two weak edge-to-edge Bragg diffractions at 3.1°, 5.6° and 7.3°, which correspond to d-spacings of 28.5 Å, 15.8 Å and 12.1 Å, respectively. Two high-order diffractions were also detected at 9.6° (d=28.5 Å) and 11.5° (d=12.1 Å) suggesting a high degree of crystallinity of BFI-P2 in film. On the contrary, DBFI-T only has one set of edge-to-edge diffraction peaks at 4.4° and 8.6° (d=20.1 Å), which is about 20 times weaker in intensity than that of BFI-P2 at 3.1°, indicating a poor crystalline property of DBFI-T molecules in the film. Both BFI-P2 and DBFI-T have two weak broad diffraction at around 20.0 (4.5 Å) and 24.0° (3.8 Å) arisen from weak π-π stackings of their molecules. The difference in crystallinity between BFI-P2 and DBFI-T is arisen from the fact that DBFI-T has two large BFI units twisted relative to each other while the BFI-P2 molecule has a relatively more planar structure.

Figure 1B:
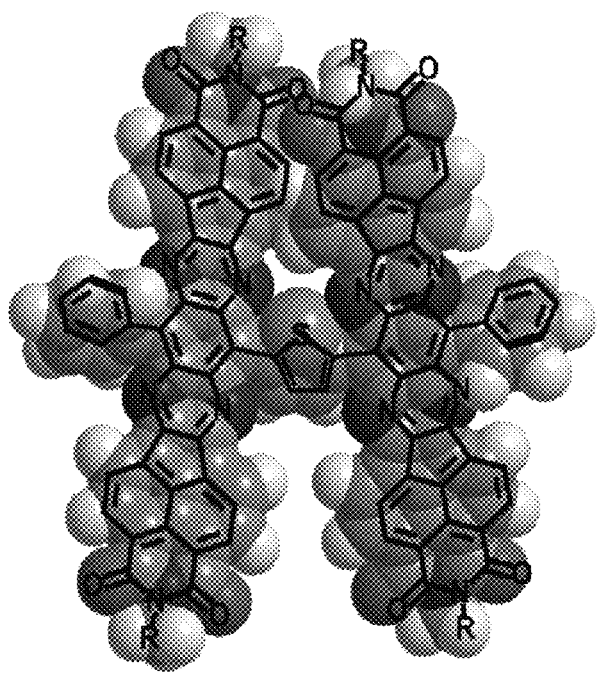
FIG. 1B is a representation of a space filling molecular model of an embodiment of a non-fullerene electron acceptor of the present disclosure.
Figure 1C:
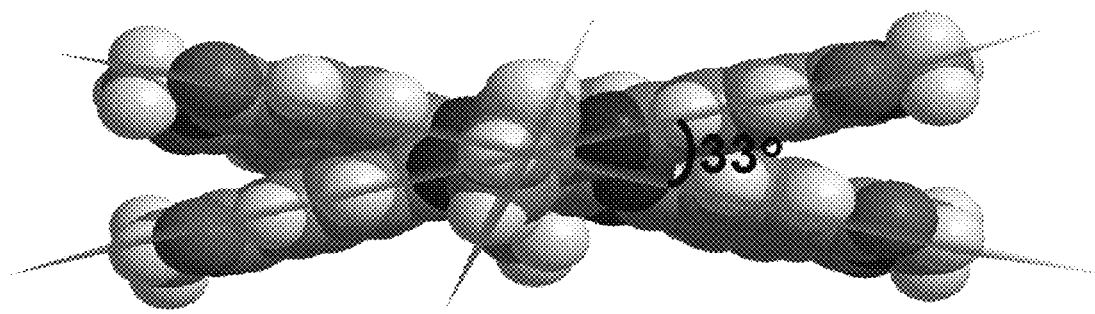
FIG. 1C is a side view of the space filling molecular model shown in FIG. 1B.

The geometry optimized molecular structures of BFI-P2 and DBFI-T using density functional theory (DFT) at the B3LYP/(6-31G(d,p) level are shown in FIGS. 1A-1C. The polycyclic 11-ring ladder-type BFI chromophore in BFI-P2 is perfectly planar and the calculated end-to-end distance between the imide nitrogen atoms of BFI-P2 is 19.7. In the case of DBFI-T, the molecule has the same 19.7 Å long planar BFI units and an end-to-end width of 19.5 Å at the middle (distance between para carbon atoms of each phenyl). The two BFI units in DBFI-T are strongly twisted with interplanar angle of 32.7° (FIG. 1C), resulting in an overall 3D structure. The π-conjugated DBFI-T molecule is significantly larger than either $PC_{60}BM$ or $PC_{70}BM$ (~7.1 Å in diameter for $C_{60}$[25] and ~7.0-8.2 Å in diameter for $C_{70}$[26]) (SI, FIG. S3).

Figure 1D:
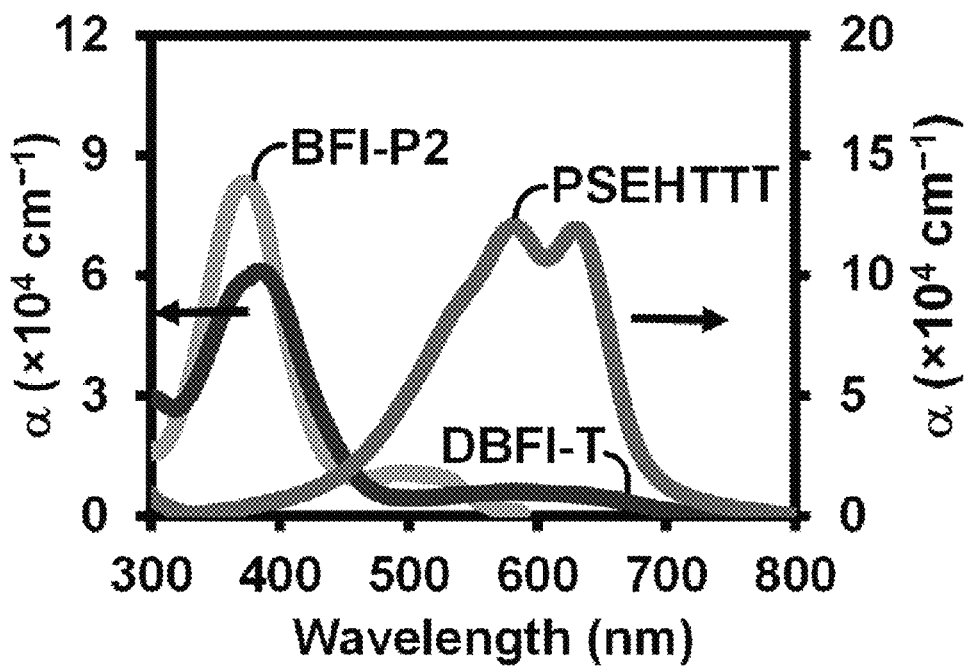
FIG. 1D is a graph showing thin film optical absorption spectra of embodiments of non-fullerene electron acceptors of the present disclosure and thin film optical absorption spectrum of a representative polymeric electron donor.
Figure 1E:
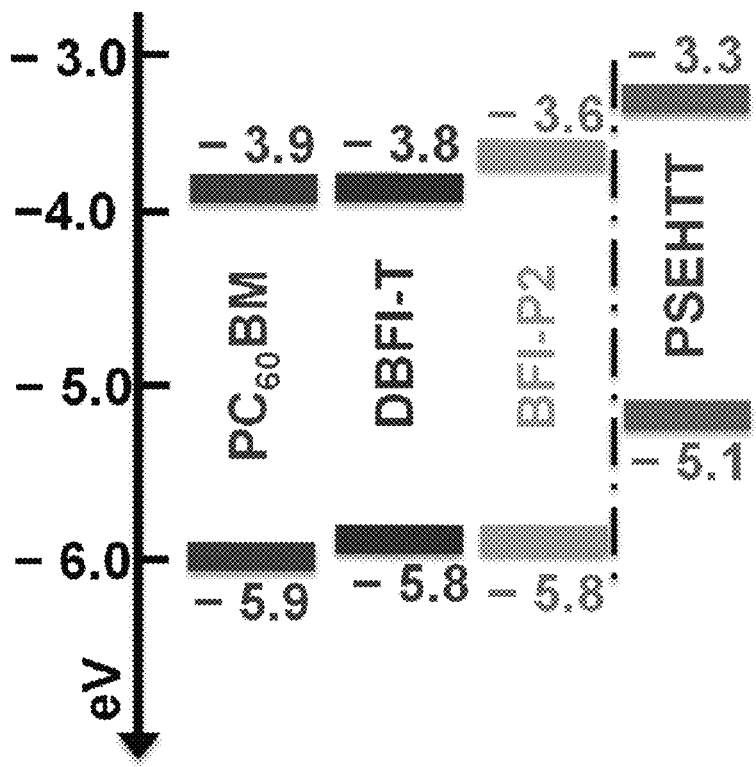
FIG. 1E is a graph showing energy levels of embodiments of non-fullerene electron acceptors of the present disclosure, a representative polymeric electron donor, and a representative fullerene-based electron acceptor.

Optical absorption and electronic structure of spin coated thin film of BFI-P2 and DBFI-T were characterized by optical absorption spectroscopy and cyclic voltammetry (FIGS. 1D-1E). The thin film absorption spectrum of BFI-P2 comprised of an intense UV band centered at 373 nm with an absorption coefficient of $8.1 \times 10^4$ $cm^{-1}$ and a weak, broad, visible band centered at ~500 nm ($\alpha$=$1.2 \times 10^4$ $cm^{-1}$). The former absorption band arises from the π-π* transition of the BFI chromophore. In contrast, the film absorption spectrum of the multichromophoric DBFI-T has a slightly red-shifted intense UV band ($\lambda_{max}$=384 nm, $\alpha$=$6.1 \times 10^4$ $cm^{-1}$) and a very broad visible band centered near 600 nm ($\alpha$=$7.1 \times 10^3$ $cm^{-1}$). The visible absorption band of DBFI-T is due to intramolecular charge transfer between the central thiophene ring and the BFI units. The absorption spectrum of the donor polymer PSEHTT (FIG. 1D) shows a broad visible band with a maximum at 584 nm and a high absorption coefficient ($1.1 \times 10^5$ $cm^{-1}$), indicating a promising donor component that could be paired the new non-fullerene acceptors in BHJ solar cells.

Figure 2A:
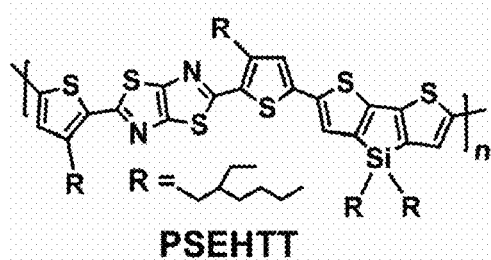
FIG. 2A is an illustration of a chemical structure of a representative polymeric electron donor.

The frontier molecular orbital energy levels, lowest unoccupied molecular orbital/highest occupied molecular orbital (LUMO/HOMO) energy levels of BFI-P2 and DBFI-T were estimated from cyclic voltammetry and are shown in FIG. 1E. The measured HOMO/LUMO energy levels for the donor polymer PSEHTT (structure shown in FIG. 2A) and fullerenes ($PC_{60}BM$ and $PC_{70}BM$) are also shown in FIG. 1E. These data indicate that there is sufficient driving energy for charge photogeneration in BHJ devices composed of PSEHTT and each of the non-fullerene electron acceptors as well as with the fullerene acceptors. The slightly higher lying LUMO energies of BFI-P2 and DBFI-T suggest a likely improvement in the open circuit voltage ($V_{oc}$) of non-fullerene acceptor/PSEHTT devices compared to PSEHTT/fullerene ones.

Top-contact, bottom-gate organic field-effect transistors (OFETs) based on solution deposited films using Si/SiO$_2$ as substrates/dielectrics and highly doped Si as gate, silver as source and drain contacts were fabricated to evaluate the electron mobilities of these acceptors. The output and transfer curves showed that both BFI-P2 and DBFI-T exhibited unipolar electron transport. BFI-P2 exhibited a maximal electron mobility ($\mu_{e, max}$) of up to 0.5 cm$^2$V$^{-1}$s$^{-1}$ ($\mu_{e, ave}$=0.2 cm$^2$V$^{-1}$s$^{-1}$) with $I_{on/off}$ of 10$^6$, while DBFI-T exhibited low electron mobility of $\mu_{e, max}$=0.006 cm$^2$V$^{-1}$s$^{-1}$ ($\mu_{e, ave}$=0.004 cm$^2$V$^{-1}$s$^{-1}$) with $I_{on/off}$ of 10$^2$. The low electron mobility of DBFI-T can be attributed to the poorer crystalline tendency of DBFI-T molecules in thin films.

Figure 2B:
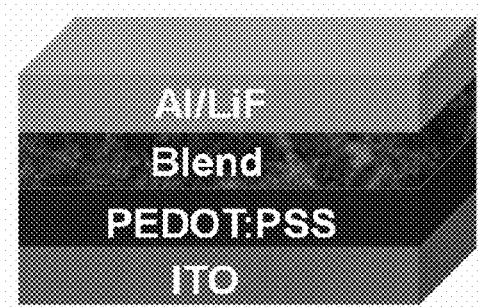
FIG. 2B is a schematic representation of a solar cell.
Figure 2C:
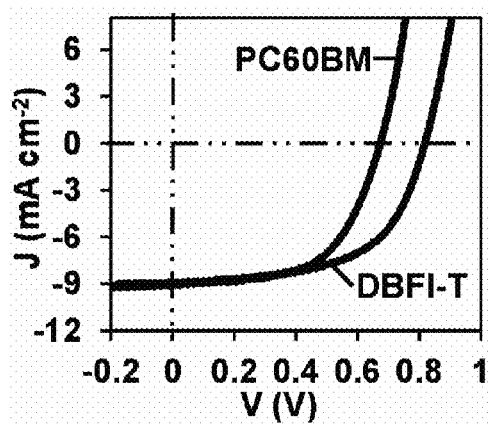
FIG. 2C is a graph comparing the current density-voltage (J-V) curves of a solar cell including a polymeric electron donor and an embodiment of a non-fullerene electron acceptor of the present disclosure, and a solar cell including a polymeric electron donor and a fullerene-based electron acceptor.
Figure 2D:
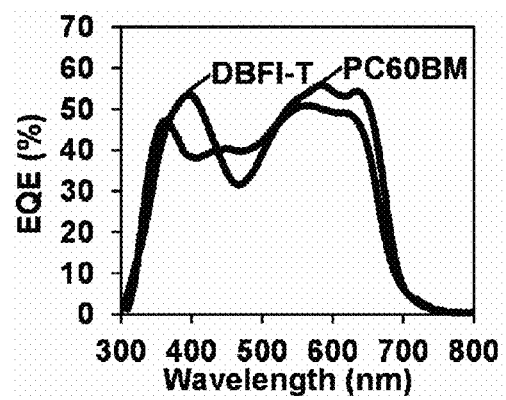
FIG. 2D is a graph comparing the external quantum efficiency (EQE) spectra of a solar cell including a polymeric electron donor and an embodiment of a non-fullerene electron acceptor of the present disclosure, and a solar cell including a polymeric electron donor and a fullerene-based electron acceptor.

BHJ solar cells with a conventional structure of indium tin oxide (ITO)/poly(3,4-ethylenedioxythiophene):poly(styrenesulfonate) (PEDOT:PSS)/PSEHTT: DBFI-T/LiF/Al (FIG. 2B) were fabricated and the current density (J)-voltage (V) characteristics were evaluated under AM1.5 solar illumination at 1 sun (100 mWcm$^{-2}$). Optimization of the blend active layer composition showed that 1:2 wt/wt PSEHTT: DBFI-T photodiodes gave the best PCE of 4.24%, $V_{oc}$ of 0.82 V, short circuit current ($J_{sc}$) of 9.02 mAcm$^{-2}$ and a fill factor (FF) of 57% (FIG. 2C, Table 1). The external quantum efficiency (EQE) spectrum of the PSEHTT:DBFI-T photodiode (FIG. 2D) shows that the photocurrent turns on at about 720 nm and has peaks of 53% at 380-420 nm and 51% at 540-620 nm due respectively to the DBFI-T and PSEHTT components. The $J_{sc}$ calculated from the EQE spectrum is 8.30 mAcm$^{-2}$, which is 8.7% lower than from the direct J-V measurement. Similarly fabricated and tested PSEEHTT: BFI-P2 blend (1:4 wt/wt) photodiodes gave the best performance with PCE=1.03%, $J_{sc}$=2.31 mAcm$^{-2}$, $V_{oc}$=0.9 V, and FF=49%. Although the $V_{oc}$ of BFI-P2 solar cells is higher than those of DBFI-T, as expected from their LUMO energy levels (FIG. 1E), the photocurrent and PCE of BFI-P2 devices are about a factor of 4 lower. These results show that the 3D multichromophoric acceptor DBFI-T has superior electron accepting properties in OPV cells than those of the 1D molecule BFI-P2.

TABLE 1

Photovoltaic properties of PSEHTT:acceptor BHJ solar cells.

| Device | Acceptor[a] | $J_{sc}$ (mA/cm$^2$) | $V_{oc}$ (V) | FF (%) | PCE (%) | PCE$_{max}$ (%) |
|---|---|---|---|---|---|---|
| Conventional cell | DBFI-T[b] | 9.02 | 0.82 | 57 | 4.19-Ttio | 4.24 |
|  | BFI-P2[c] | 2.31 | 0.90 | 49 | 0.99P2tio | 1.03 |
|  | PC$_{60}$BM | 9.07 | 0.68 | 58 | 3.49P2tio | 3.55 |
| Inverted cell | DBFI-T[d] | 10.14 | 0.86 | 58 | 4.914Ted | 5.04 |
|  | BFI-P2[e] | 3.16 | 0.94 | 49 | 1.39P2ed | 1.44 |
|  | PC$_{60}$BM | 8.46 | 0.64 | 62 | 3.23P2ed | 3.34 |

[a]All active layers were deposited from chloroform solutions.
[b]PSEHTT:DBFI-T at 1:2 (wt/wt), annealing at 175° C. for 10 min.
[c]PSEHTT:BFI-P2 at 1:4 (wt/wt), annealing at 175° C. for 10 min.
[d]PSEHTT:DBFI-T at 1:2 (wt/wt), annealed at 175° C. for 10 min.
[e]PSEHTT:BFI-P2 at 1:4 (wt/wt), annealed at 150° C. for 10 min.

Figure 2E:
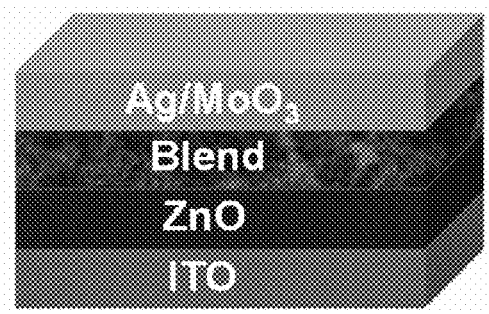
FIG. 2E is a schematic representation of an inverted solar cell.
Figure 2F:
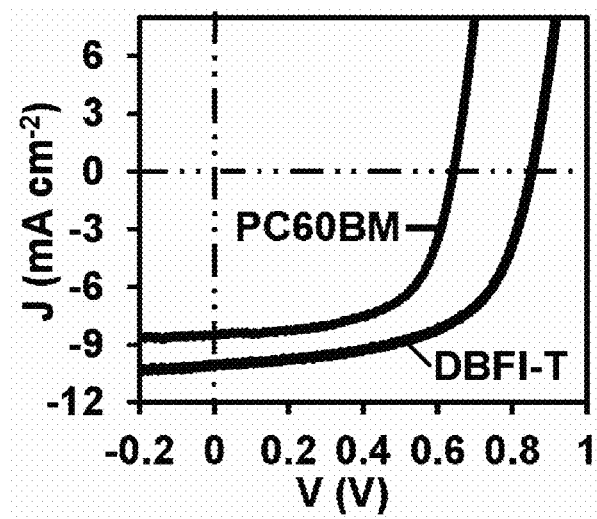
FIG. 2F is a graph comparing the J-V curves of an inverted solar cell including a polymeric electron donor and an embodiment of a non-fullerene electron acceptor of the present disclosure, and an inverted solar cell including a polymeric electron donor and a fullerene-based electron acceptor.
Figure 2G:
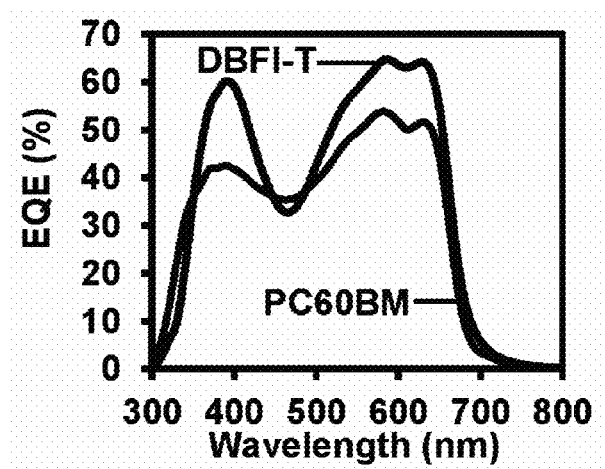
FIG. 2G is a graph comparing the EQE spectra of an inverted solar cell including a polymeric electron donor and an embodiment of a non-fullerene electron acceptor of the present disclosure, and an inverted solar cell including a polymeric electron donor and a fullerene-based electron acceptor.
Figure 3A:
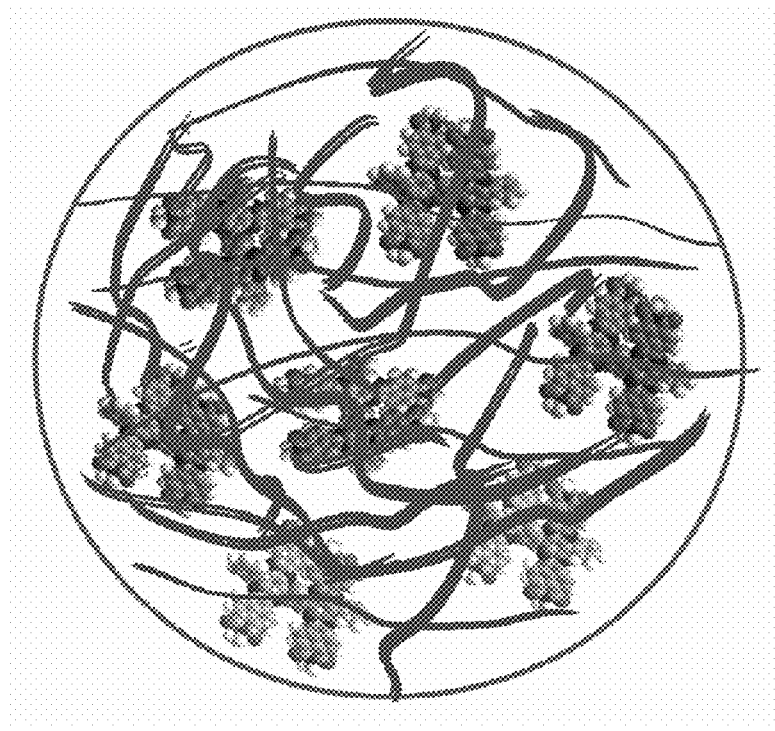
FIG. 3A is a schematic representation of a blend of a representative polymeric electron donor and an embodiment of a non-fullerene electron acceptor of the present disclosure.
Figure 3B:
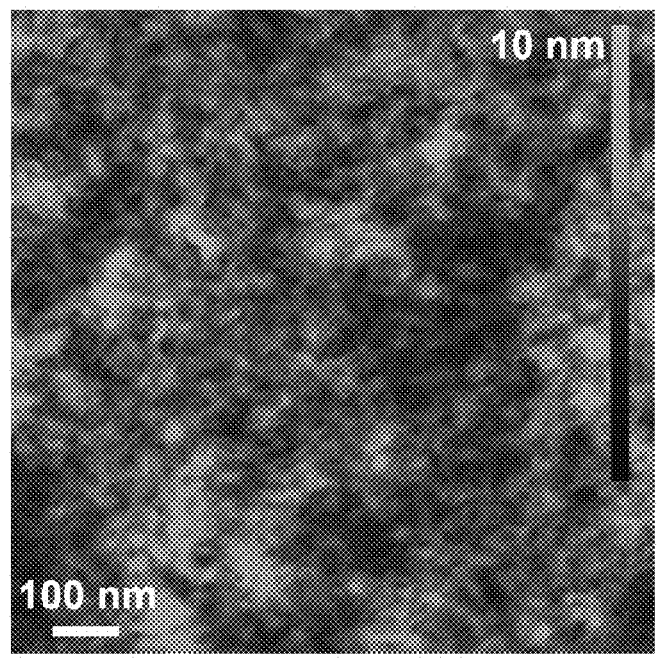
FIGS. 3B and 3C are AFM topographic micrographs of the blend of a representative polymeric electron donor and an embodiment of a non-fullerene electron acceptor of FIG. 3A.
Figure 3C:
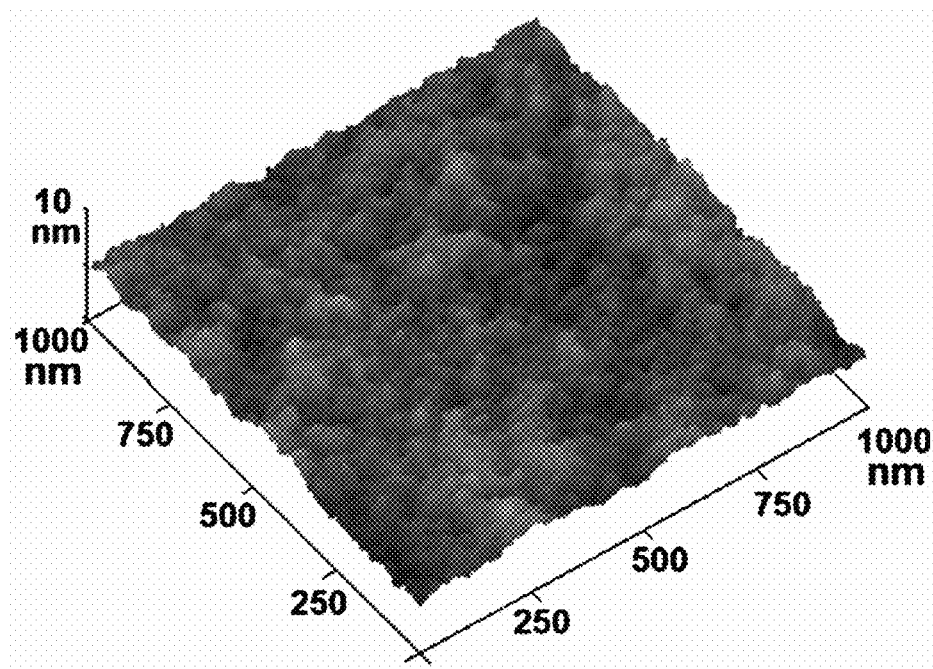
Figure 3D:
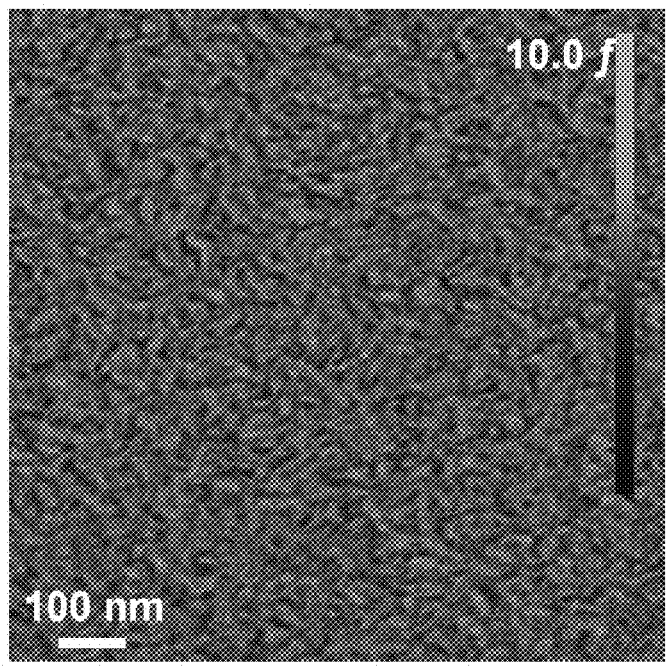
FIG. 3D is an AFM phase micrograph of the blend of a representative polymeric electron donor and an embodiment of a non-fullerene electron acceptor of FIG. 3A.

Inverted solar cells with the structure ITO/zinc oxide (ZnO)/PSEHTT:DBFI-T/molybdenum oxide/(MoO$_3$)/Ag (FIG. 2E) were also fabricated and evaluated to further investigate the photovoltaic properties of the new electron acceptors. In this case, the optimum PSEHTT:DBFI-T (1:2, wt/wt) photodiodes gave a higher PCE of 5.04% with $V_{oc}$=0.86 V, $J_{sc}$=10.14 mAcm$^{-2}$, and FF=58% (FIG. 2F, Table 1). The corresponding EQE spectrum of the optimum photodiodes showed a peak value of 65% in the 550-620 nm range and 60% in the 380-420 nm range (FIG. 2G). The $J_{sc}$ value of 9.82 mAcm$^{-2}$ calculated from the EQE spectrum is within 3% of the value measured directly from the J-V curve. The optimum inverted PSEHTT:BFI-P2 blend (1:4 wt/wt) cells had a PCE of 1.44% with $J_{sc}$=3.16 mAcm$^{-2}$, $V_{oc}$=0.94 V and FF=49%, which is about a factor of 3 less compared to the performance of DBFI-T. These results further confirm the excellent electron-accepting and photovoltaic properties of DBFI-T.

Both conventional and inverted PSEHTT:PC$_{60}$BM and PSEHTT:PC$_{70}$BM BHJ solar cells were fabricated for comparison with the above results for the new non-fullerene electron acceptors. The PSEHTT:PC$_{60}$BM (1:2 wt/wt) blend active layers were fabricated under optimized conditions that include the use of a 1,8-diiodooctane (DIO) processing additive, as described in Subramaniyan, S. et al. *Adv. Energy Mater.* 1,854-860 (2011); Xin, H. et al. *Chem. Mater.* 24, 1995-2001 (2012), each of which is herein incorporated by reference in its entirety. The results (Table 1) show that both conventional and inverted PSEHTT:PC$_{60}$BM photodiodes with maximum PCEs of 3.34-3.55% are substantially inferior to those of PSEHTT:DBFI-T with efficiencies of 4.24-4.46%. The photovoltage produced by the non-fullerene electron acceptors is significantly larger than that of the fullerene-based devices, as expected from the energy level offsets of the materials (FIG. 1E). The efficiency of PC$_{70}$BM cells (Table 1) is higher than those of DBFI-T devices primarily by virtue of the large photocurrents facilitated by processing additive enabled optimum nanoscale morphology. Overall, based on the donor polymer PSEHTT, the electron-accepting and photovoltaic properties of the new acceptor DBFI-T are comparable to those of the fullerenes.

The electron accepting abilities of DBFI-T and its one-unit model BFI-P2 were evaluated based on degenerated LUMO energy levels and low lying excited states of the neutral molecules and the anion states. Dimer DBFI-T has six quasi degenerated LUMOs with close energy levels of −3.35 eV to −3.04 eV and its anion radical has five low lying excited states (<0.50 eV), whereas BFI-P2 only has three degenerated LUMOs ranging from −3.27 eV to −2.99 eV and its anion radical has two low-energy excited states (<0.6 eV). Thus, DBFI-T can be expected to have better electron accepting ability than BFI-P2 in photovoltaic cells.

The solid morphologies of the PSEHTT:BFI-P2 (1:4 wt/wt) and PSEHTT:DBFI-T (1:2 wt/wt) blends were investigated by XRD. For comparison, the XRD of the donor polymer PSEHTT was also measured showing a weak diffract indexed to (100) at 5.0° (d=17.8 Å) and a broad weak diffraction at 24.5° (d=3.7 Å) due to a lamellar packing and a π-π stacking of PSEHTT polymer, respectively. The blends of PSEHTT:BFI-P2 and PSEHTT:DBFI-T maintain the diffraction patterns of the neat films of the respective acceptor and PSEHTT, i.e., the diffraction patterns from the neat films of the acceptors and PSEHTT were also shown in the blend film. These results suggested that there is certain degree of phase separation in the PSEHTT:BFI-P2 and PSEHTT:DBFI-T blend films which is desirable for charge separation and charge transport.

The morphologies of the active layers of the inverted PSEHTT:BFI-P2 and PSEHTT:DBFI-T devices were also examined by atomic force microscopy (AFM) and transmission electron microscopy (TEM). AFM topography image shows that PSEHTT:DBFI-T blend film has a smooth surface with a maximal roughness ($R_{max}$) of 6.36 nm (FIG. 3). The corresponding phase image showed a uniform nanophase separation with interconnected networks, which is highly desired for efficient charge separation and charge transport and is consistent with the high PCE achieved in the DBFI-T-based solar cells. TEM image of the active layer of the same device did not show any apparent features or phase separation. In contrast, PSEHTT:BFI-P2 formed a rougher surface with $R_{max}$=10.6 nm in the topography image of the blend film. Large gains over 100 nm were observed in the corresponding phase image. In the TEM image, large phases of a few tens nm to of 200-300 nm were observed. The rough surface and large phase separation in the PSEHTT:BFI-P2 active layers arisen from the high crystallinity of BFI-P2 can be among the reasons for the poor photovoltaic performance of the corresponding devices.

Photoconductivity experiments were also conducted and the results are described below as an independent means of probing the intrinsic charge photogeneration and photoelectronic properties of the new acceptor molecules relative to the PCBM benchmark. The photoconductive properties of PSEHTT:BFI-P2 and PSEHTT:DBFI-T blends were investigated by means of Xe-flash time-resolved microwave conductivity (TRMC) technique, where a 10 μs-width white light pulse (pseudo solar spectrum) from a Xe-flash lamp and 9 GHz microwave were used as an excitation and a probe, respectively. FIG. 4A shows the dependences of transient photoconductivity maxima ($\Delta\sigma_{max}$) on the blend ratio of PSEHTT:BFI-P2 and PSEHTT:DBFI-T. The $\Delta\sigma_{max}$ of Xe-flash TRMC evaluates the overall optoelectronic performance of the film without fabricating devices, as it includes information about the charge separation yield, local charge carrier mobility, their lifetimes, and sunlight absorption property of the films. PSEHTT:BFI-P2 and PSEHTT:DBFI-T show peaks (best blend ratio) at around donor:acceptor (p:n)=1:3 and 1:2, respectively. The laser-flash TRMC of these films indicate that the peak position varies with different excitation wavelength (355, 500, and 680 nm), as a result of interplay of charge carrier generation pathway from excitons in p phase (donor) and n phase (acceptor). The $\Delta\sigma_{max}$ of laser- and Xe-flash TRMC are, nonetheless, always higher for PSEHTT:DBFI-T than PSEHTT:BFI-P2, indicative of better photovoltaic device performance of DBFI-T. At 500 nm excitation, a seven-fold increase of $\Delta\sigma_{max}$ was observed for PSEHTT:BFI-P2 by blending BFI-P2 with PSEHTT, while PSEHTT:DBFI-T displays as much as 38-fold increase in $\Delta\sigma_{max}$. These results demonstrate a potential high photovoltaic efficiency of BHJ blends of PSEHTT and DBFI-T.

Thus, a new class of organic electron acceptors that rivals fullerenes in OPV cells has been synthesized and characterized. As an acceptor in conventional and inverted OPV cells, the 3D DBFI-T is superior to $PC_{60}BM$ and is comparable to $PC_{70}BM$. The observed high photocurrent, filled factor, and EQE imply efficient charge photogeneration in DBFI-T/polymer blends. However, the large size and largely amorphous nature of DBFI-T suggest that the detailed mechanism of charge photogeneration in DBFI-T/polymer blends is very different from that of polymer/fullerene systems. The 3D multichromophore approach to the new acceptors could be useful in the design of more efficient OPV materials.

Fabrication and Testing of Conventional Solar Cells

Solar cells with device structure of ITO/PEDOT:PSS/active layer/LiF/Al were fabricated. ITO substrates (10Ω/□, Shanghai B. Tree Tech. Consult Co., Ltd, Shanghai, China) were cleaned sequentially with acetone, deionized water and isopropyl alcohol in an ultrasonic bath, and blown with nitrogen until dried. A 40 nm PEDOT:PSS (Clevios P VP AI 4083) layer was spin-coated on top of the ITO and dried at 150° C. for 10 min under vacuum. The PSEHTT:BFI-P2 active layer was then spin-coated from PSEHTT:BFI-P2 (1:4 wt/wt) mixture solution in chloroform to make a thin film of ~120 nm thickness and thermally annealed at 150° C. for 10 min in a glovebox. The PSEHTT:DBFI-T active layer was spin-coated from PSEHTT:DBFI-T (1:2, wt/wt) mixture solution in chloroform to make a thin film of ~100 nm thickness and thermally annealed at 175° C. for 10 min in a glovebox. The substrates were then loaded in a thermal evaporator (BOC Edwards, 306) to deposit a cathode composed of 1.0 nm LiF and 90 nm Al under high vacuum (8×10-7 Torr). Five solar cells, each with an active area of 4 mm2, were fabricated per ITO substrate. The current density-voltage (J-V) curves of solar cells were measured using a HP4155A semiconductor parameter analyzer under laboratory ambient air conditions. An AM1.5 illumination at 100 mW/cm$^2$ was provided by a filtered Xe lamp and calibrated by using an NREL-calibrated Si diode. The external quantum efficiency (EQE) was measured using a QEX10 solar cell quantum efficiency measurement system (PV Measurements, Inc.) and was calibrated with a NREL-certified Si diode before measurement.

Fabrication and Testing of Inverted Solar Cells

Solar cells with the inverted device structure of ITO/ZnO/active layer/$MoO_3$/Ag were fabricated. ITO substrates were cleaned as the same procedure mentioned above, followed by oxygen plasma treatment. Zinc oxide (ZnO) precursor was prepared as reported in Sun, Y. et al., *Adv. Mater.* 23, 1679-1683 (2011), herein incorporated by reference in its entirety, spin-coated on top of the ITO and annealed at 250° C. for 1 hr in air. The ZnO film thickness was approximately 30 nm which is measured by the profilometer. ZnO surface modification was conducted by spin-coating a solution of ethanolamine in 2-methoxyethanol (1 vol %) followed by drying at 110° C. for 10 min. The PSEHTT:BFI-P2 (~60 nm) and PSEHTT:DBFI-T (~60 nm) active layers were spin-coated from the PSEHTT:BFI-P2 (1:4 wt/wt) and PSEHTT:DBFI-T (1:2 wt/wt) mixture solutions in chloroform, respectively, and thermally annealed at 150° C. for 10 min in a glovebox. The substrates were then loaded in a thermal evaporator (BOC Edwards, 306) to deposit an anode composed of thin layer of 10.0 nm $MoO_3$ and 100 nm Ag under high vacuum (8×10$^{-7}$ Torr). Five solar cells, each with an active area of 4 mm$^2$, were fabricated per ITO substrate. The devices were characterized similarly as the conventional devices mentioned above.

Time-resolved Microwave Conductivity (TRMC)

Blend films of PSEHTT:BFI-P2 and PSEHTT:DBFI-T on quartz plates were prepared by drop-casting of chlorobenzene solutions without solvent additive at desired p:n compositions, and dried in a vacuum oven for 2 h at room temperature. A mixing ratio of PSEHTT:$PC_{60}BM$ film was fixed at optimal condition (p:n=1:2, chlorobenzene, 2.5 v/v % DIO) and films were prepared in the same fashion. A resonant cavity was used to obtain a high degree of sensitivity in the TRMC measurements. The resonant frequency and microwave power were set at ca. 9.1 GHz and 3 mW, respectively, so that the electric field of the microwave was sufficiently small to not disturb the motion of charge carriers. The third harmonic generation (THG; 355 nm) of a Nd:YAG laser (Continuum Inc., Surelite II, 5-8 ns pulse duration, 10 Hz) or 500 nm and 680 nm pulses from an optical parametric oscillator (Continuum Inc., Panther) seeded by THG of a Nd:YAG laser was used as an excitation source. The laser power was fixed at 2.5 mJ cm$^{-2}$ pulse$^{-1}$ for all excitation wavelengths (incident photon density, $I_0$=4.6, 6.4, and 8.7×10$^{15}$ photons cm$^{-2}$ pulse$^{-1}$ for 355, 500, and 680 nm, respectively). An in-house-built Xe-flash lamp (10

μs pulse duration, 10 Hz) with a power of 0.3 mJ cm$^{-2}$ pulse$^{-1}$ was used for the Xe-flash TRMC experiments. For the attenuation of excitation light energy, neutral density filters were used for both Xe-flash and laser-flash TRMC.

While illustrative embodiments have been illustrated and described, it will be appreciated that various changes can be made therein without departing from the spirit and scope of the invention.

What is claimed is:

1. A compound of Formula (I)

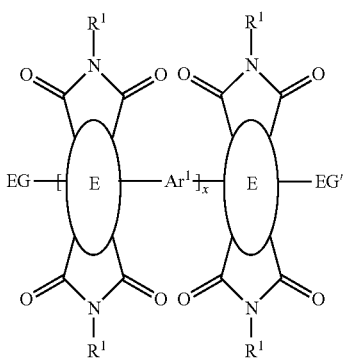

(I)

wherein:

EG and EG' are each independently $(W)_m$—W',
  wherein W is independently selected from arylene, heteroarylene, alkenylene, and alkynylene, each optionally substituted by 1, 2, 3, or 4 substituents independently selected from halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, CN, NO$_2$, and OH;
  W' is independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH; and
  m is 0, 1, or 2;

E is independently selected from

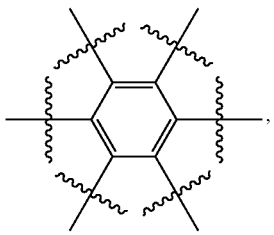

,

-continued

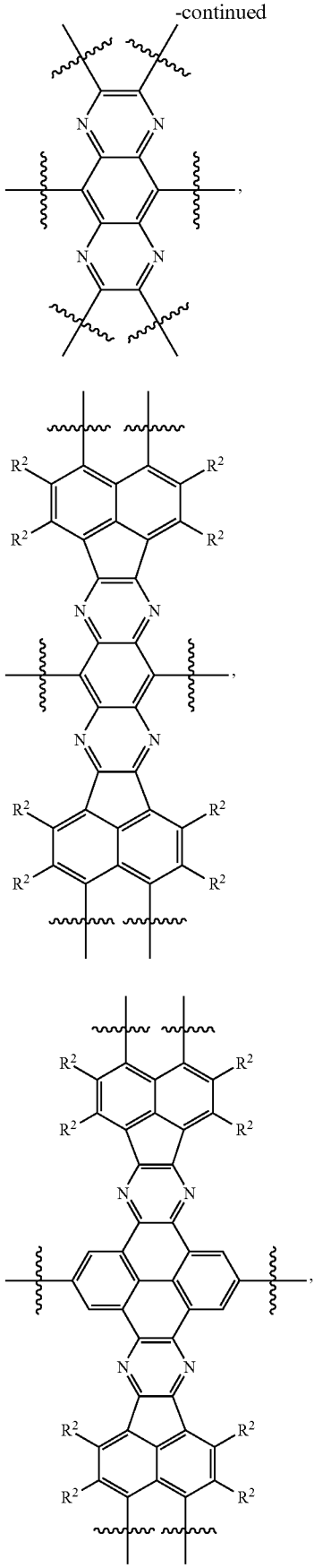

-continued

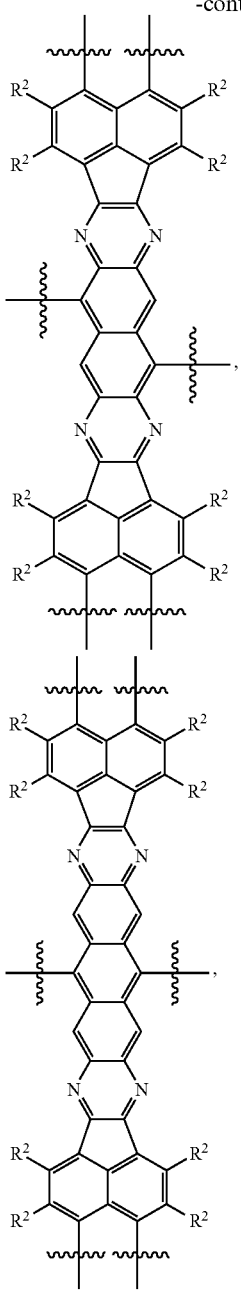

wherein R² is each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO₂, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, NO₂, and OH;

Ar¹ is a π-conjugated linker;

R¹ is each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO₂, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, NO₂, and OH;

x is 1 or 2.

2. The compound of claim 1, having a weight average molecular weight of less than 5,000.

3. The compound of claim 1, wherein E is

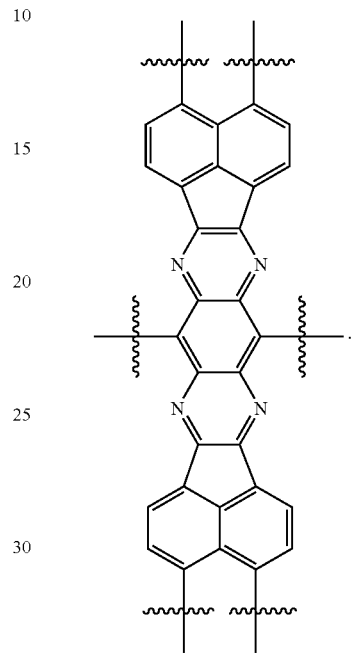

4. The compound of claim 1, wherein R¹ is alkyl optionally substituted with 1, 2, 3, 4, or 5 substituents independently selected from halo, $C_{1-50}$ alkyl, $C_{2-50}$ alkenyl, and $C_{2-50}$ alkynyl.

5. The compound of claim 1, wherein R¹ is

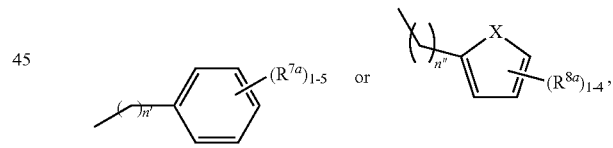

wherein $R^{7a}$ and $R^{8a}$ are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO₂, and OH, wherein said alkyl, alkenyl, alkynyl, alkoxy, aryl, heteroaryl, cycloalkyl, or heterocycloalkyl is optionally substituted with 1, 2, 3, 4, or 5 substituents independently selected from halo, $C_{1-50}$ alkyl, $C_{2-50}$ alkenyl, $C_{2-50}$ alkynyl, $C_{2-50}$ alkoxy, CN, NO₂, and OH, wherein n' and n" are each 0 to 50.

6. The compound of claim 1, wherein R¹ and R² are each independently selected from H, halo, alkyl, alkenyl, alkynyl, and alkoxy, wherein said alkyl, alkenyl, alkynyl, or alkoxy is optionally substituted with 1, 2, 3, 4, or 5 substituents independently selected from halo, $C_{1-50}$ alkyl, $C_{2-50}$ alkenyl, and $C_{2-50}$ alkynyl.

7. The compound of claim 1, wherein W is independently selected from:

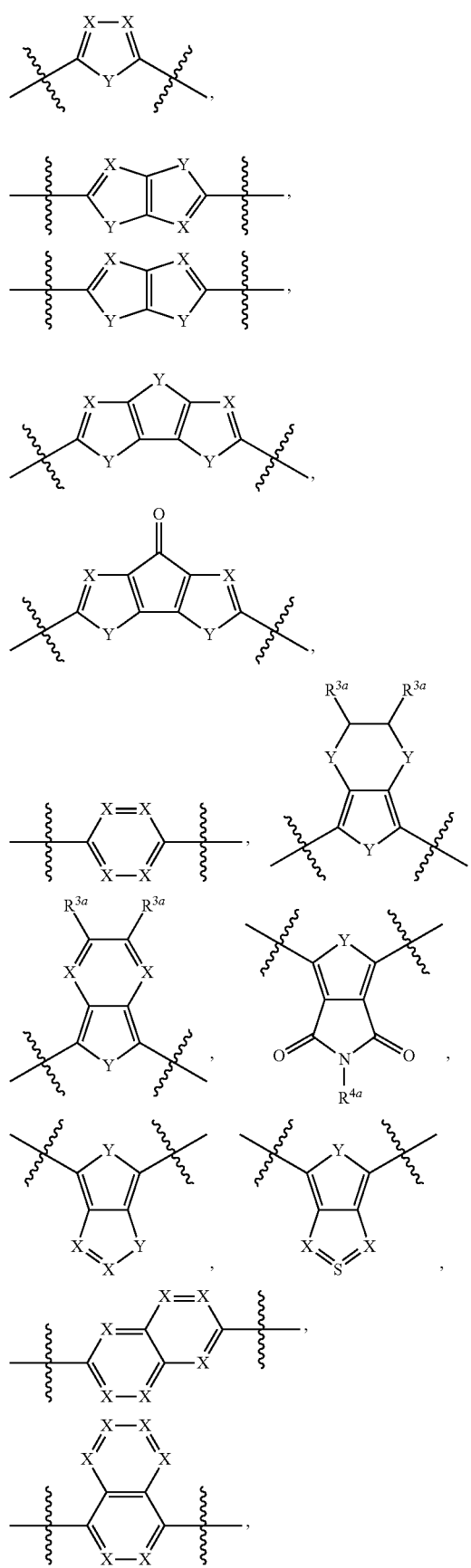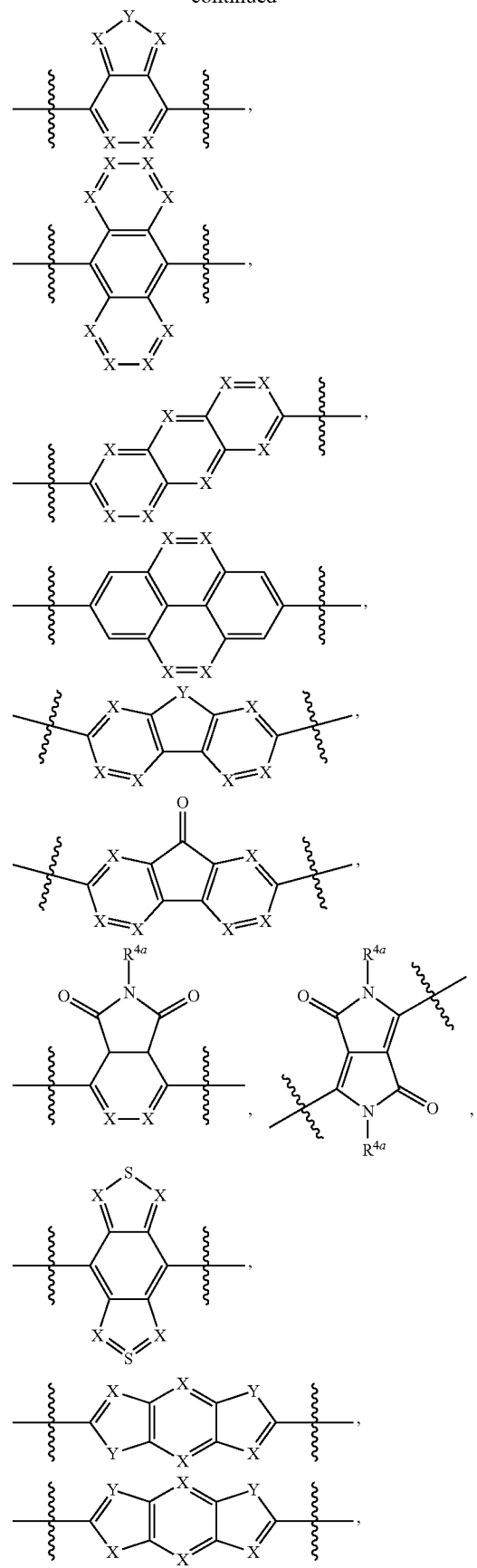

-continued

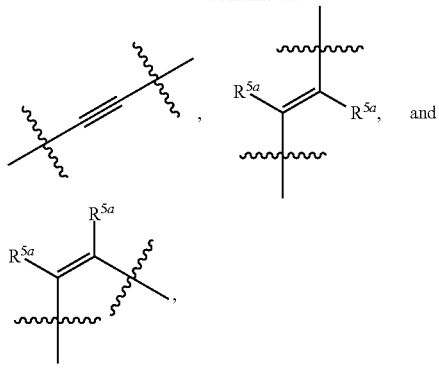

wherein Y is independently selected from O, S, SO$_2$, Se, Te, N(R$^{3a}$), C(R$^{3a}$)$_2$, Si(R$^{3a}$)$_2$, and Ge(R$^{3a}$)$_2$;

X is independently selected from CR$^{6a}$ and N; and

R$^{3a}$, R$^{4a}$, R$^{5a}$, and R$^{6a}$ are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

8. The compound of claim 7, wherein W' is independently selected from

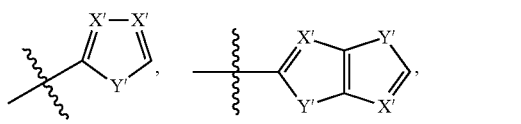

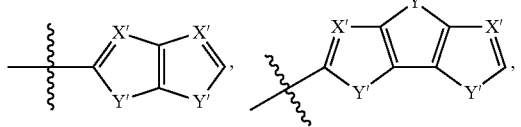

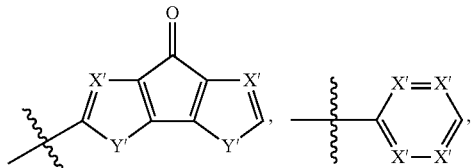

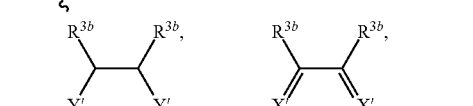

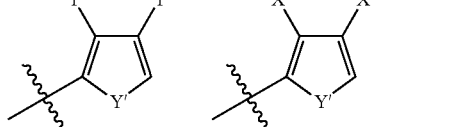

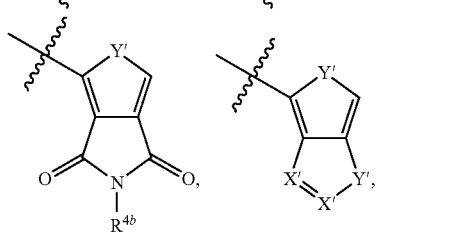

-continued

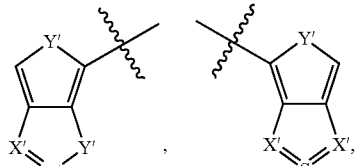

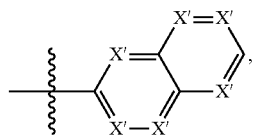

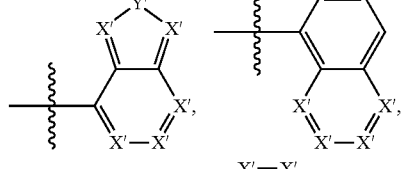

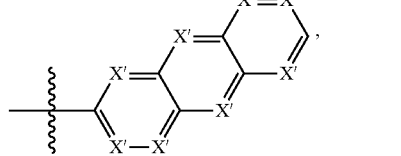

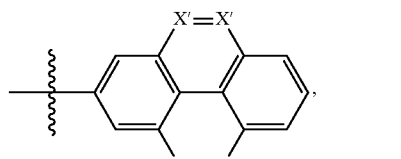

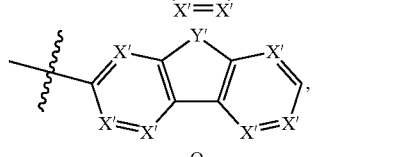

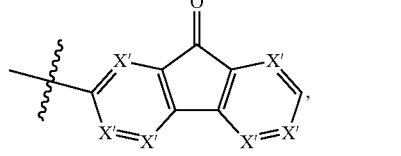

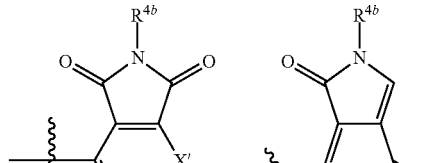

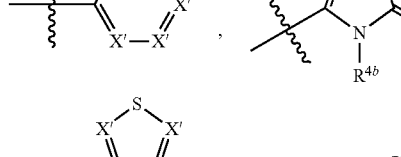

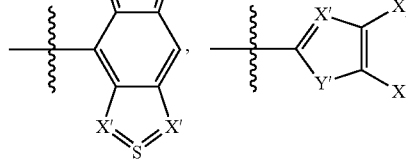

-continued

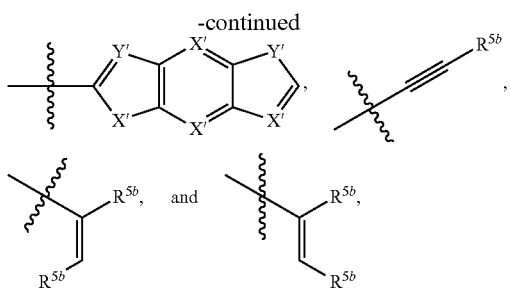

wherein Y' is independently selected from O, S, SO$_2$, Se, Te, N(R$^{3b}$), C(R$^{3b}$)$_2$, Si(R$^{3b}$)$_2$, and Ge(R$^{3b}$)$_2$;

X' is independently selected from CR$^{6b}$ and N; and

R$^{3b}$, R$^{4b}$, R$^{5b}$, and R$^{6b}$ are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO$_2$, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO$_2$, and OH.

9. The compound of claim 1, wherein EG and EG' are each independently selected from

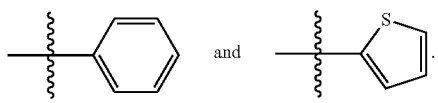

10. The compound of claim 1, provided that EG and EG' are not both H, or both halo, and provided that when one of EG and EG' is H, the other is not halo.

11. The compound of claim 8, wherein Ar$^1$ is independently selected from

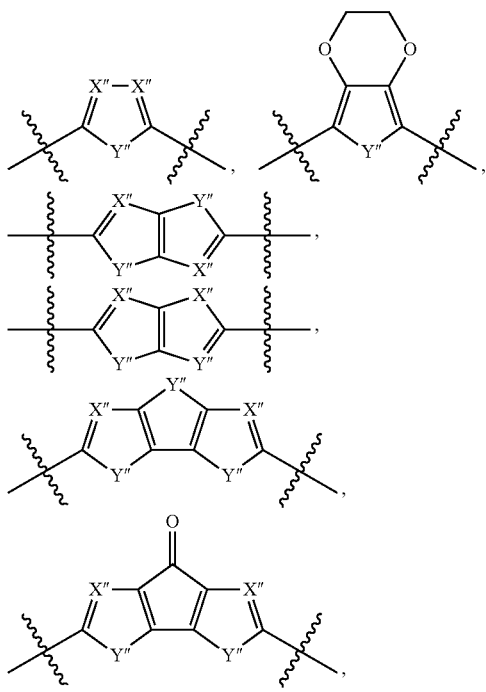

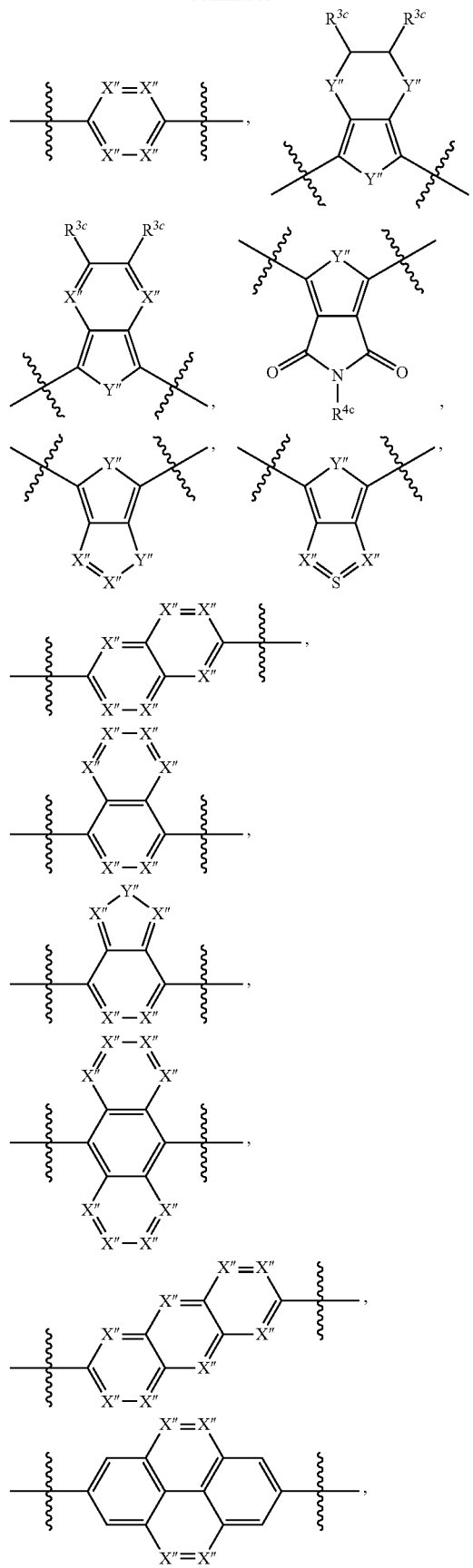

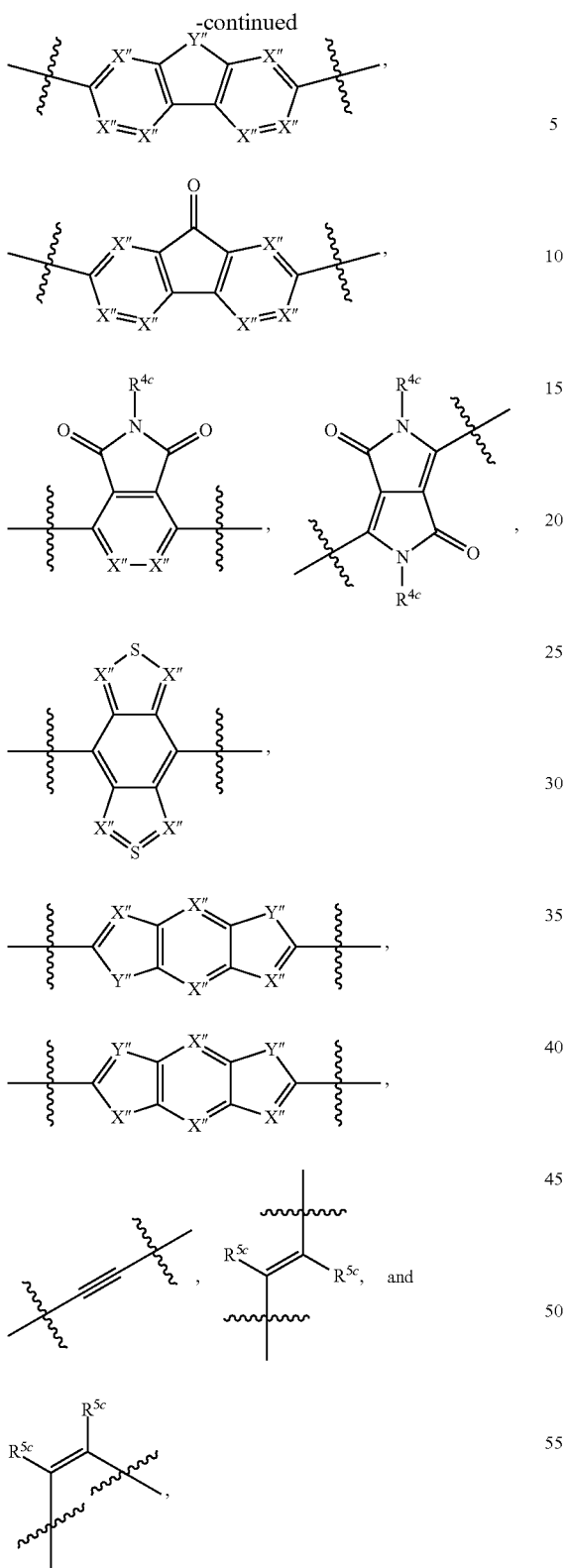

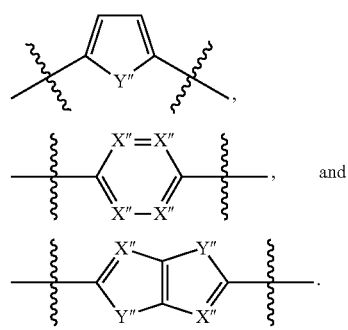

wherein Y" is independently selected from O, S, SO₂, Se, Te, N(R$^{3c}$), C(R$^{3c}$)₂, Si(R$^{3c}$)₂, and Ge(R$^{3c}$)₂;
X" is independently selected from CR$^{6c}$ and N; and
R$^{3c}$, R$^{4c}$, R$^{5c}$, and R$^{6c}$ are each independently selected from H, halo, alkyl, haloalkyl, alkenyl, haloalkenyl, alkynyl, haloalkynyl, alkoxy, haloalkoxy, aryl, heteroaryl, cycloalkyl, heterocycloalkyl, CN, NO₂, and OH, wherein said alkyl, alkenyl, alkynyl, alkoxy, aryl, heteroaryl, cycloalkyl, or heterocycloalkyl is optionally substituted with 1, 2, 3, or 4 substituents independently selected from halo, C$_{1-50}$ alkyl, C$_{2-50}$ alkenyl, C$_{2-50}$ alkynyl, C$_{2-50}$ alkoxy, CN, NO₂, and OH.

12. The compound of claim 11, wherein Ar$^1$ is selected from

13. The compound of claim 11, wherein R$^{3a}$, R$^{4a}$, R$^{5a}$, R$^{6a}$, R$^{3b}$, R$^{4b}$, R$^{5b}$, R$^{6b}$, R$^{3c}$, R$^{4c}$, R$^{5c}$, and R$^{6c}$, when present, are independently selected from H, halo, alkyl, alkenyl, alkynyl, and alkoxy, wherein said alkyl, alkenyl, alkynyl, or alkoxy is optionally substituted with 1, 2, 3, or 4 substituents independently selected from halo, C$_{1-50}$ alkyl, C$_{2-50}$ alkenyl, and C$_{2-50}$ alkynyl.

14. The compound of claim 11, wherein R$^{6a}$, R$^{6b}$, and R$^{6c}$, when present, are each independently selected from H, halo, CN, and NO₂.

15. The compound of claim 11, wherein R$^{6a}$, R$^{6b}$, and R$^{6c}$, when present, are each independently selected from H and alkyl.

16. The compound of claim 11, wherein R$^{6a}$, R$^{6b}$, and R$^{6c}$, when present, are each H.

17. The compound of claim 11 selected from

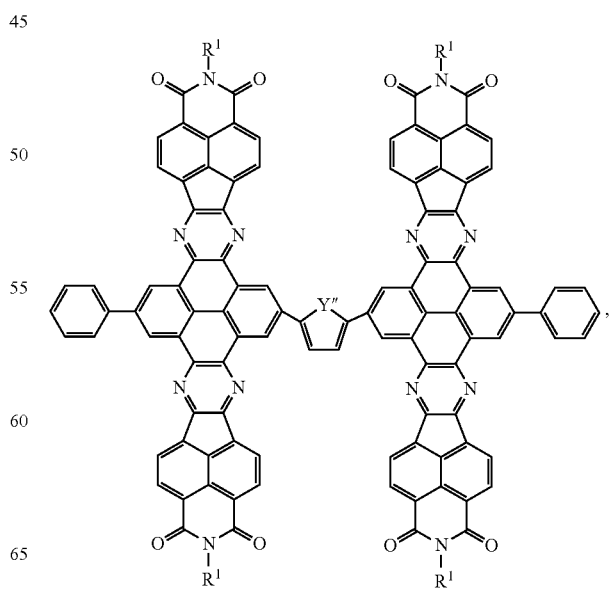

127
-continued
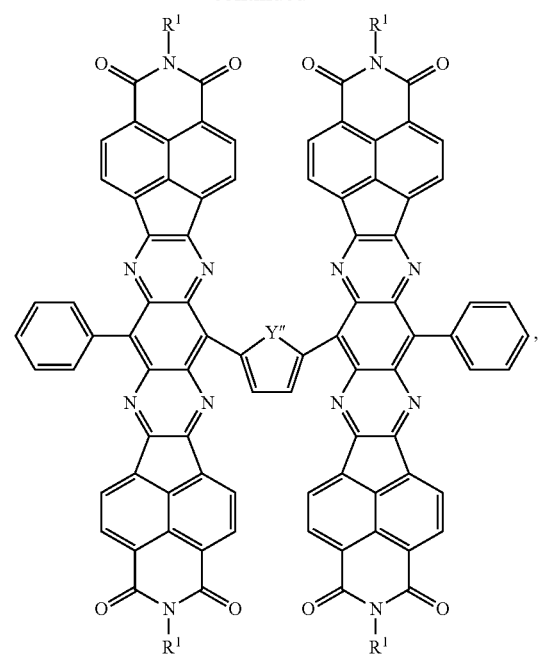
128
-continued
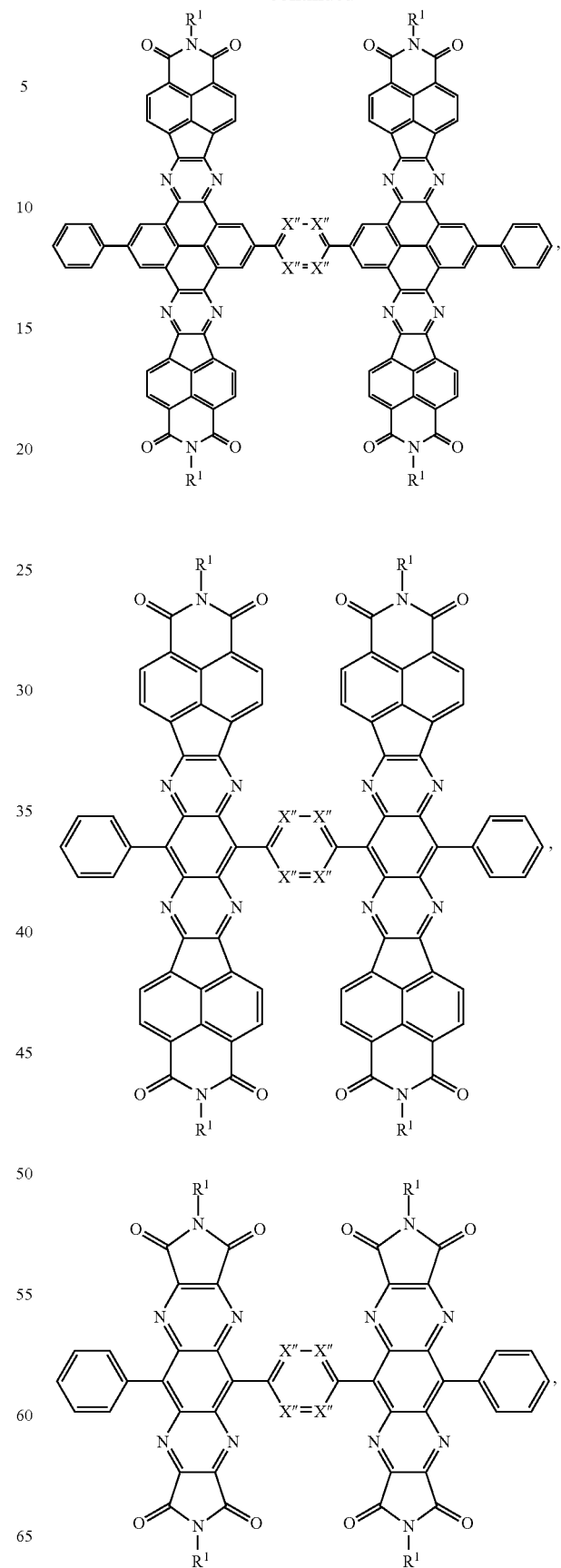

129
-continued
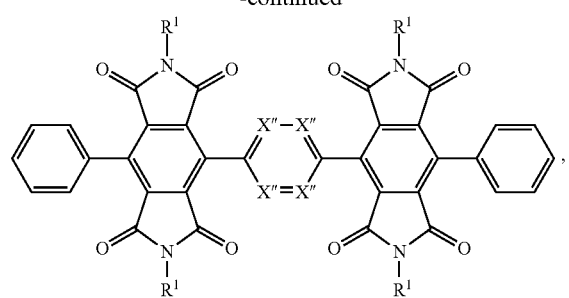
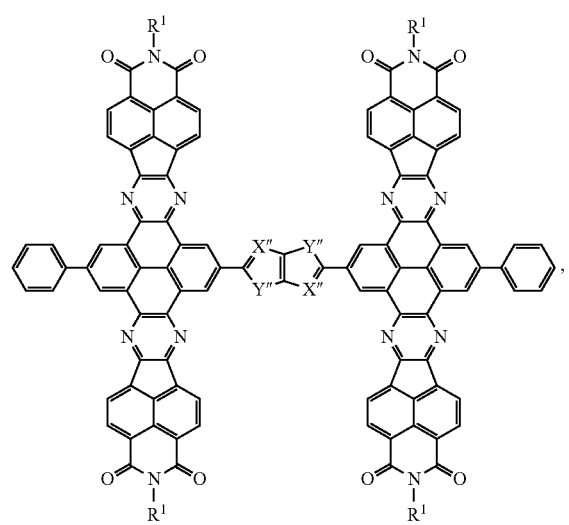
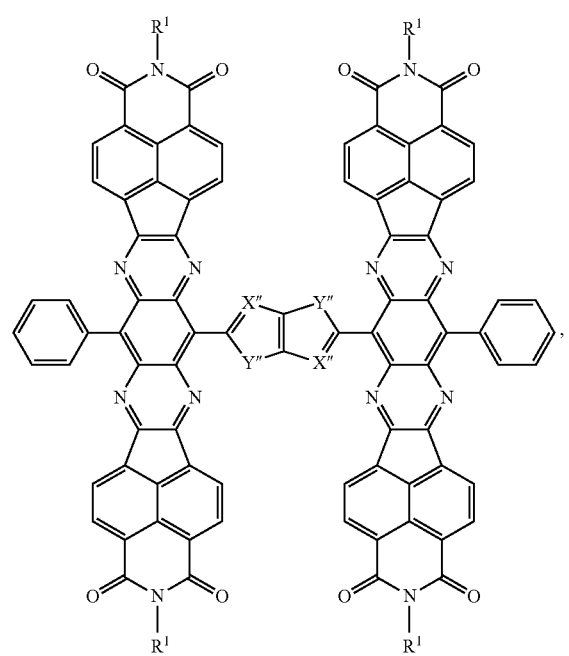
130
-continued
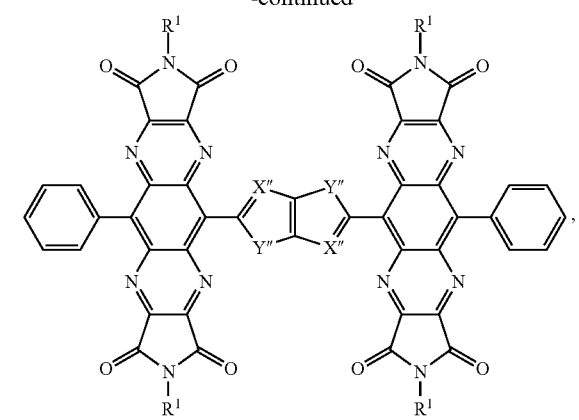
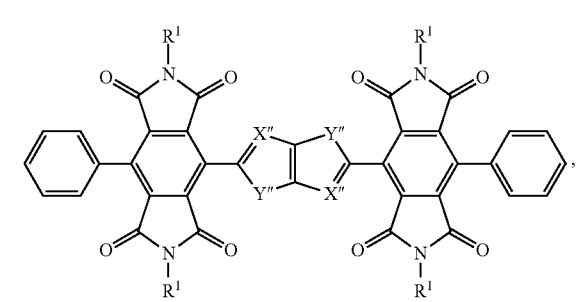
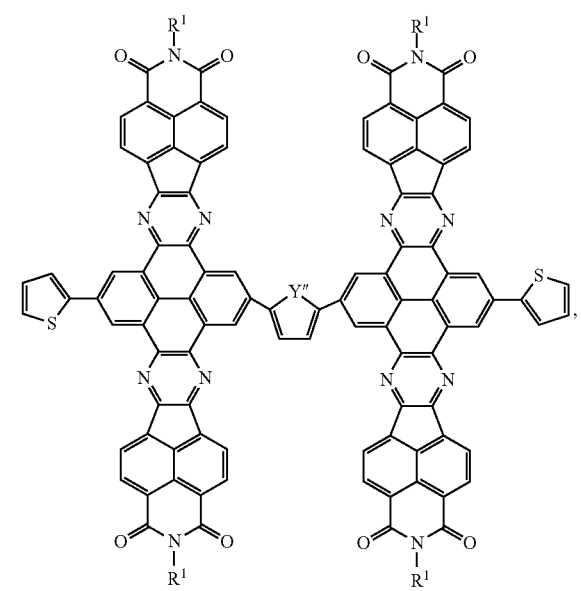

131
-continued
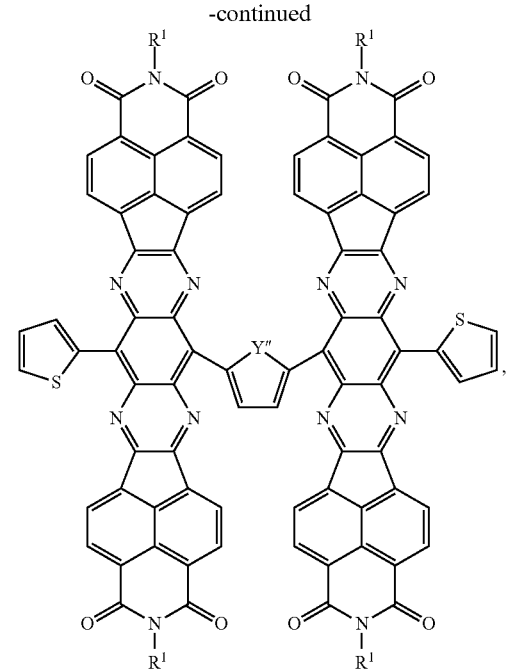
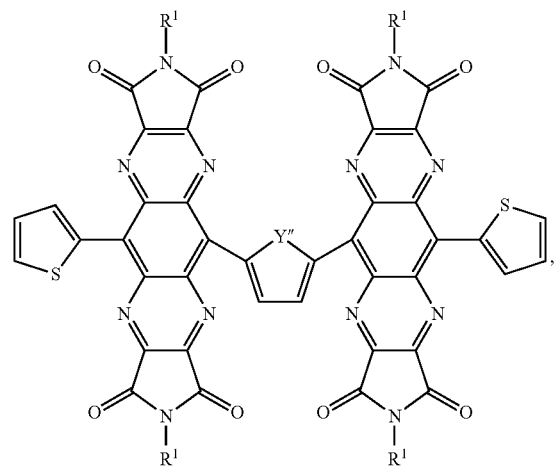
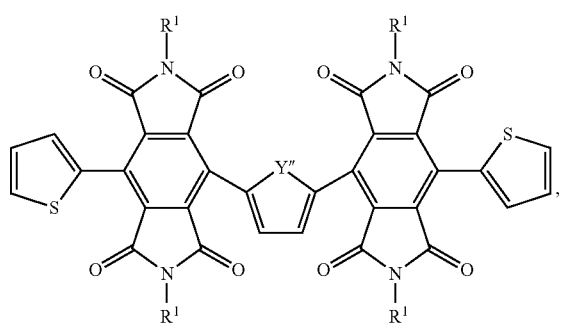
132
-continued
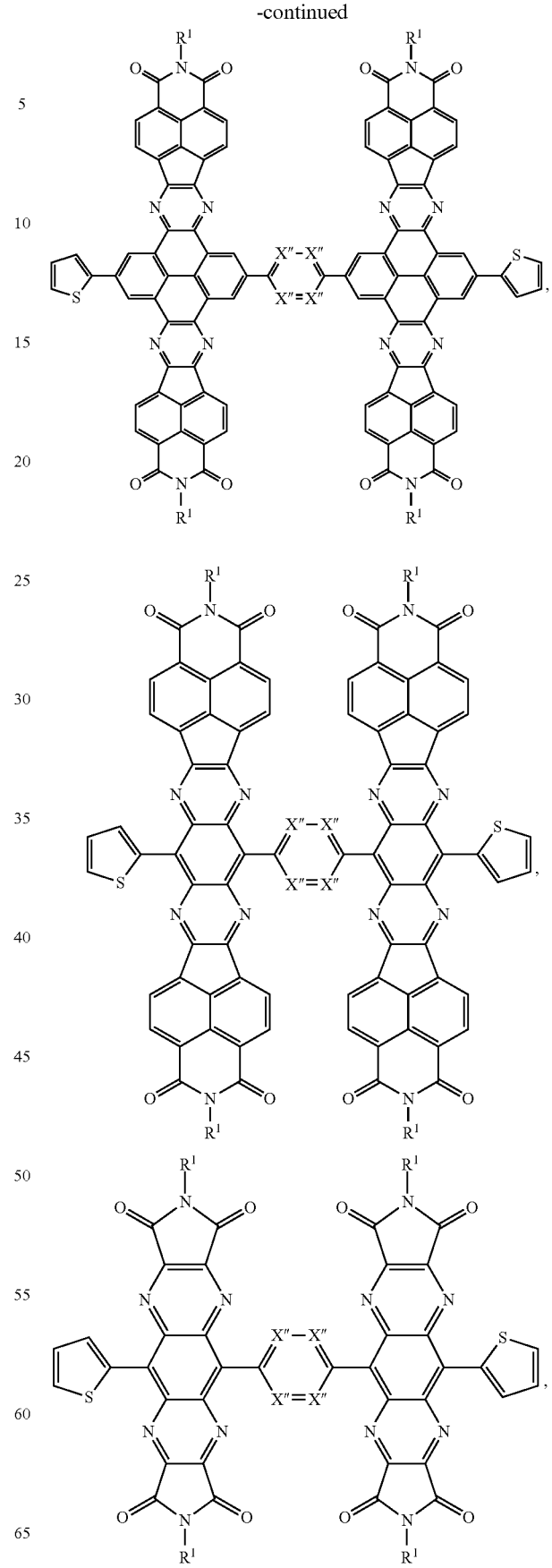

-continued
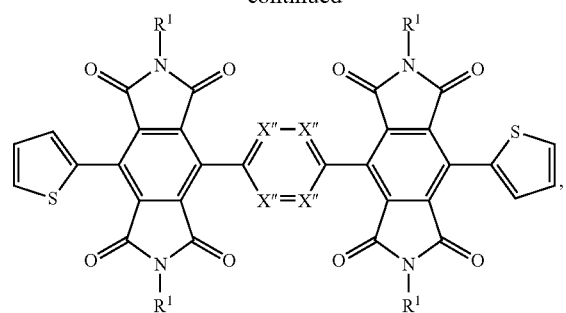
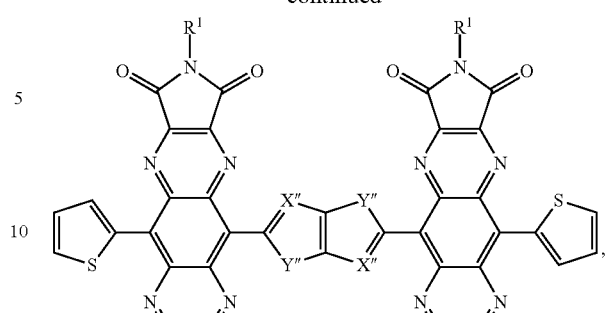
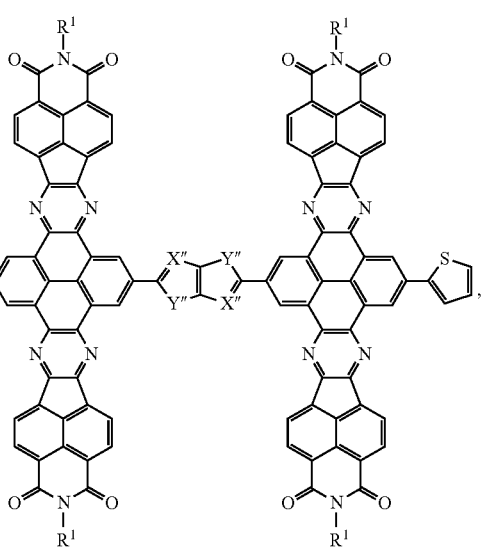
and
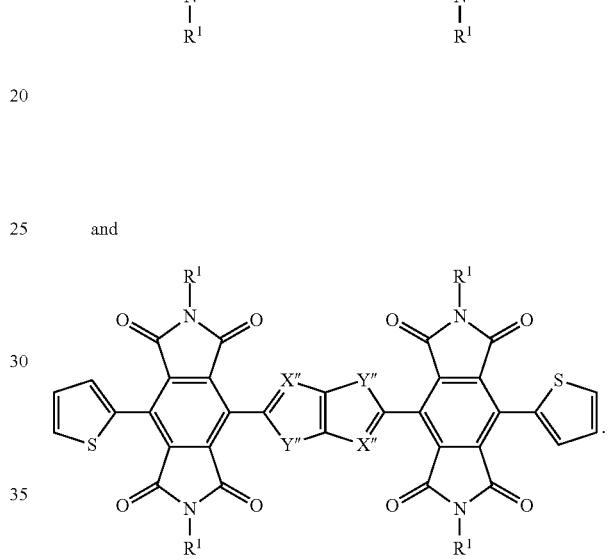
18. The compound of claim 11 selected from
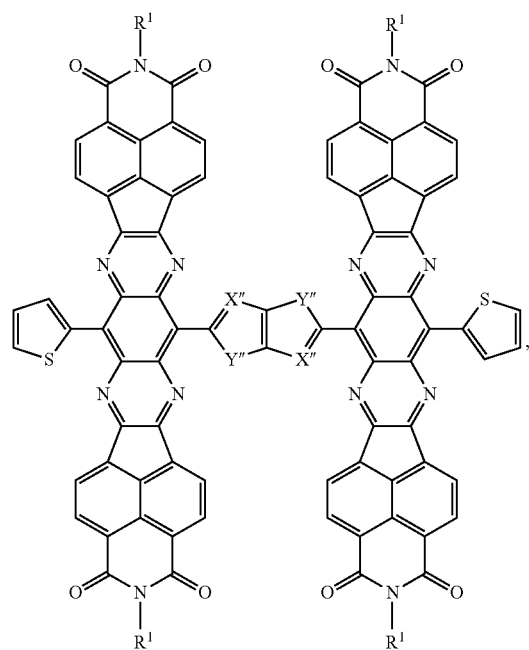
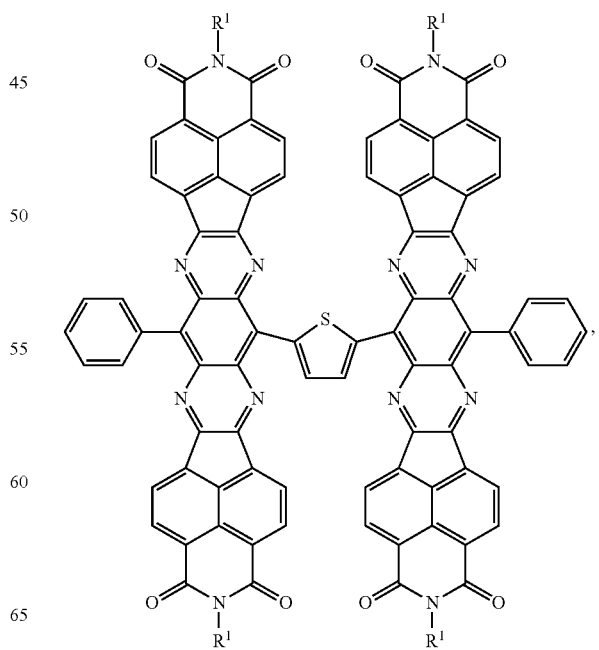

-continued
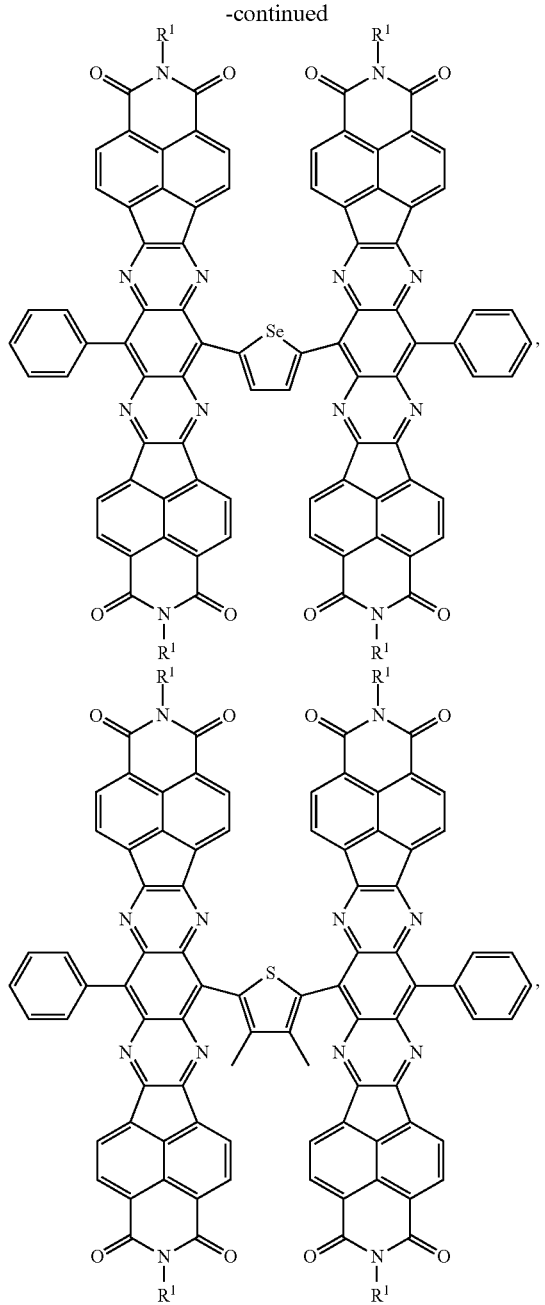
-continued
and
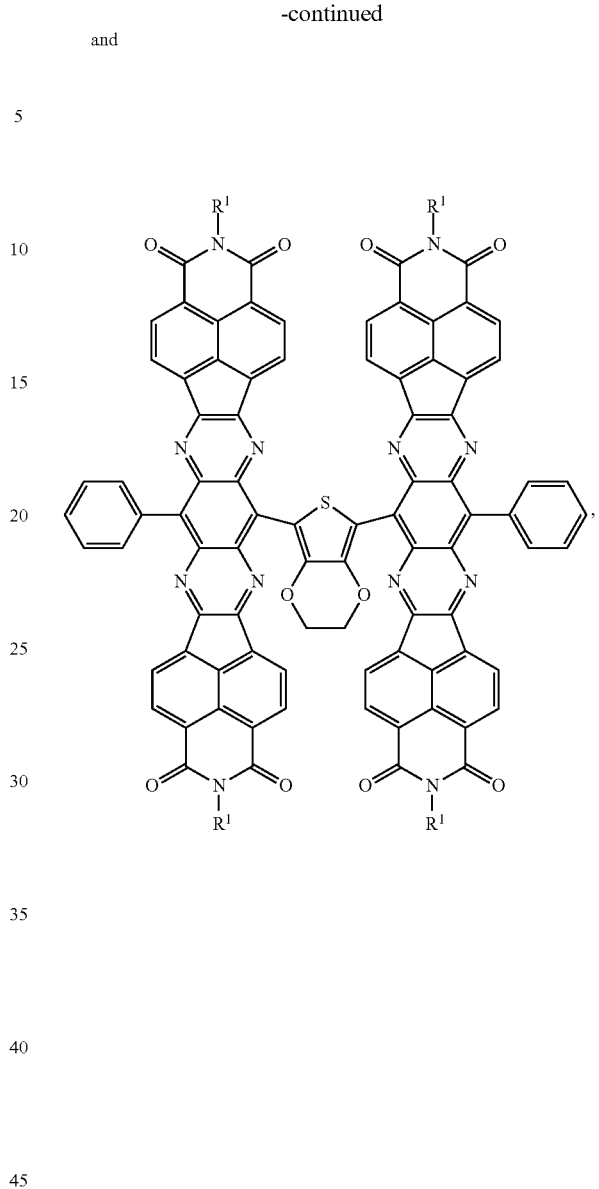
wherein R¹ is a branched alkyl.
19. The compound of claim 18, wherein R¹ is (CH$_2$)CH(C$_{10}$H$_{21}$)(C$_{12}$H$_{25}$) or (CH$_2$)CH(C$_4$H$_9$)(C$_6$H$_{13}$).
* * * * *